(12) United States Patent
Nunes

(10) Patent No.: US 9,295,682 B2
(45) Date of Patent: Mar. 29, 2016

(54) ADJUVANT IMMUNOTHERAPY FOR THE PREVENTIVE, CURATIVE OR PALLIATIVE TREATMENT OF CHRONIC SYSTEMIC DISEASES SUCH AS CANCER, OF CLINICAL MANIFESTATIONS ASSOCIATED WITH DISEASES LIKE CACHEXIA AND CORRECTION OF ADVERSE EFFECTS OF DRUGS SUCH AS IMMUNOSUPPRESSION, NEUTROPENIA AND LYMPHOPENIA, COMPRISING THE ASSOCIATION OR COMBINATION OF A BIOLOGICAL RESPONSE MODIFIER SPECIALLY SELECTED AND OTHER SUBSTANCES WITH ANTINEOPLASTIC ACTION AND/OR OTHER TREATMENTS

(76) Inventor: Iseu da Silva Nunes, Campinas-São Paulo (BR)

( * ) Notice: Subject to any disclaimer, the term of this patent is extended or adjusted under 35 U.S.C. 154(b) by 458 days.

(21) Appl. No.: 13/516,628

(22) PCT Filed: Dec. 15, 2009

(86) PCT No.: PCT/BR2009/000424
§ 371 (c)(1),
(2), (4) Date: Jun. 15, 2012

(87) PCT Pub. No.: WO2011/082458
PCT Pub. Date: Jul. 14, 2011

(65) Prior Publication Data
US 2012/0251441 A1  Oct. 4, 2012

(51) Int. Cl.
*A61K 31/661* (2006.01)
*A61K 33/24* (2006.01)
*A61K 45/06* (2006.01)

(52) U.S. Cl.
CPC .............. *A61K 31/661* (2013.01); *A61K 33/24* (2013.01); *A61K 45/06* (2013.01)

(58) Field of Classification Search
CPC .............................. A61K 33/24; A61K 31/661
USPC ............................................ 424/85.2, 278.1
See application file for complete search history.

(56) References Cited

U.S. PATENT DOCUMENTS

2006/0093628 A1* 5/2006 Nunes et al. ................ 424/274.1
2014/0341940 A1* 11/2014 Nunes ........................ 424/185.1

FOREIGN PATENT DOCUMENTS

EP  0400477 A1  12/1990
EP  1529784 A1  5/2005

OTHER PUBLICATIONS

Justo et al. (European Journal of Pharmacology, 2000, 388: 219-226).*
Byers, T. (CA Cancer Journal, 1999, 49: 353-361).*
Fearon et al. (International Journal of Cardiology, 2002, 85: 73-81).*
NCBI database-Ehrlich ascites tumor (May 8, 2015).*
Tannock, I.F. (Experimental Chemotherapy, Ch. 19-p. 338 and 352-359, in The Basic Science of Oncology, Tannock and Hill, eds., New York 1992).*
A. Mastino et al., "Combination therapy with tymosin alpha 1 potentiates the anti-tumor activity of interleukin-2 with cyclophosphamide in the treatment of the Lewis lung carcinoma in mice" *Int. J. Cancer*, Feb. 1; 50(3) 1992 pp. 493-499.
Y. Kim et al., "Mechanisms involved in synergistic anticancer effects of anti-4-1BB and cyclophosphamide therapy" *Molecular Cancer Therapeutics*, Feb. 8(2) 2009 pp. 469-478.
E. Garaci et al., "Enhanced immune response and antitumor immunity with combinations of biological response modifiers" *Bull. N.Y. Acad. Med.*, Jan. 65(1) 1989 pp. 111-119.

* cited by examiner

*Primary Examiner* — Yan Xiao
(74) *Attorney, Agent, or Firm* — Muncy, Geissler, Olds & Lowe, P.C.

(57) ABSTRACT

The present invention comprises a new combination or association of pharmacologically active substances and/or non-drug treatments for cancer. According to the present invention, the combination or association of substances and/or non-drug treatments is used to treat cancer, clinical problems associated to cancer and adverse side effects related to substances and/or treatments used to fight this illness. The components of the combination or association of substances, the biological response modifier (proteic aggregate of ammonium and magnesium phospholinoleate-palmitoleate anhydride) and at least one substance and/or treatment with antineoplastic properties can be jointly or simultaneously or consecutively or sequentially administered in an appropriate form, according to their chemical properties, and with the use of the most suitable procedures, and also in the most therapeutically effective dose and use.

14 Claims, No Drawings

ADJUVANT IMMUNOTHERAPY FOR THE PREVENTIVE, CURATIVE OR PALLIATIVE TREATMENT OF CHRONIC SYSTEMIC DISEASES SUCH AS CANCER, OF CLINICAL MANIFESTATIONS ASSOCIATED WITH DISEASES LIKE CACHEXIA AND CORRECTION OF ADVERSE EFFECTS OF DRUGS SUCH AS IMMUNOSUPPRESSION, NEUTROPENIA AND LYMPHOPENIA, COMPRISING THE ASSOCIATION OR COMBINATION OF A BIOLOGICAL RESPONSE MODIFIER SPECIALLY SELECTED AND OTHER SUBSTANCES WITH ANTINEOPLASTIC ACTION AND/OR OTHER TREATMENTS

DEFINITIONS

For the purposes of the present invention, systemic diseases are diseases which affect or may affect multiple organs or tissues, or else the whole body, or finally may occur as localized symptoms of disorders that involve whole systems of the body. They can be classified as single factor or multifactorial.

For the purposes of the present invention, chronic diseases are long-term diseases, which tend to become self-perpetuating or to have self-perpetuating cycles.

For the purposes of the present invention, the term cancer means a class or type of chronic systemic disease characterized by uncontrolled growth or multiplication of cells that can invade and destroy adjacent tissues, and which can start new processes or tumors (metastases) spreading to distant parts of the body.

For the purposes of the present invention, the term precancerous lesion means any cell or tissue change that may evolve or change over time and become a cancerous tumor of any kind or degree of malignancy.

For the purposes of the present invention the terms dysplasia, cell dysplasia, metaplasia and cell metaplasia are used to indicate precancerous cell lesions or changes.

For the purposes of the present invention, the term cancer treatment means any measure or procedure for the eradication of tumor or tumor cells, disruption of tumor growth or tumor cells, prevention of the development of tumor cells or tumors, and finally the palliative procedures, measures or cares that although unable to interrupt tumor growth or eradicate tumor and tumor cells, aim at prolonging survival and/or improving the living conditions of patients.

For the purposes of the present invention, the term chemotherapy comprises the treatment of chronic diseases, such as cancer, using substances or drugs.

For the purposes of the present invention, the term chemotherapy protocol comprises the treatments that combine or associate different types of drugs for the treatment of chronic diseases, such as cancer.

For the purposes of the present invention, the term treatment protocol or treatment regimen comprises the treatments that combine drugs and other non-drug procedures for treating chronic diseases, such as cancer.

For the purposes of the present invention, biological response modifiers include all agents, compounds or substances that can act on the body or the immune system, or on any of their elements, changing the host-disease relationship, to benefit the host.

This set or category includes cytokines, substances or cytokine-inducing compounds, immunomodulators, immunoadjuvants, antibodies, vaccines and also any agents or substances that promote the growth and/or multiplication of cells and other components of the immune system and/or increase or improve their functions.

For the purposes of the present invention, the term cellular receptors of the "toll-like" type concern those cellular receptors called "toll like receptors" in English and that can also be identified or abbreviated as "TLR" and "TLRs". These abbreviations are also used in the present report.

CHEMICAL NOMENCLATURE AND OTHER REFERENCES

For purposes of clarification and understanding regarding the state of the art and the invention, bibliographical references, background and technical descriptions will also provided, including patents, when deemed necessary. The chemical compounds and pharmacologically active substances, when necessary, will be referenced by their names and identifiers in the several databases of chemical compounds or classification system, which are also contained in this report.

The databases of products and chemical compounds and/or classification systems used herein are: IUPAC, PubChem, CAS, ATC and DrugBank.

Cancer Treatment—Background—Evolution of the State of the Art

Cancer is generally defined as a class or type of chronic systemic disease, in which the cells grow and multiply in an uncontrolled way, invading and destroying adjacent tissues, and which can start new processes or tumor called metastases, and also by means of cells that spread to distant parts of the body, far from the tumor or cancerous process.

Cancer can affect any animal species at any age, being responsible for millions of deaths annually and incalculable losses. According to data of the World Health Organization, cancer is responsible for around 10% of disease-related deaths each year (Cancer-World Health Organization, 2008) (Cancer-World Health Organization, 2008).

In the current state of the art, cancer treatment comprises five main methods or modalities:

1—Physical removal of a tumor or cells, or else of tumor tissues through surgical techniques 2—Destruction of a tumor or cancerous process through the use of substances or drugs (chemotherapy).

3—Biological therapy or immunotherapy

4—Destruction of a tumor or tumor cells using energy waves, heat and/or radiation (radiotherapy, phototherapy, cryotherapy, electrotherapy)

5—Transplantations of cell populations (transplantation of bone marrow cells and stem cells)

All these modalities or types of treatments, in the current state of the art, can be used either alone or in combination or association.

Cancer Treatment—Surgical Techniques

Surgery is the oldest form of cancer treatment and until very recently was the only medical treatment that offered real chances of long-term survival for patients.

The surgical techniques can represent an effective method of cure in those cases in which solid tumors remain confined to their original sites.

The role of surgery in cancer treatment can be generally divided into six separate areas, and other treatments can be added or associated to allow a better clinical outcome:

a) Definitive surgical treatment; b) Surgery to remove the possibility of residual disease, e.g. radical or total mastectomy to prevent the appearance of residual disease following removal of breast tumor; c) Resection or removal of metastases with curative intent, e.g. surgical removal of liver metastases originating from colorectal cancer; d) Surgery for the treatment of cancer emergencies such as bleedings caused by tumor lysis after successful chemotherapy, abscess drainage; e) Palliative surgeries, frequently necessary to improve the quality of life of patients, such as removal of intestinal obstruction or masses that cause severe pain or threaten to disrupt important functions; f) Reconstruction surgeries or rehabilitation procedures.

Cancer Treatment—Chemotherapy

The term chemotherapy in the state of the art corresponds to the treatment of diseases with the use of drugs or chemical compounds. In the particular case of cancer, the term is sometimes used as a synonym for cancer treatment through drugs or compounds with cytotoxic properties that usually affect cells undergoing rapid division.

In the particular case of cancer, chemotherapy has revolutionized cancer treatment, being one of the most effective treatments available in the state of the art, which can be used either alone or in combination with other compounds or drugs, or else associated or combined with other therapies or treatments, such as, surgery and radiation (radiotherapy).

Main Modalities of Chemotherapy—State of the Art

Polychemotherapy: It is the association of various cytotoxic and/or non-cytotoxic drugs that act synergistically by different mechanisms, with the purpose of reducing the dose of each individual drug and increase the therapeutic effectiveness of all substances when given in combination.

This association of chemotherapy drugs is usually defined according to the type of drugs used in combination or association in chemotherapy, the dosage and timing of administration, which is known in the state of the art as chemotherapy regimen or protocol.

The chemotherapy protocols are often referred to by acronyms or abbreviations formed from initial letters of the drugs used in the treatment, with two chemotherapy protocols and their abbreviations cited for explanatory purposes only. The chemotherapy protocol expressed as the acronym ABVD e.g. concerns the association or combination of the drugs Adriamycin, Bleomycin, Vinblastine and Dacarbazine, being used in the treatment of breast cancer, and the chemotherapy protocol expressed as the abbreviation BEACVPP refers to the combination or association of the drugs Bleomycin, Etoposide, Adriamycin, Cyclophosphamide, Vincristine, Procarbazine and Prednisone.

Adjuvant chemotherapy: It is the type of chemotherapy usually administered after a main treatment, e.g., surgery, in order to decrease the incidence of distant dissemination of cancer.

Neoadjuvant chemotherapy or induction: It is the chemotherapy given before any surgical treatment or radiotherapy, with the purpose of evaluating the effectiveness of treatment in vivo.

In some cases, this type of chemotherapy is aimed at reducing the size of the tumor or the extent of surgery required, and is often used to evaluate the patient's response to chemotherapy drugs and, thus, assist in the elaboration of the best postoperative treatment strategies and protocols.

Concomitant radiochemotherapy: Also called chemoradiotherapy, it is usually used in combination with radiotherapy with the purpose of improving the effects of radiotherapy or acting concomitantly with radiotherapy, optimizing the local effect of radiation.

Main Classes of Chemotherapeutic Compounds—State of the Art

The main types or categories of chemotherapy agents used in the state of the art in cancer treatment, with the most commonly used compounds of each category, their identifiers in the repositories or databases of chemical compounds, such as IUPAC, PubChem, Chemical Abstracts Service (CAS), Anatomical Therapeutic Chemical (ATC) Classification System and other identifiers such as molecular formula, when available, are included for the sole purpose of illustrating the state of the art in this report, which is not intended to be exhaustive, nor is intended to limit the novelty, usefulness or scope of the present invention.

Alkylating agents: The alkylating agents are so called because they can add alkyl groups to cellular DNA, thus interfering with or blocking cell division. Examples of compounds in clinical use: Altretamine [Molecular formula ($C_9H_{18}N_6$) CAS (645-05-6) PubChem (2123)], Mitobronitol [Molecular formula ($C_6H_{12}Br_2O_4$) CAS (488-41-5) ATC (L01AX01) Pub Chem (656655)].

Examples of alkylating agents also include the nitrogen mustards, e.g.: Mechlorethamine [Molecular formula ($C_5H_{11}Cl_2N$) CAS (51-75-2), PubChem (4033)], Cyclophosphamide [Molecular formula ($C_7H_{15}N_2Cl_2O_2P$) CAS (50-18-0) ATC (L01AA01) PubChem (2907) DrugBank (APRD00408)], Ifosfamide [Molecular formula ($C_7H_{15}Cl_2N_2O_2P$) CAS (3778-73-2) PubChem (3690)], Melphalan [Molecular formula ($C_{13}H_{18}Cl_2N_2O_2$) CAS (148-82-3)-ATC (L01AA03) PubChem (4053) DrugBank (APRD00118)] and Chlorambucil [Molecular formula ($C_{14}H_{19}Cl_2NO_2$) CAS (305-03-3)-) PubChem (2708)].

Examples of alkylating agents also include the ethyleneimines and methylmelamines, e.g.: Thiotepa [Molecular formula ($C_6H_{12}N_3PS$), CAS (52-24-4) (ATCL01AC01) PubChem (CID 5453)] and hexamethylmelamine (Altretamine).

Examples of alkylating agents also include the Alkyl sulphonates, e.g. Busulfan [Molecular formula ($C_6H_{14}O_6S_2$) CAS (55-98-1) ATC (L01AB01) PubChem (CID 2478)].

Examples of alkylating agents also include the Nitrosureas, e.g.: Carmustine [Molecular formula ($C_5H_9Cl_2N_3O_2$) CAS (154-93-8) ATC (L01AD01)-PubChem (2578))], Streptozocin [Molecular formula ($C_8H_{15}N_3O_7$) CAS (18883-66-4) ATC (L01AD04)], Hydroxyurea [IUPAC (hydroxyurea), CAS (127-07-1) PubChem (CID 3657)] and the Triazenes, e.g.: Dacarbazine [Molecular formula ($C_6H_{10}N_6O$) CAS (4342-03-4)) PubChem (2942] and Temozolomide [Molecular formula ($C_6H_6N_6O_2$) CAS (85622-93-1) ATC (L01AX03) PubChem (5394)].

Examples of alkylating agents also include the platinum complexes. Examples of compounds in clinical use: Cisplatin [Molecular formula ($H_6Cl_2N_2Pt$), CAS (15663-27-1) PubChem (CID 84691)], Carboplatin [Molecular formula ($C_6H_{14}N_2O_4Pt$) CAS (41575-94-4) DrugBank (APRD00466)], Oxaliplatin, {Molecular formula ($C_8H_{14}N_2O_4Pt$) CAS (63121-00-6) PubChem (CID 77994)], Nedaplatin [Molecular formula ($C_2H_8N_2O_3Pt$) CAS (95734-82-0) PubChem (CID 6917890)], Triplatin Tetranitrate [Molecular formula ($C_{12}H_{54}Cl_2N_{14}O_{12}Pt_3$) CAS (72903-00-3)] and Satraplatin [Molecular formula ($C_{10}H_{22}Cl_2N_2O_4Pt$) CAS (129580-63-8) PubChem (CID 123974)].

Antimetabolites: An antimetabolite is a substance that bears a structural resemblance to a metabolite, which is required for normal biochemical reactions. The antimetabolite competes with or blocks the metabolite, inhibiting cell division, thus being able to prevent the multiplication of cells, including cancerous cells.

They are subdivided into three main categories: Folic acid antagonists, purine analogues and pyrimidine analogues.

Folic acid antagonists: Examples of compounds in clinical use: Aminopterin [Molecular formula ($C_{19}H_{20}N_8O_5$) CAS (54-62-6) PubChem (1693)], Methotrexate [Molecular formula (C20H22N8O5) ATC (L01BA01) PubChem (126941) DrugBank (APRD00353] Pemetrexed [Molecular formula (C20H21N5O6) CAS (137281-23-3) ATC (L01BA04) PubChem (60843)].

Purine analogues: Examples: Azathioprine [Molecular formula (C9H7N7O2S) CAS (46-86-6) PubChem (CID 2265)], mercaptopurine [Molecular formula (C5H4N4S) CAS (50-44-2) PubChem (CID 667490)], Thioguanine [Molecular formula (C5H5N5S) CAS (154-42-7) PubChem (CID 2723601), Fludarabine, [Molecular formula (C10H13FN5O7P) CAS (75607-67-9) PubChem (CID 657237)], Pentostatin [(Molecular formula (C11H16N4O4) CAS (53910-25-1) PubChem (CID 439693)] and Cladribine. [Formula molecular (C10H12C1N5O3) CAS (4291-63-8) PubChem (CID 20279)].

Pyrimidine analogues:—Examples of compounds in clinical use: 5-Fluorouracil [Molecular formula (C4H3FN2O2) CAS (51-21-8) PubChem (CID 3385)], Gemcitabine [Molecular formula (C9H11F2N3O4) CAS (95058-81-4) PubChem (60750)], Floxuridine [Molecular formula (C9H11FN2O5) CAS (50-91-9) PubChem (CID 5790)] and Cytarabine [Molecular formula (C9H13N3O5) CAS (147-94-4) PubChem (CID 6253)].

Mitotic inhibitors: The so-called mitotic inhibitors can block the process of cell division and reproduction (mitosis), stopping cell multiplication.

They are subdivided into four main categories: Vinca alkaloids, terpenoids, epothilones, podophyllotoxin derivatives.

Vinca alkaloids: Examples of compounds in clinical use: Vinblastine [Molecular formula (C46H58N4O9) CAS (865-21-4) PubChem (8935)] Vincristine [Molecular formula (C46H56N4O10) CAS (57-22-7) PubChem (5978)], Vindesine [Molecular formula (C43H55N5O7) CAS (59917-39-4) PubChem (40839)], Vinorelbine, Vinflunine [Molecular formula (C45H54F2N4O8) CAS (162652-95-1) PubChem (6918295)].

Terpenoids: Examples of compounds in clinical use: Paclitaxel [Molecular formula (C47H51NO14) CAS (33069-62-4) PubChem (36314)], Docetaxel [Molecular formula (C43H53NO14) CAS (114977-28-5) PubChem (148124], Tesetaxel [Molecular formula (C46H60FN3O13) CAS (333754-36-2) PubChem (CID 6918574), Larotaxel [Molecular formula (C45H57NO16) CAS (156294-36-9) PubChem (CID 6918260)], Ortataxel [Molecular formula (C44H57NO17) CAS (186348-23-2 PubChem (10557575)].

Epothilones: Example of compound in clinical use: Ixabepilone [Molecular formula (C27H42N2O5S) CAS (219989-84-10) PubChem (6445540)].

Podophyllotoxin derivatives: Example of compound in clinical use: Etoposide [Molecular formula (C29H32O13) CAS (33419-42-0) PubChem (36462)], Teniposide [Molecular formula (C32H32O13S) CAS (29767-20-2) PubChem (34698)]

Antitumor Antibiotics

The so-called antitumor antibiotics are a group of substances with varied chemical structure, which are normally produced by fungi or bacteria, having in common unsaturated rings that allow the incorporation of excess electrons and the consequent production of reactive free radicals, which are toxic to cells, including tumor cells.

They can also include other functional groups that provide them with several mechanisms of action against cell systems, such as alkylation (mitomycin C), enzyme inhibition (actinomycin D and mitramycin) or inhibition of DNA function by intercalation (bleomycin, daunorubicin, actinomycin D and adriamycin and its analogues mitoxantrone and epirubicin).

Anthracyclines: Examples of compounds in clinical use: Daunorubicin [Molecular formula (C27H29NO10) CAS (50-76-0) PubChem (2019)], Doxorubicin [Molecular formula (C27H29NO11) CAS (20830-81-3) PubChem (30323)], Epirubicin [Molecular formula (C27H29NO11) CAS (56420-45-2) PubChem (41867)], Idarubicin [Molecular formula (C26H27NO9) CAS (58957-92-9) PubChem (42890], Mitoxantrone [Molecular formula (C22H28N4O6) CAS (65271-80-9) PubChem (4212)], Pixantrone [Molecular formula (C17H19N5O2) CAS (144510-96-3) PubChem (134019)], Valrubicin [Molecular formula (C34H36F3NO13) CAS (56124-62-0) PubChem (41744)], Amrubicin [Molecular formula (C25H25NO9) CAS (110267-81-7) PubChem (178149)], Aclarubicin [Molecular formula (C42H53NO15) CAS (57576-44-0) PubChem (42474)], Pirarubicin [Molecular formula (C32H37NO12) CAS (72496-41-4) PubChem (3033521)], Zorubicin [Molecular formula: (C34H35N3O10) CAS (54083-22-6) PubChem (9573)].

Streptomycins: Examples of compounds in clinical use: Actinomycin D [Molecular formula (C62H86N12O16) CAS (50-76-0) PubChem (2019) DrugBank (APRD00124)], Bleomycin [Molecular formula (C55H84N17O21S3) CAS (11056-06-7) PubChem (456190)], Mitomycin [Molecular formula (C15H18N4O5) CAS (50-07-7) PubChem (5746)], Plicamycin [Molecular formula (C52H76O24) CAS (18378-89-7) PubChem (29051)].

Topoisomerase inhibitors: The so-called topoisomerase is an enzyme that plays a vital role in DNA replication processes. Thus, topoisomerase inhibitor compounds block or interfere with DNA transcription and replication.

They are subdivided into two categories: type I and type II.

Type I topoisomerase inhibitors: Examples: Camptothecin [Molecular formula (C20H16N2O4) CAS (7689-03-4-) PubChem (2538)], Irinotecan [Molecular formula (C33H38N4O6) CAS (286-90-6) PubChem (3750)], Topotecan [Molecular formula (C23H23N3O5.HCl) CAS (123948-87-8, 119413-54-6—hydrochloride) PubChem (6419854)], Rubitecan [Molecular formula (C20H15N3O6) CAS (91421-42-0)) PubChem (11954380)], Belotecan [Molecular formula (C25H27N3O4) CAS (256411-32-2) PubChem (6456014)].

Type II topoisomerase inhibitors: Examples: Amsacrine [Molecular formula (C21H19N3O3S) CAS (51264-14-3) PubChem (2179)], Etoposide and Etoposide phosphate [Molecular formula (C29H32O13) CAS (33419-42-0) PubChem (36462)-DrugBank (PRD00239)], Teniposide [Molecular formula (C32H32O13S) CAS (29767-20-2) PubChem (346980].

Angiogenesis inhibitors: The term angiogenesis concerns the formation of new blood vessels. Many types of cancer have the ability to attract or form blood vessels into them, which allows them to grow and spread.

Angiogenesis inhibitors have the ability to reduce and/or prevent the formation of new tumor vessels, depriving cancer cells from their means of transport of substances essential to their survival or multiplication.

In the state of the art, for instance, Bevacizumab, a monoclonal antibody that recognizes and blocks vascular endothelial growth factor (VEGF) responsible for stimulating the growth of new blood vessels can be mentioned.

Tyrosine Kinase blockers: The tyrosine-kinases are important enzymes in the process of multiplication of cancerous cells.

Because of this property of tyrosine kinase, many recent drugs in the state of the art were developed with the aim of blocking these enzymes. Example of compounds in clinical use: Erlotinib [Molecular formula (C22H23N3O4 CAS (183321-74-6) PubChem (176870)], Imatinib [Molecular formula (C29H31N7O) CAS (152459-95-5, 220127-57-1—mesilate) PubChem (5291)], Sunitinib [Molecular formula (C22H27FN4O2) CAS (341031-54-7) PubChem (5329102)], Sorafenib [Molecular formula (C21H16C1F3N4O3) CAS (284461-73-0) PubChem (216239)].

Cancer Treatment—Other Compounds Used in the Treatment

Hormones: Although this type of substance cannot be accurately described as a chemotherapy drug, many types of tumors respond to hormone therapy. The growth and reduction of some types of cancer, including those in the breast and prostate tissues, can be related to hormonal balance.

Hormones are involved in many physiological processes. However, they can also favor the growth of some types of cancerous cells, e.g. in cases of breast, endometrial and prostate cancer. In other cases, hormones can eliminate cancer cells, retarding their growth or maintaining the tumor in a latent state.

Due to the influence of hormones on some types of cancer, the use of hormones or hormone blockers is an important part of cancer therapy.

If hormonal suppression is necessary, surgery or radiotherapy directed at specific glands may be indicated, in order to reduce or eliminate the production of hormones that could potentially stimulate or are stimulating the growth of tumor cells.

The steroids, e.g. the dexamethasone may inhibit tumor growth or associated edemas and promote regression of malignant lymph nodes.

Prostate cancer is often sensitive to Finasteride [Molecular formula (C23H36N2O2) CAS (98319-26-7) PubChem (57363)], an agent that blocks the conversion of testosterone to dihydrotestosterone.

Examples of compounds in clinical use: Tamoxifen [Molecular formula (C26H29NO) CAS (10540-29-1) PubChem (5376)], Fulvestrant [Molecular formula (C32H47F5O3S) CAS (129453-61-8) PubChem (CID 104741)], Anastrozole [Molecular formula (C17H19N5) CAS (120511-73-1) PubChem (2187)], Letrozole [Molecular formula (C17H11N5) CAS (112809-51-5) PubChem (902)], Exemestane [Molecular formula (C20H24O2) CAS (07868-30-4) PubChem (0198)] Megestrol [Molecular formula (C22H30O3) CAS (3562-63-8) PubChem (19090)], Goserelin [Molecular formula (C59H84N18O14), CAS (65807-02-5) PubChem (47725)], Leuprolide [Molecular formula (C59H84N16O12) CAS (53714-56-0) PubChem (441410)], Diethylstilbestrol [Molecular formula (C18H20O1) CAS (56-53-1) PubChem (3054)].

Enzymes: Enzymes are proteins specialized in the catalysis of biological reactions. The enzymes also act as regulators of these reactions. In cancer treatment, enzymes such as the L-asparaginase are used because of their ability to deprive cancerous cells, especially leukemic cells, of an amino acid essential for their metabolism (the asparagine), through the conversion of circulating asparagine to aspartic acid and ammonia. Examples of compounds in clinical use: L-Asparaginase [Molecular formula (C18H20O1) CAS (56-53-1) PubChem (3054)].

Biological Therapy or Immunotherapy—State of the Art

The relationship between immunological competence and its importance in the favorable or unfavorable evolution of several diseases, including cancer, has long been recognized, with such knowledge forming part of the state of the art.

Generally speaking, immunotherapy comprises the stimulation of the patient's immune system to enable it to attack and eventually destroy or control invaders and pathological processes.

The term immunotherapy, in the specific case of cancer, concerns a set of strategies or treatments aimed to induce the host's immune system to fight the tumors.

The so-called biological therapy or immunotherapy is a relatively new technique in cancer treatment.

William B. Coley, a North American surgeon of the early 20th century is often credited as being the first to recognize the potential of the immune system in the treatment of tumors, noting that complete regression of tumor was observed in patients with sarcoma after they suffered a bacterial infection.

Based on these observations, he deliberately infected cancer patients with bacteria, achieving complete remission in some cases. For examples of the early state of the art the following publication can be consulted: Coley W B. The treatment of malignant tumors by repeated inoculations of erysipelas: With a report of ten original cases. 1893. Clin Orthop. 1991; 262:3-11.

From the seventies, because of advances in the state of the art, a wider knowledge of some of the mechanisms involved in the recognition and rejection of tumors and malignant cells at the cellular and molecular level has become possible.

In 1976, the once called T-cell growth factor, currently known as interleukin-2 (IL-2) was identified and cloned, allowing for more in-depth study of the mechanisms of T-cells and their role in the mechanisms of recognition and protection of the immune system.

The aforementioned discoveries, among others, have boosted the research on cytokines, and, as a result of such advances in the state of the art, several cytokines, such as interferons (IFN) and interleukin-2 (IL-2) began to be used as agents in cancer treatment.

The discovery of the role of cytokines has also stimulated a high demand for new means and substances able to increase and modify their activity, for therapeutic purposes.

This search led to the development of various compounds able to interfere with the production or expression of cytokines, and some of them are used in the state of the art as drugs in cancer treatment.

The availability of new compounds has given great impetus to immunotherapy, being incontestable in the state of the art the recognition of its usefulness in treating several chronic systemic diseases, including cancer.

Immunotherapy can be classified into active and passive, according to the substances used and the mechanisms of action.

In active immunotherapy, substances that stimulate and/or restore the immune function (nonspecific immunotherapy) and tumor cell vaccines (specific immunotherapy) are administered with the purpose of intensifying resistance to tumor growth.

In passive or adoptive immunotherapy, antitumor antibodies or mononuclear cells are administered, aimed to make the immune system able to fight the disease.

The most recent developments in the state of the art are represented by the so-called monoclonal antibodies and anticancer vaccines.

Cancer Treatment—Use of Cytokines—Main Cytokines Used—State of the Art

Cytokines are proteins or glycoproteins secreted by immune cells that act as messengers of the immune system, activating or controlling several other cell populations that are ultimately responsible for fighting invading microorganisms and tumor cells.

Although they were originally identified as substances produced naturally in the body or endogenously by cells and components of the immune system, in the state of the art, several types of cytokines are obtained in large quantities from sources outside the body, i e, exogenously, by means of genetic engineering and cell culture methodologies, which has made the treatment of many diseases possible with the use of the referred substances.

In the specific case of cancer, several exogenous cytokines are used in the state of the art. The main types of cytokines used in clinical practice are interferons, interleukin-2 (Il-2), interleukin-12 a (Il-12) and granulocyte-macrophage colony-stimulating factors (G-CSF and GM-CSF).

For the purpose of illustrating the state of the art without intending to limit the scope of the present invention, some examples of cytokines in clinical use are presented here.

Interferons (IFN): The so-called interferons were isolated from white blood cells in the 1970's by investigators who sought antiviral substances. Three main types of interferons are identified in the state of the art: Interferon-alpha (IFN-alpha), beta (IFN-beta) and gamma (IFN-gamma), all possessing antiviral, antitumor and immunomodulatory properties, among other biological activities.

In the treatment of some types of cancer, interferon-alpha monotherapy is definitely the treatment of choice for the so-called hairy cell leukemia in the state of the art. (Quesada J R, Hersh E M, Manning J, et al. Treatment of hairy cell leukemia with recombinant alfa-interferon. Blood. 1986; 68:493-497).

In general, for other types of cancer, interferon alpha used alone in clinical practice has shown few significant results.

A response rate around 20% was obtained in clinical trials using high doses of interferon-alpha alone, for the treatment of metastatic melanoma, which is not higher than the response rate of other chemotherapy agents used alone to treat this type of cancer. (Dorval T, Palangie T, Jouve M, et al. Treatment of metastatic melanoma with recombinant interferon alfa-2b. Invest New Drugs. 1987; 5: S61-S63) and (Sertoli M R, Bernego M G, Ardizzoni A, et al. Phase II trial of recombinant alfa-2b interferon in the treatment of metastatic skin melanoma. Oncology. 1989; 46:96-98.).

A significant increase in survival rates of patients was observed, in clinical trials, with the use of interferon-alpha, as monotherapy, for treatment of chronic myeloid leukemia, although not followed by significant remission of their underlying disease. (Allan N C, Richards S M, Shepherd P C. UK Medical Research Council randomized, multicenter trial of interferon alfa n1 for chronic myeloid leukaemia: improved survival irrespective of cytogenetic response, Lancet. (1995; 345:1392-1397)

For these reasons, although this cytokine has shown significant results in the treatment of many types of cancer, the greatest tendency in the state of the art regarding the use of interferons for treating cancer recommends their use associated to other substances, such as chemotherapy drugs, or else other cytokines, aimed to increase therapeutic effectiveness.

Regarding its use in combination with other cytokines, some clinical trials report good survival rate of patients with metastatic renal cancer treated with protocols of interferon-alpha associated to interleukin-2 (Il-2). For an example of state of the art research, please see: (N J Vogelzang, A Lipton and R A Figlin—Subcutaneous interleukin-2 plus interferon alfa-2a in metastatic renal cancer: an outpatient multicenter trial, 1993, Journal of Clinical Oncology, Vol 11, 1809-1816).

The same combination of cytokines has shown significant results regarding survival rates in clinical study with 39 patients with melanoma and 35 patients with advanced kidney cancer (SA Rosenberg, M T Lotze, J C Yang, W M Linehan, C Seipp, S Calabro, S E Karp, R M Sherry, S Steinberg and DE White, Combination therapy with interleukin-2 and alpha-interferon for the treatment of patients with advanced cancer, 1989, Journal of Clinical Oncology, Vol 7, 1863-1874).

A major obstacle to the use in clinical practice of exogenously obtained interferons is its high rate of occurrence of unwanted side effects, which often lead to reduction of the dose or treatment discontinuation, with negative consequences for the treatment of patients.

The main adverse side effects related to interferon are: Flu-like symptoms, severe fatigue, insomnia, reduction of blood cells, bone pain, thyroid dysfunction, drug-induced diabetes, neuropsychiatric alterations, retinopathy, hearing and gastrointestinal alterations.

Interleukin-2 (Il-2): Interleukin-2 (IL-2) is a protein naturally produced by the human body, which acts as a growth or multiplication factor in T lymphocytes.

As for the IL-2 used in cancer treatments is obtained from exogenous sources involving recombinant DNA techniques and others. For an example of state of the art research in obtaining and purification of IL-2, please see: U.S. Pat. No. 5,149,788—(Purification of chimeric proteins containing an IL-2 moiety by receptor-affinity chromatography).

The IL-2 obtained from exogenous sources is licensed by the Food and Drug Administration (FDA) for the treatment of kidney cancer, and its significant therapeutic effects on patients have been reported in many clinical trials. (Lissoni P, Barni S, Tancini G, et al. Clinical response and survival in metastatic renal carcinoma during subcutaneous administration of interleukin-2 alone. Arch Ital Urol Androl. 1997; 69:41-47.)—Tourani J M, Lucas V, Mayeur D, et al. Subcutaneous recombinant interleukin-2 (rIL-2) in outpatients with metastatic renal cell carcinoma. Results of a multicenter SCAPP1 trial. Ann Oncol. 1996; 7:525-528).

In clinical trials with patients with melanoma IL-2 increased the survival rates of many individuals, which were higher than the average survival rates usually obtained with chemotherapy drugs. (Rosenberg S A, Yang Y C, Topalian S L, et al. Treatment of 283 consecutive patients with metastatic melanoma or renal cell cancer using high-dose bolus interleukin-2 JAMA. 1994; 271:907-913).

When used in comparative studies with interferon-alpha (IFN-alpha), in an extensive study involving 425 cancer patients, both the interleukin-2(IL-2) and the interferon-alpha (IFN-alpha) had poor therapeutic response when used alone. However the combined use of two cytokines, evaluated in the same protocol, showed significantly higher response rates compared with the use of either one alone. (Negrier S, Maral J, Drevon M, Vinke J, Escudier B, Philip T. Long-term follow-up of patients with metastatic renal cell carcinoma treated with intravenous recombinant interleukin-2 in Europe. Cancer J Sci Am. (2000; 6: S93-S98)

The main difficulty in using exogenous IL-2 and other exogenous cytokines is their high toxicity, with side effects of considerable magnitude, particularly cardiac symptoms and dysfunctions, septic shock, fever, which require intensive care for their remediation or control, and may also lead to discontinuation of treatment with the referred cytokine.

Interleukin-12 (IL-12): Interleukin-12 (IL-12) is a protein naturally occurring in the body that has been intensely studied because of its ability to promote or stimulate activity of NK cells and T lymphocytes, and because it is a stimulating factor for B cells. Has demonstrated antitumor activity in studies that use animal models for cancer.

The IL-12 used in cancer treatments is obtained from exogenous sources involving recombinant DNA techniques and others. For some examples of procurement, purification and biological properties in the state of the art: PCT/US91/06332, PCT/US91/06332e ainda U.S. Pat. No. 5,853,714—Methods for the purification of interleukin-12 (IL-12).

The IL-12 obtained from exogenous sources was used alone in protocols involving patients with metastatic kidney cancer, with minimum therapeutic results. (Atkins M B, Roberston M J, Gordon M, et al. Phase I evaluation of intravenous recombinant human interleukin-12 in patients with advanced malignancies. Clin Cancer Ris. 1997; 3:409-417.).

The trend of research with IL-12 in the current state of the art recommends the use of this cytokine as an adjuvant therapy in treatments such as surgery, used in combination with other cytokines and chemotherapy drugs. (For instance: B A Teicher, G Ara, D Buxton, J Leonard and R G Schaub, Clinical Cancer Research, Vol 3, Issue 9 1661-1667)) and finally in anticancer vaccines, to enhance immune response to antigens. An example of state of the art research follows: Lee P, Wang F, Kuniyoshi J, et al. Effects of interleukin-12 on the immune response to a multipeptide vaccine for resected metastatic melanoma. J Clin Oncol. 2001; 19:3836-3847.

Granulocyte-macrophage colony-stimulating factors or growth factors that stimulate myelopoiesis These are well-known cytokines, extensively used in the state of the art in surgeries that involve the implantation of stem cells and bone marrow cells, for reconstitution of the myeloid series.

These are the cytokines most commonly used for the reconstitution of the myeloid series, jointly or sequentially with chemotherapy and radiotherapy, being incontestable in the state of the art for this therapeutic purpose.

They are produced by techniques that involve cell cultures, among other methods. For an example of state of the art research, please see: U.S. Pat. No. 6,020,169—Production of secreted foreign polypeptides in plant cell culture.

Besides their use as stimulants of myeloid response, experimental data suggest their effectiveness when used alone in patients with melanoma, contributing to the significant increase in survival time and in the time period between recurrences. For an example of the state of the art research, please see: Spitler L E, Grossbard M L, Ernstoff M S, et al. Adjuvant therapy of stage III and IV malignant melanoma using granulocyte-macrophage colony-stimulating factor. J Clin Oncol. 2000; 18:1614-1621.

There are also reports in the state of the art on their efficiency when used in combination with therapeutic vaccines against cancer, for the treatment of lymphomas: (Bendandi M, Gocke C D, Kobrin C B, Benko F A, Sternas L A, Pennington R, Watson T M, Reynolds C W, Gause B L, Duffey P L, Jaffe E S, Creekmore S P, Longo D L, Kwak L W, Complete molecular remissions induced by patient-specific vaccination plus granulocyte-monocyte colony-stimulating factor against lymphoma, Nat Med. 1999 October; 5(10): 1124-5).

Cancer Treatment—Immunotherapy—Vaccines—State of the Art

The therapeutic vaccines against cancer, in the current state of the art, are considered a modality of immunotherapy because they generate an immune response of the body to defend itself against tumors or neoplastic cells.

Several strategies aimed to stimulate the immune system using therapeutic vaccines have been explored and are reported in the state of the art. Vaccines made from peptides or proteins administered with adjuvants have been reported with varying degrees of effectiveness.

For examples of state of the art research, please see: Jaffee E M, Hruban R H, Biedrzycki B, et al. Novel allogeneic granulocyte-macrophage colony-stimulating factor-secreting tumor vaccine for pancreatic cancer: a phase I trial of safety and immune activation. J Clin Oncol. (20001; 19:145-156) e Hsueh E C, Famatiga E, Gupta R K, Qi K, Morton D L. Enhancement of complement-dependent cytotoxicity by polyvalent melanoma cell vaccine (CancerVax): correlation with survival, Ann Surg Oncol. 1998; 5:595-602 and finally, Hanna M G Jr., Hoover H C Jr, Vermorken J B, Harris J E, Pinedo H M. Adjuvant active specific immunotherapy of stage II and stage III colon cancer with an autologous tumor cell vaccine: first randomized phase III trials show promise. Vaccine. 2001; 19:2576-2582.

Among other products and treatments available in the state of the art, it is worth mentioning, for purposes of explanation only, the BCG vaccination, originally developed to be used (and still widely used for this purpose) in the preventive treatment of tuberculosis, which is now used as immunomodulator for the treatment of malignant melanomas and bladder cancer and the use of interferons and other cytokines (11-2-2, IL-12) for the treatment of these tumors.

Some examples of the state of the art include: BCG immunotherapy of bladder cancer: 20 years on The Lancet, Volume 353, Issue 9165, Pages 1689-1694.

The adjuvants to be used in these vaccines to boost the immune response and, thus, maximize the effect of therapeutic vaccines against cancer, increasing the body's ability to respond to antigens, are compounds such as components of bacterial cell walls, composed mainly of lipopolysaccharides (LPS) aimed to stimulate inflammatory response, biological response modifiers and also cytokines such as IL-12 or granulocyte-macrophage colony-stimulating factors (GM-CSF), used for the same purpose.

Anticancer therapeutic vaccines are among the most recent developments in the state of the art, and they use dendritic cells that are being intensively studied and tested as therapeutic vaccines in many situations of clinical interest.

Some examples of state of the art research follow: Banchereau J, Palucka A K, Dhodapkar M, et al. Immune and clinical responses in patients with metastatic melanoma to CD34+ progenitor-derived dendritic cell Vaccine. Cancer Res. 2001; 61:6451-6458) and Sadanga N, Nagashima H, Mashino K, et al. Dendritic cell vaccination with MAGE peptide is a novel therapeutic approach for gastrointestinal carcinomas. Clin Cancer Res. 2001; 7:2277-2284.

State of the Art—Immunotherapy—Monoclonal Antibodies

Antibodies are compounds (proteins) produced by the body, through specialized cells of the immune system (B lymphocytes) when stimulated by the presence of compounds (antigens) present in microorganisms and/or produced by cells.

All cells possess or express some types of proteins in their surface, with a high level of specificity for each kind of cell population.

Based on such information, and with the evolution of the state of the art, various types of antibodies were designed or manufactured in laboratory to recognize and bind to certain antigens on cell surface, or else expressed by mechanisms of cell division and growth.

The so-called monoclonal antibodies are pure antibodies produced in laboratory using cell cultivation techniques, or else from B lymphocytes of rodents whose immune systems were stimulated by antigens of interest.

Called monoclonal because they were obtained from cell clones, being thus identical in what concerns their physicochemical and biological properties.

In the early days of their application, because of their animal origin, these antibodies maintained parts and/or components characteristic of the original cell type, and these components caused and/or stimulated an immune response to the antibody itself, when used continuously, which caused their inactivation, invalidating their therapeutic use.

Therefore, monoclonal antibodies were used for a long time for diagnostic purposes, only, because of their high level of specificity for some pathological agents and processes and also because its continuous use is not necessary for this type of procedure.

An example of the state of the art is the use of antibody complexes with radioactive isotopes to locate tumors or metastases in any part of the body.

With the advance of the state of the art, notably of genetic engineering, the components or parts of these antibodies that were responsible for triggering the body's immune response, were altered or inactivated without changing the affinity of the antibody for its respective antigen, and ensuring its continuous use in therapeutic processes in target cells that express or contain these antigens.

In the specific case of cancer, the reasoning or rationale for its use is also based on the fact that all cells, including cancer cells, contain or express some types of proteins (antigens) on their surface, with a high level of specificity of each kind of cell population.

With the increasing knowledge on the human genome, many proteins (antigens) existing or produced by neoplastic cells were identified, and based on such knowledge, several monoclonal antibodies were (and are) specifically designed or artificially obtained with the purpose of recognizing these specific antigens of neoplastic cells.

After entering the body of the host, the monoclonal antibody attaches itself to this cell surface protein of the cancer cell. This action may prevent the cell to send biochemical signals important for its growth and multiplication, and also activate the immune system of the host in order to fight and destroy cancer cells.

Other therapeutic applications or strategies that have already been described and/or used in the state of the art include the use of monoclonal antibodies as carriers of cytotoxic drugs (Gemtuzumab ozogamicin), radioactive isotopes (Ibritumomab tiuxetan) or both, (European Patent—EP0282057), and even cancer cells, making use of the high level of specificity of these antibodies to attempt to selectively increase the destruction of cancer cells, sparing the normal populations.

In the state of the art there are also examples of pure monoclonal antibodies or in complexes with other compounds, being used in treatment protocols associated to other compounds, particularly cytotoxic drugs and biological response modifiers, in order to maximize the therapeutic effect.

Other examples of state of the art research follow: Hurwitz H, Fehrenbacher L, Novotny W, Cartwright T e cols. Bevacizumab plus irinotecan, fluorouracil, and leucovorin for metastatic colorectal cancer. N Engl J Med. 2004 Jun. 3; 350(23): 2335-42; McLaughlin D, Rodriguez M A, Hagemeister F B et al. Stage IV indolent lymphoma: a randomized study of concurrent vs. sequencial use of FND chemotherapy (fludarabine, mitoxantrone, dexamethasone) and rituximab monoclonal antibody therapy, with interferon maintenance. Proc Am Soc Clin Oncol 2003; 102:564, abstract 2269.

State of the Art—Examples of Existing Products—Monoclonal Antibodies

For purposes of illustrating the state of the art, and without intending to limit the scope of the present invention, some examples of compounds in clinical use are provided: Alemtuzumab, bevacizumab, cetuximab, ocrelizumab, ofatumumab, panitumumab, rituximab, trastuzumab. Monoclonal antibodies conjugated with cytotoxics: Gemtuzumab ozogamicin, Monoclonal antibodies conjugated with radioactive particles: Ibritumomab tiuxetan, Tositumomab.

Clinical Problems Related to Cancer—Main Difficulties and Problems Related to Treatments—State of the Art Despite significant advances in medicine, many types of tumors still show disappointing response to all types and modalities of treatments available, as for example, small cell lung cancer, stomach cancer, pancreatic cancer, cervical cancer, invasive melanoma, cancer of the adrenal cortex and soft tissue sarcomas. Additionally, many types of tumors or cancerous cells possess or develop mechanism that makes them resistant to chemotherapy and radiotherapy.

Regarding cancer prevention or preventive treatment, there is an urgent need to develop new treatments, because few effective treatments are available in the state of the art.

Preventive therapeutic action in cancer is based on the information that several types of cancers such as malignant skin tumors, those that affect epithelial tissue lining of internal organs, cervical cancer, among others, begin in small populations of normal cells in which aggressive external agents such as solar radiation, chemical products and some types of viruses can induce or promote cell alterations considered precancerous lesions, that over time have the ability to become tumors of high grade malignity and great mortality.

Therefore, it is essential that these precancerous lesions are eliminated or reversed early, which requires the availability of new and better drugs and treatments, for use alone or in combination with the existing therapies.

Regarding the treatment of cancer using surgical techniques, one of the main difficulties faced in the total elimination of the tumors is that, at the time of diagnosis, a considerable number of cancer patients already have micro metastases or metastases in other parts of the body, far from the original location of the tumor, and in most cases these metastases cannot be detected during the surgical procedure.

Aiming to increase the chances of successful surgery, in the state of the art in medicine, new strategies have been developed in view of the ever-present possibility of occurrence of micro metastases or metastases, although these are undetectable at the time of the surgical procedure.

In such cases, the availability of non-surgical treatment modalities, such as the previous, concomitant or subsequent administration of chemotherapy drugs, had a great impact on cancer treatment, greatly improving the chances of patients undergoing surgery.

As an example of these strategies, neoadjuvant or induction chemotherapy can be cited, which consists in treating the patient with drugs, usually cytotoxic drugs, before surgery.

In some cases, this type of chemotherapy is aimed at reducing the size of the tumor or the extent of surgery required and is often used to evaluate the patient's response to chemotherapy drugs and, thus, assist in the elaboration of the best postoperative treatment strategies and protocols.

Another modality of treatment is adjuvant chemotherapy, which consists in administering chemotherapy drugs to the patient, alone or in association with other drugs, after surgery, with the purpose of blocking the formation or development of tumors close or far from the main location, or finally, to reduce the tumor growth rate, in the cases of micro metastases or metastases refractory to treatment.

Finally, depending on tumor staging, that is, on the phase of tumor growth, its location or the presence of metastatic disease, cytotoxic medications may cease to be effective. Therefore, combinations of drugs with different mechanisms of action are increasingly used in the state of the art to improve the success of therapies and treatments.

These combinations, which are called chemotherapy regimens or protocols that involve the use of various compounds, combined or associated, depending on patient and disease state, are common practices in the state of the art.

Despite the advances in the state of the art, thanks to the development of new drugs and treatments for severe systemic diseases, such as cancer, there are still many difficulties and problems associated to drugs and treatments that often have a negative impact on their effectiveness.

However, while it is undeniable that the greater availability of new drugs intended for use in chronic systemic diseases, such as cancer, as well as the adoption of treatment protocol involving the combination of various drugs for the treatment of one patient, has led to a significant increase in the response rate of response to treatment and to a higher survival rate for patients, on the other hand, there are many serious adverse side effects associated to the use of these drugs and/or combinations of drugs.

Examples include adverse side effects associated to the use of cytotoxic drugs, because they have the ability to interfere with multiple cellular metabolic processes and, thus, indiscriminately affect tumor and normal cells, causing severe problems, such as immunosuppression, hair loss or alopecia, damage to the mucous membranes in the digestive tract, to name the most common adverse side effects.

Some cytotoxic antibiotics used in cancer treatment, e.g., doxorubicin, mitoxantrone and mitomycin, act on DNA replication and on the integrity of cellular DNA, being generally toxic and adversely affecting both cancerous and healthy cells.

Other widely used compounds, such as vinca alkaloids and taxanes, act on various essential cell structural components and, thus, damage healthy cells too.

In general, it can be said that most cytotoxic drugs used in the treatment of chronic systemic diseases, such as cancer, damage healthy cells too, including bone marrow cells, cells of the gastrointestinal tract and other important cell structures, this being one of the major problems regarding the use of the aforementioned drugs.

Severe adverse effects associated to their use may interfere with the effectiveness of cancer treatment itself, because they can lead to reduction of the dose (dosage or period of administration) or even to treatment discontinuation.

Finally, radiotherapy, one of the most common treatments for some types of cancer, besides causing damage to tissues and organs, can also affect the immune response, contributing to the decrease in the number of circulating lymphocytes, mainly B and T lymphocytes. For an example of state of the art research, please see: Helman, Principle of Radiation Therapy, in Cancer Principles and Practice of Oncology, Vol. 1, 3nd Ed.—DeVita et al. Eds, J. B. Lippincott Co. Publ.—247-275 (1989).

Hematological and immunological abnormalities such as anemia and neutropenia, respectively, which can be associated to the use of chemotherapy compounds and/or radiation, are common and serious complications for patients undergoing treatment.

Neutropenia associated to the use of several drugs and other non-drug treatments such as radiotherapy is a serious undesirable event for patients with chronic systemic diseases, such as cancer, because besides providing suitable conditions for the occurrence of infectious events caused by opportunistic pathogens, they have also a negative impact on the function of components and other cell elements of the immune system of the host, which are also very important in fighting cancer cells.

In general, the same problems associated to the use of compounds or drugs such as poor therapeutic response, adverse side effects, immunosuppression, neutropenia and anemia are common occurrences for the other treatments available in the state of the art for cancer, such as radiotherapy.

Another serious clinical complication associated to cancer and other chronic systemic diseases is cachexia (Greek word that means poor condition) also known as malnutrition-cachexia syndrome and which can be further complicated when drugs and other treatments are added.

Finally, in the event of serious systemic diseases, such as cancer, the quality of life of patients is significantly affected either by the disease or by clinical conditions associated with the disease, such as cachexia and/or by the worsening of clinical and psychological conditions associated to adverse effects related to the disease and treatments.

Occurrence of tumor resistance, poor therapeutic response in many cases, accelerated physical deterioration, metastatic processes, deterioration of quality of life, among others, are adverse consequences for the whole body affected by the primary disease and/or aggravated by the use of existing treatments and drugs, and which are major challenges to be faced in the state of the art. Thus, new inventions and improvements are needed in the treatment of chronic diseases, such as cancer.

The present invention, as will be widely explained and demonstrated, shall contribute innovatively to the resolution of these problems in various ways.

And in order to demonstrate and facilitate understanding of the state of the art, novelty and usefulness of the present invention, several aspects and important clinical conditions associated to chronic diseases, such as cancer, the treatments available in the state of the art and the main difficulties and/or limitations associated to their use, as well as relevant information to the understanding of the usefulness of the invention for the treatment of these diseases and associated clinical conditions and for the solution or minimization of the problems and limitations of the existing treatments are detailed here.

Main Clinical Complications Associated to Chronic Systemic Diseases—Cachexia or Anorexia—Cachexia Syndrome—Drugs and Treatments—State of the Art Malnutrition and cachexia are morbid conditions often presented by patients with serious chronic systemic pathologies, such as cancer.

In the common form of malnutrition, the body turns to its own fat reserves, sparing the muscle tissue, whereas in cachexia, there is equal mobilization of these reserves and quick loss of muscle and fat. For examples of state of the art research please see: Body J J. The syndrome of anorexia-cachexia. Curr Opin. Oncol. 1999; 11(4):255-60) e Moley J F Aamodt R, Rumble W, Kaye W, Norton J A. Body cell mass in cancer bearing and anorexia patients. J Parenter. Ent. Nutr. (1987; 11:219-22).

Cachexia in cancer patients is a complex syndrome clinically characterized by generalized depletion of muscle and fat tissues, causing progressive and involuntary weight loss, anemia, astenia, negative nitrogen balance, immune dysfunction and metabolic changes. For examples of the state of the art research, see: Labow B I, Souba W W. Nutrition. In: International Union Against Cancer-Manual of Clinical Oncology. 7 ed. New York: Wiley-Liss; 1999. p. 757-77 and also Martignoni M E, Kunze P, Friess H. Cancer cachexia. Mol Cancer. 2003; 2:36 and finally; Rubin H. Cancer cachexia: its correlations and causes. Proc. Natl Acad Sci USA. 2003; 100(9): 5384-9.

Because of its relation with anorexia, the term Cachexia-anorexia syndrome or CAS, (abbreviation) has been used frequently in the state of the art to describe clinical pictures of malnutrition and cachexia associated to cancer and other serious systemic diseases.

Anorexia-Cachexia—ACS—Causes

The origin of cachexia or the anorexia-cachexia syndrome (ACS) in cancer patients is multifactorial in the state of the art.

These factors include: the increased energy (glucose) uptake by tumor, the release of factors that act on satiation, being able to reduce food intake and the number of cytokines produced by the host reportedly cause metabolic abnormalities of the referred syndrome. Examples in the state of the art include: Bosaeus I, Daneryd P, Lundholm K. Dietary intake, resting energy expenditure, weight loss and survival in cancer patients. J Nutr. 2002; 132(11 Suppl):34655-34665 e Strasser F. Eating-related disorders in patients with advanced cancer. Support Care Cancer. 2003; 11(1): 11-20.

Cachexia in cancer patients can be classified into primary or secondary: Primary cachexia that is related to the metabolic effects of cancer associated to inflammatory changes. Its consequence is the progressive and often severe depletion of visceral protein, skeletal muscle and fat tissue.

Secondary cachexia is due to decreased nutrient intake and absorption, which can be caused by cancerous obstruction of the gastrointestinal tract, and also as a result of surgical, chemotherapy, radiotherapy treatments and their combinations.

Both conditions may occur concomitantly in the same patient over the course of the disease.

Anorexia Syndrome—Cachexia and Cancer Diagnosis

Malnutrition associated to weight loss induced by cancer is one of the most commonly used factors in patient assessment and for establishing a prognosis of clinical evolution.

Many studies in the state of the art indicate that patients with marked weight loss (cachexia) also show very poor therapeutic response to chemotherapy (CT), and toxicity of drugs used in patient treatment is increased.

Examples of state of the art research include: Body J J—The syndrome of anorexia-cachexia. Curr Opin. Oncol. 1999; 11(4):255-60) e ainda Tisdale M J. Cachexia in cancer patients. Nat Rev Cancer. 2002; 2(11): 862-71; Strasser F. Eating-related disorders in patients with advanced cancer. Support Care Cancer. 2003; 11(1): 11-20.

The degree of cancer cachexia is inversely correlated with the survival time of the patient and involves deterioration in quality of life and poor prognosis for patients. For examples in the state of the art, see: Argilés J M, Busquets S, Lopez-Soriano F J—Cytokines in the pathogenesis of cancer cachexia. Curr Opin Clin Nutr. Metab. Care. 2003; 6(4):401-6.) and also, Koutkia P D, Apovian C M, Blackburn G L. Nutrition support. In: Berger A M, Portenoy R K, Weissmann D E. Principles & practice of palliative care & supportive oncology. 2 ed. Philadelphia: Lippincott Willians & Wilkings; 2002. p. 933-55.

Clinical Expressions of Cachexia and Implications for the Treatment

Cachectic patients may have higher susceptibility to infectious agents, postoperative complications, reduced tolerance to cancer treatment and also pronounced drowsiness and prostration. Due to loss of muscle mass, these patients are at greater risk of developing decubitus ulcers, edema of lower limbs and intense paleness. (Costa L J M, Varella, P C S, Giglio A. Weight changes during chemotherapy for breast cancer. Rev Paul Med. (2002; 120 (4): 113-7).

Cachexia is present in more than 80% of advanced cancer patients (Inui A. Cancer anorexia-cachexia syndrome: current issues in research and management. CA Cancer J Clin. 2002; 52:72-91), (Body J J. The syndrome of anorexia-cachexia. Curr Opin Oncol. 1999; 11(4): 255-6), being responsible for a decrease of around 60% of body weight compared to the ideal weight (Argilés J M, Moore-Carrasco R, Fuster G, Busquets S, Lopez-Soriano F J. Cancer cachexia: the molecular mechanisms. Int J Biochem Cell Biol. 2003; 35(4): 405-9).

Cachexia is the main cause of death in more than 20% of cancer patients: (Inui A. Cancer anorexia-cachexia syndrome: current issues in research and management. CA Cancer J Clin. 2002; 52:72-91) and (Van Halteren H K, Bongaerts G P A, Wagener D J T H. Cancer cachexia: what is known about its etiology and what should be the current treatment approach? Anticancer Res. 2003; 23(6): 5111-6).

Anorexia-Cachexia Syndrome—Assessment Criteria

Body weight is the most commonly used nutritional parameter in patient assessment. An example of the state of the art research follows: Inui A. Cancer anorexia-cachexia syndrome: current issues in research and management. CA Cancer J Clin. 2002; 52:72-91. (e 2)

A sudden loss of weight of around 10% of body weight is considered the parameter used to establish the beginning of the anorexia-cachexia syndrome (ACS). For a state of the art example please see: Inui A. Cancer anorexia-cachexia syndrome: current issues in research and management. CA Cancer J Clin. 2002; 52:72-91.

Treatment of the Anorexia—Cachexia Syndrome—State of the Art

For explanatory purposes, without intending to limit the scope of the present invention, a brief summary of state of the art treatments available for patients with cancer-related malnutrition and cachexia and other chronic systemic diseases are presented here.

The main interventions and treatments available for the treatment of anorexia-cachexia syndrome (ACS) in chronic systemic diseases such as cancer include nutritional and pharmacological therapies that use several types of drugs, either alone or combined.

State of the Art—Anorexia-Cachexia Treatment—Nutritional Therapy

The nutritional treatment or therapy of anorexia-cachexia states is performed with the use of special nutrients, such as polyunsaturated fatty acids, eicosapentaenoic acid (EPA) and docosahexanenoic acid (DHA), the amino acids glutamine and arginine and the nucleotides used in formulations and dietary supplements.

Polyunsatured Fatty Acids (PUFAs): Eicosapentaenoic acid (EPA) and Docosahexaenoic Acid (DHA).

Eicosapentaenoic acid (EPA)[IUPAC: Acid (5Z,8Z,11Z, 14Z,17Z)-icosa-5,8,11,14,17-pentaenoic) Molecular formula ($C_{20}H_{30}O_2$), CAS (1553-41-9)].

The eicosapentaenoic acid (EPA or also icosapentaenoic is an omega-3($\omega$-3) polyunsaturated fatty acid (PUFa).

It is a substance that acts by inhibiting the cyclo-oxigenase enzyme. It has been found to help to control weight loss in patients with pancreatic cancer, stabilize protein reserves and fat tissue. This result is followed by the temporary decrease, during the acute phase, in protein synthesis, and energy loss control.

This fatty acid is reported in the state of the art as being able to mitigate the action of catabolic factors in cancer-induced cachexia. Its administration leads to the statistically significant reduction in protein degradation. These results have recommended the eicosapentaenoic acid in the dual role of anti-cancer and anti-cachectic agent in clinical studies. For an example of state of the art research, please see: Beck A S, Smith K L, Tildale M J. Anticachectic and antitumor effect of eicosapentainoic acid and its effect on protein turnover. Cancer Res. 1991; 51:6089-93.

Docosahexaenoic Acid (DHA): [IUPAC: (acid 4Z,7Z,10Z,13Z,16Z, 19Z-docosa-4,7,10,13,16,19-hexaenoic), Molecular formula: (C22H32O2), CAS (6217-54-5)].

The docosahexaenoic acid (DHA) is also considered an omega-3 fatty acid.

The DHA and its metabolites act on the body because of their association with the arachidonic acid (arachidonic acid [IUPAC: eiscosatetraenoic acid cis-5-cis-8-cis-1 1-cis-14)].

Both compounds (EPA, DHA) have been associated to decrease in cancer volume, weight loss improvement and decrease in anorexia, due to its anti-inflammatory action. Examples of the state of the art research include: Abcouwer S F, Souba W W. Glutamina e arginina. In: Shils M E, Olson J A, Shike M, Ross A C. Tratado de Nutrição Moderna na Saúde e na Doença. 9ª ed. São Paulo: Manole; 2003. p. 597-608).

According to some authors, the mechanism of reversion of cachexia by EPA consists in the suppression of inflammatory cytokines such as TNFα, IL-1 and IL-6. Examples of state of the art research include (Body J J. The syndrome of anorexia-cachexia. Curr Opin Oncol. 1999; 11(4): 255-60) and (Tisdale M J. The 'Cancer Cachectic Factor'. Support Care Cancer. 2003; 11(2): 73-8) and (Van Halteren H K, Bongaerts G P A, Wagener D J T H. Cancer cachexia: what is known about its etiology and what should be the current treatment approach? Anticancer Res. 2003; 23(6): 5111-6).

Clinical study involving dietary supplementation in cancer patients with PUFAs, using capsules of fish oil containing 18% of EPA and 12% DHA for 3 months. The results of this test showed decrease in fatigue, reduction of acute phase proteins, and weight gain. Reduction of acute phase proteins (C reactive protein) was associated to suppression in IL-6 production (Inui A. Cancer anorexia-cachexia syndrome: current issues in research and management. CA Cancer J Clin. 2002; 52:72-91).

Glutamine and Arginine: The amino-acids glutamine (GLN) and arginine (ARG) are used as supplementation in nutritional therapy, as components of several nutritious formulas. In the state of the art, there are reports associating the use of glutamine with greater preservation of the skeletal muscle, because of increased protein synthesis and reduction in muscle proteolysis (59, 64, 107,108.).

Moreover, glutamine improves the nitrogen balance in critically ill patients (Abcouwer S F, Souba W W. Glutamina e arginina. In: Shils M E, Olson J A, Shike M, Ross A C. Tratado de Nutrição Moderna na Saúde e na Doença. 9ª ed. São Paulo: Manole; 2003. p. 597-608), increases the function of immune cells without increasing the production of proinflammatory cytokines (Waitzberg D L, Lotierzo P H P, Duarte, A J S, Schronts E P, Silva M P N-Revista Brasileira de Cancerologia 2006; 52(1): 59-7777 Cerra F. Imunonutrição. In: Waitzberg D L. Nutrição Oral, Enteral e Parenteral na Prática Clínica. 3ª ed. São Paulo: Atheneu; 2000. p. 1511-38.).

It is also precursor of glutathione, an important intracellular antioxidant. An example follows: Abcouwer S F, Souba W W. Glutamina e arginina. In: Shils M E, Olson J A, Shike M, Ross A C. Tratado de Nutrição Moderna na Saúde e na Doença. 9ª ed. São Paulo: Manole; 2003. p. (597-608.) and also; Correa E C M, Rocha R O. Nutrientes especiais e câncer. In: Waitzberg D L. Dieta, Nutrição e Câncer. São Paulo: Atheneu; 2004. p. (638-44.)

According to Abcouwer & Souba (2003), supplementation with glutamine (GLN) can help mitigate muscle depletion, reducing protein catabolism associated to cancer cachexia. Examples of the state of the art research include: Abcouwer S F, Souba W W. Glutamina e arginina. In: Shils M E, Olson J A, Shike M, Ross A C. Tratado de Nutrição Moderna na Saúde e na Doença. 9ª ed. São Paulo: Manole; 2003. p. 597-608.

Increased radiotherapy and chemotherapy tolerance was also observed following supplementation, as a result of the protection provided by glutamine against intestinal injury and treatment toxicity, as this amino-acid is a source of energy for cells of the small intestine and lymphocytes, being important for the proliferation of these cells and preservation of these tissues, preventing intestinal atrophy, preserving the immunity of the intestinal mucosa and improving T-cell-mediate immune response, and, thus, stimulating the body's immune function as a whole. For examples of state of the art research, see: Frenhani P B. Terapia nutricional em estados hipermetabólicos. Rev Nutr em Pauta. 2003; 11(60): 40-6 and also Waitzberg D L, Lotierzo P H P, Duarte, A J S, Schronts E P, Silva M P N; 52(1): 59-7777 Cerra F. Imunonutrição. In: Waitzberg D L. Nutrição Oral, Enteral e Parenteral na Prática Clínica. 3ª ed. São Paulo: Atheneu; 2000. p. 1511-38).

Arginine (ARG), another amino-acid of high nutritional importance in catabolic states is involved in protein synthesis, biosynthesis of amino acids and their derivatives and higher nitrogen retention. Examples of the state of the art research include: Abcouwer S F, Souba W W. Glutamina e arginina and Shils M E, Olson J A, Shike M, Ross A C. Tratado de Nutrição Moderna na Saúde e na Doença. 9ª ed. São Paulo: Manole; 2003. p. (597-608)

In the state of the art, its use has been associated with increased activation of T lymphocytes in cancer patients, stimulating both the proliferation and function of T lymphocytes. Examples of the state of the art research include: Waitzberg D L, Lotierzo P H P, Duarte, A J S, Schronts E P Cerra F. Imunonutrição. In: Waitzberg D L. Nutrição Oral, Enteral e Parenteral na Prática Clínica. 3a ed. São Paulo: Atheneu; 2000. p. 1511-38.) 109.

Because it is an aminoacid precursor of nitric oxide, it acts as a cytotoxic effector molecule, promoting tumor growth retardation. For examples of state of the art research, please see: Koutkia P D, Apovian C M, Blackburn G L. Nutrition-support. In: Berger A M, Portenoy R K, Weissmann D E in Principles & practice of palliative care & supportive oncology. 2 ed. Philadelphia: Lippincott Willians & Wilkings; 2002. p. 933-55.).

According to Méier et al (2004), rats fed with ARG showed reduction in tumor progression and dissemination. The high levels of nitric oxide generated by ARG resulted in apoptosis and tumor growth inhibition in pancreatic tumors in vivo and in vitro. In animals with solid tumor receiving supplementation with 4 to 6% ARG, the rate of metastases was lower and anemia was less severe than in those animals that were not given ARG in their diet. Examples of the state of the art research include: Meier R, Steuerwald M, Waitzberg D L. Imunonutrição em cancer. In: Waitzberg D L. Dieta, nutrição e câncer. São Paulo: Atheneu; 2004. pp. 630-7.

State of the Art—Anorexia-Cachexia Treatment—Available Drugs

There are some drugs used for the palliative treatment of anorexia-cachexia syndrome in the state of the art, and for purposes of explanation only, megestrol acetate, corticosteroids, dronabinol, melatonin, ibuprofen, eicosaminopentoic acid, hydrazine sulfate and also the human growth hormone (somatropin).

Megestrol acetate [-IUPAC (17-Acetyl-17-hydroxy-6,10,13-trimethyl-2,8,9,11,12,14,15,16-octahidro-1H-cyclopenta[a]phenanthren-3-one) CAS 3562-63-8, Molecular formula (C24H32O4) ATC (G03AC05, G03DB02, L02AB0), PubChem (19090) DrugBank (APRD01092)].

The megestrol acetate is a synthetic progesterone derivative. This drug is often used (orally) to treat advanced cancers, cancers responsive to hormone therapy and in the treatment of patients with malnutrition-cachexia syndrome.

In the state of the art, there is a report of the use of the association of medroxyprogesterone acetate with chemotherapy adjuvant in patients with head and neck cancer. Stimulation of appetite and weight gain, improvement of quality of life indicators and decreased serum levels of Interleukin 2 and Interleukin 6 (Mantovani G, Macció A, Bianchi A, Curreli L, Ghiani M, Santona M C, Del Giacco G S, Megestrol acetate in neoplasic anorexia/cachexia: clinical evaluation na comparison with cytokine levels in patients with head and neck carcinoma treated with neoadjuvant chemotherapy. Int. J. Clin. Lab. Res. 1995; 25:135-141).

Its clinical use has been associated to episodes of adrenal insufficiency. Examples in the state of the art research include: Bulchandani D, Nachnani J, Amin A, May J (August 2008). "Megestrol acetate-associated adrenal insufficiency". Am J Geriatr Pharmacother 6 (3): 167-72. doi:10.1016/j.amjopharm.2008.08.004.

Corticosteroids (Glucocorticoids)—They have been used as palliative treatment of symptoms associated with cancer. They improve, in the short term, appetite, food intake, performance and quality of life of patients, but do not ensure weight gain.

Prolonged treatment with corticosteroids, however, may lead to weakness, osteoporosis and immunosuppression, which can be harmful to cancer patients, since it increases the risk of infection and the evolution of the underlying disease.

Dronabinol [IUPAC (−)-(6aR,10aR)-6,6,9-trimethyl-3-pentyl-6a, 7,8,10a-tetrahydro-6H-benzo[c]chromen-1-ol.), CAS 1972-08-3, ATC (A04AD10),
PubChem (16078)]. It is a synthetic derivative of *Cannabis sativa* L. in the oral form of tetrahydrocannabinol (THC). Has been used as antiemetic in chemotherapy treatments.

Many studies associate the use of THC as adjuvant in the treatment of cancer patients, with improvement of mood and stimulation of appetite, as well as weight gain. In 1986, dronabinol was approved by the FDA for the treatment of anorexia in AIDS patients and for treating nausea and vomiting in patients undergoing chemotherapy.

Ibuprofen [IUPAC: Acid (RS)-2-[4-(2-methyl-propyl)phenyl]propanoic) Molecular formula: C13H18O2. CAS (15687-27-1), ATC (M01AE01), PubChem (3672) DrugBank (APRD00372)].

Ibuprofen is a non-steroidal anti-inflammatory drug (NSAIDs). It inhibits cyclo-oxygenases and the consequent formation of proinflammatory mediators.

One reported effect of Ibuprofen is the reduction of energy expenditure in patients with pancreatic cancer, suggesting its possible role in the stabilization of the cachectic process, which contributes to weight loss in cancer patients, according to Tisdale M J. Biology of Cachexia. JNCI 1997; 89:1763-73, cited as an example of state of the art research.

Hydrazine sulfate—IUPAC (Hydrazine) Molecular formula (H6N2O4S). CAS (10034-93-2) PubChem (24842).

It is an inhibitor of the phosphoenolpyruvate carboxylase enzyme. Reports in the state of the art demonstrate its beneficial influence in patients with neoplastic cachexia, with weight maintenance or even gain. (Tisdale M J. Biology of Cachexia. JNCI 1997; 89:1763-73.

For other examples of the state of the art, please see: Chlebowski R T, Bulcavage L, Grosvenor M, et al.: Hydrazine sulfate in cancer patients with weight loss. A placebo-controlled clinical experience. Cancer 59 (3): 406-10, 1987, and Loprinzi C L, Goldberg R M, Su J Q, et al.: Placebo-controlled trial of hydrazine sulfate in patients with newly diagnosed non-small-cell lung cancer. J Clin Oncol 12 (6): 1126-9 1994.

Melatonin [IUPAC: (N-[2-(5-methoxy-1H-indolo-3-ilo)etilo]ethanamide) Molecular formula: C13H16N2O2 CAS (73-31-4), ATC (N05CM17), PubChem (896), DrugBank (APRD00742)].

Melatonin is a hormone produced in more complex animals by the pineal gland, which can reduce the circulating levels of the Tumor Necrosis Factor alpha (TNF-alfa) in advanced cancer patients. Its clinical use has been associated to reduction of myelosuppression, neuropathy and cachexia in patients with poor clinical conditions with lung cancer.

Somatropin (Recombinant somatropin) [IUPAC: (Human growth hormone), Molecular formula: C990H1532N262O300S7, CAS (12629-01-5), DrugBank (DB00052]. This human growth hormone has anabolic properties and was approved by the FDA for the treatment of the anorexia-cachexia syndrome in patients with AIDS and other chronic diseases, aimed at weight and muscle mass gain.

Other Clinical Complications Associated to Chronic Systemic Diseases and Also to Treatments—Febrile Neutropenia Associated to Chemotherapy and Other Treatments—State of the Art Neutrophils are cells in the blood that constitute the first line of defense of the body, participating in the body's defense system, in the presence of infections, particularly bacterial, and tissue lesions. These cells contain granules with proteolytic enzymes that participate in the digestion of antigens.

The so-called neutropenia is clinically characterized by reduction in the number of neutrophils in periferal blood below their normal values.

Neutropenia is usually defined, in adults and children over one year as the decrease in the number of circulating neutrophils to an absolute cell count below 1.500/mm3 in white individuals and 1.000/mm3 in black individuals. Neutropenias are classified into discrete (1.000 to 1.500 cells/mm3), moderate (500 to 1.000 cells/mm3) and severe (lower than 500 cells/mm3).

Exposure to drugs is one of the most common factors that cause neutropenia. Several drugs may cause neutropenia such as painkillers, antibiotics, anti-inflammatory, antidepressant, anti-thyroid, cardiovascular and cytotoxic drugs, among others.

Neutropenia associated to drugs and other treatments are events particularly damaging to patients with chronic systemic diseases, such as cancer, because they pave the way for infections caused by opportunistic pathogens.

Additionally, in order to fight opportunistic infections, the use of various methods of treatment and control of these infectious agents is required, particularly antibiotics in high doses, which besides being expensive, may not provide an effective alternative.

Due to the reduction in the number of neutrophils or the limiting in their action, many patients undergoing cancer treatment present clinical pictures of febrile neutropenia, with or without the presence of an identifiable infectious focus.

Febrile neutropenia is a serious complication often induced by the use of cytotoxic agents commonly used in the treatment of cancer and other conditions. Febrile neutropenia is defined as a fever of 38° C. or more maintained for over an hour associated to an absolute count of cells lower than 500/mm3.

Its occurrence associated to cancer chemotherapy may have a negative impact on treatment adherence and on the quality of life of patients.

According to recommendations of the American Society of Clinical Oncology, the incidence of severe neutropenia (neutrophil count below 500/mm3) varies according to the chemotherapy regimen adopted. For an example in state of the art research, see: Smitth T J et al, Update of recommendations for the use of white blood cell growth factors: an evidence-based clinical practice guideline. J Clin Oncol. 2006; 24(19): 3187-205. Epub 2006 May 8.

Treatment of Neutropenia Caused by Cytotoxic Treatments—State of the Art

Neutropenia associated or caused by compounds and/or cytotoxic treatments is considered one of the main problems in the treatment of cancer patients due to their potential for triggering various medical complications, ranging from deterioration in the quality of life of patients to episodes of septicemia and death.

Many compounds used in cancer treatment is associated to significant cytotoxic effects on neutrophils, peripheral blood cell elements that represent the first line of defense of immune response, and, thus, patients receiving cytotoxic chemotherapy have often a decreased immune function and are at higher risk of infection. For an example of state of the art see: Crawford J, Dale D C, Lyman G H. Chemotherapy-induced neutropenia: risks, consequences, and new directions for its management. Cancer 2004; 100:228-237.

Although there are cases of patients with neutropenia associated to the administration of chemotherapy that remain asymptomatic, many patients may experience complications resulting from immunosuppression caused by cytotoxic agents commonly used in chemotherapy, such as fever and infection that may require hospitalization.

The most commonly used treatment is intravenous antibiotic therapy to reduce the risk of opportunistic infections that may lead to septicemia. For an example of state of the art research, see: Over H. New directions in the management of chemotherapy-induced neutropenia: risk models, special populations, and quality of life. Semen Oncol 2003; 30(supple 13):18-23. [145087] and (Schimpff S, Satterlee W, Young V M, Serpick A. Empiric therapy with carbenicillin and gentamicin for febrile patients with cancer and granulocytopenia. N Engl J Med 1971; 284:1061-1065.

One relatively recent therapy in the state of the art to treat neutropenia associated to treatments with cytotoxic drugs is the use of the so-called growth factors of the myeloid lineage (G-CSF and GM-CSF), which are cytokines that regulate proliferation, differentiation and functional activation of hematopoietic cells in the bone marrow. For an example in state of the art research, please see: Valley A W. New treatment options for managing chemotherapy-induced neutropenia. Am J Health Syst Pharm 2002; 59: S11-S6.

They are also the cytokines most commonly used for reconstitution of the myeloid series, jointly or sequentially to chemotherapy and radiotherapy treatments, being incontestable in the state of the art its importance for this therapeutic purpose.

They are also extensively used in the state of the art in surgeries that involve the implantation of stem cells and bone marrow cells, for reconstitution of the myeloid series.

Besides their use as stimulants of the myeloid series, experimental data suggest they are also effective when used as adjuvant therapy in patients with melanoma, contributing to the significant increase in survival time and in the time period between cancer recurrences. For an example of state of the art research, see: Spitler L E, Grossbard M L, Ernstoff M S, et al. Adjuvant therapy of stage III and IV malignant melanoma using granulocyte-macrophage colony-stimulating factor. J Clin Oncol. 2000; 18:1614-1621.

They are produced using cell culture technique and other methods. For an example of state of the art see: U.S. Pat. No. 6,020,169—Production of secreted foreign polypeptides in plant cell culture.

Growth Factors of the Myeloid Lineage—Main Products Available in the State of the Art Filgrastim [IUPAC (Human granulocyte macrophage colony stimulating factor). Molecular formula ($C_{845}H_{1343}N_{223}O_{243}59$) CAS (143011-72-7) ATC (L03AA02) PubChem (not available) DrugBank (BTD00072)].

Sargramostim [IUPAC (Human granulocyte macrophage colony stimulating factor) Molecular formula ($C_{639}H_{1006}N_{168}O_{196}58$) CAS (83869-56-1) ATC (L03AA09) PubChem (not available) DrugBank (BTD00035)].

The main adverse side effects related to their use reported in the state of the art are bone pain, varying from mild to intense, and also cases of abnormal proliferation of leukocyte cells, which can lead to discontinuation of treatment.

Problems Associated to Chronic Systemic Diseases and their Treatment—Need for New Therapies and Improvements—General Description of the Present Invention In view of the aforesaid, it is evident for any expert with knowledge of the state of the art, that new compounds and/or new combinations of drugs or therapies to treat chronic systemic diseases, such as cancer, and also the clinical complications associated to the primary disease (cancer), such as cachexia, and finally the adverse side effects related to the current drugs and treatments should be produced and made available on an ongoing basis.

This is the case of the present invention, that is, it is intended for the preventive, curative or palliative treatment of chronic systemic diseases, such as cancer, enhancing the therapeutic effectiveness of several classes of drugs and other treatments, and additionally, in an innovative way, can be used concomitantly for treating important clinical problems associated to the primary disease and/or caused or aggravated by the use of other drugs or treatments.

The main issues involved in the treatment of systemic diseases, such as cancer, are listed and discussed below, and detailed explanation of the state of the art related to the present invention, as well as indications of the innovative activity involved are provided.

Any animal species can benefit from the present invention. Although the main purpose or intended field of application of the present invention is the treatment of human beings, the invention and its practical use cannot be limited to this species.

No further knowledge or technical expertise is required to the full understanding and use of the present invention.

From the State of the Art to the Present Invention

In the state of the art, the immunomodulator or biological response modifier called proteic aggregate of ammonium and magnesium phospholinoleate-palmitoleate anhydride, when used alone, is known to have significant antitumor effects in several animal models in cancer research, such as the Walker 256 carcinoma, Ehrlich ascites tumor, breast carcinoma and plasmacytoma. (PI 0305373-3, U.S. Ser. No. 10/978,683 and EPA 0426250.3.2405), though not being able, when used alone, to obtain regression of tumor in all cases, as it occurs with the other drugs and treatments described in the state of the art.

In the state of the art, the referred compound (proteic aggregate of ammonium and magnesium phospholinoleate-palmitoleate anhydride) is also known to produce effects on the immune system in experimental animals with various types of cancer, with the production of effector cytokines typical of a TH-1 (IL-2, IFN-gamma) type immune response in PI—0305373-3 U.S. Ser. No. 10/978,683 and EPA 0426250.3.2405, with the use of a compound named proteic aggregate of ammonium and magnesium phospholinoleate palmitoleate anhydride alone.

In PI—0305373-3 U.S. Ser. No. 10/978,683 and EPA 0426250.3.2405 lymphocyte proliferation and increased NK cell activity are described in animals with tumors as a result of induction of a TH-1 type immune response, with the use of the biological response modifier (proteic aggregate of ammonium and magnesium phospholinoleate-palmitoleate anhydride) alone.

Finally, in the state of the art, the referred compound (proteic aggregate of ammonium and magnesium phospholinoleate-palmitoleate anhydride) is known for its ability not only to induce a TH-1 type immune response with stimulation of endogenous production of effector cytokines typical of such an immune response, as the interferon-gamma (IFN-gamma) and the interleukin-2 (IL-2), but also, when used in combination with other drugs, that is, as an element of a combination antimicrobial therapy, or else as a component in the manufacture of new drugs or drug combinations, it maximizes the antimicrobial action of the referred drug association or combination, creating a synergistic action wider than the biological properties of the isolated components, when it is used to treat infections caused by opportunistic pathogenic microorganisms (PI 0801803-0 and WO/2009/097670).

The same ability to stimulate or cause a TH-1 type immune response with the production of the referred effector cytokines (IFN-gamma, IL-2) is considered in the state of the art in medicine important to fight invasive microorganisms. The referred immune response (TH-1 type immune response) that can be natural or stimulated by some agents or compounds, such as biological response modifiers is also considered particularly useful in the elimination and/or control of tumors and neoplastic processes.

In the state of the art, there are several reports of experiments in animals, and also of therapeutic strategies with cytokines such as IL-2 and Interferons, obtained from exogenous sources, which are used in human beings, in routine clinical practice, aimed to cause or induce a TH-1 type immune response to fight tumors or metastases in cancer patients.

For an example of state of the art research, please see: Rosenberg S A, Packard B S, Aebersold P M, Solomon D, Topalian S L, Toy S T, et al. The use of tumor-infiltrating lymphocytes and interleukin-2 in the immunotherapy of patients with metastatic melanoma. A preliminary report N Engl J Med 1988; 319: 1676-8.

For another example of the state of the art using exogenous Interferon as a biological response modifier to stimulate a TH-1 type immune response in cancer treatment, associated with BCG vaccine: Yi Luo, Xiaohong Chen, Tracy M. Downs, William C. DeWolf and Michael A. O'Donnell—IFN-2B Enhances Th1 Cytokine Responses in Bladder Cancer Patients Receiving *Mycobacterium bovis* Bacillus Calmette-Guérin Immunotherapy—The Journal of Immunology, 1999, 162: 2399-2405.

However, in the state of the art it is known that the use of exogenous cytokines such as Interferons and 1-2 and IL-12, despite their significant therapeutic potential for use alone or as adjuvant immunotherapy drugs when associated to other compounds or combined to other compounds and/or treatments to maximize antineoplastic effects, in order to treat cancer patients, has practical disadvantages, particularly because of their high toxicity levels. For an example in the state of the art, please see: Zona Wang et al., Combined IL-12 and GM-CSF gene therapy for murine hepatocellular carcinoma, Cancer Gene Therapy (2001) 8, 751-758.

In order to overcome or minimize the problems that commonly occur in the use of adjuvant immunotherapy, that is, when exogenous cytokines are used to treat severe chronic diseases, such as cancer, without compromising the efficiency or usefulness of these substances in the treatment of cancer patients, an innovative and inventive solution can be created and made available through the use of products and compounds that are also able to mobilize and/or stimulate the endogenous or physiological production of such compounds in the body, such as the interferons and the interleukins, preferably without additional toxicity, maintaining these properties in the presence of the cancer process.

This compound is available in the state of the art and is called proteic aggregate of ammonium and magnesium phospholinoleate-palmitoleate anhydride described in PI—0305373-3, PI 0801803-0, U.S. Ser. No. 10/978,683, EPA 0426250.3.2405, and WO/2009/097670, classified as a biological response modifier or immunomodulator because of its ability to act in the immune system.

Thus, it has been specially selected as a useful component of the present invention, which shall play a role similar to that of exogenous cytokines, such as the several types of interferons (IFN-alpha, IFN-beta, IFN-gamma), interleukin-2 (IL-2) and interleukin-12 (IL-12) used in the state of the art as anticancer drugs and/or immunotherapy adjuvants, that is, as effector substances required to trigger an immune response in the patient, in order to enable, restore or enhance the patient's immune system, so that it can efficiently fight or control chronic systemic diseases, such as cancer.

Exogenous cytokines, such as the interferons and interleukins (IL-12, IL-2), among others, are routinely used alone, or, as it is more common in the state of the art, in association or combination with other chemotherapy drugs to maximize the therapeutic effect in the treatment of chronic systemic diseases, such as cancer, though its use alone or in combination with other drugs has some practical disadvantages because of their high toxicity levels. This type of therapeutic strategy is called adjuvant immunotherapy.

The present invention also uses a therapeutic strategy that can be generally described, according to the state of the art in medicine, as a kind of adjuvant immunotherapy. In a different and entirely innovative way, however, the present invention, instead of using exogenous or external cytokines, shall use the patient's body ability to induce an immune response to fight the disease, by stimulating endogenous production of TH-1 effector cytokines that trigger an immune response.

This shall be made possible by the deliberate use of a biological response modifier (proteic aggregate of ammonium and magnesium phospholinoleate-palmitoleate anhydride) specially selected for use in the present invention as the fixed component of a new association or combination of drugs and/or treatments, providing remarkable therapeutic and economic advantages for this new combination or association, as will be detailed in the present report, such benefits being similar to those that would be possible with the use of exogenous cytokines, without facing the problems posed by the use of these exogenous substances.

Therefore, based on this body of knowledge, in the present invention a component specially selected for use in this invention will be associated and/or combined to other drugs and/or treatments, because this compound named in the state of the art as a proteic aggregate of ammonium and magnesium phospholinoleate-palmitoleate anhydride has, among other properties of great interest to the present invention, the ability to produce or stimulate the endogenous production of such effector cytokines that trigger a TH-1 type immune response, considered fundamental in the state of the art for cancer treatment.

Additionally, according to the purpose of the present invention, a new association or combination of drugs and/or treatments of which is part the biological response modifier (proteic aggregate of ammonium and magnesium phospholinoleate-palmitoleate anhydride), will not only provide a new therapeutic association or combination with medicinal or therapeutic properties distinct from and wider than the properties of the isolated components, but will also allow correction of additional clinical problems associated to the primary disease (cancer) and problems caused by the use of other components of the therapeutic association or combination, which is substantially different from any previous reference to the biological response modifier (proteic aggregate of ammonium and magnesium phospholinoleate-palmitoleate anhydride) or any association or combination described in the state of the art, as shall be detailed in this report, with examples of practical use.

Benefits of the use of the present invention: Since the therapeutic effectiveness of the association or combination of drugs and/or treatments that characterize the present invention can be maximized or increased, with the presence in the association or combination of the specially selected biological response modifier (proteic aggregate of ammonium and magnesium phospholinoleate-palmitoleate anhydride), one important consequence is that, depending on the occasion or patient's condition, lower doses or longer intervals can be considered for the use of other drugs and/or treatments selected for the association or combination, particularly when the therapeutic options to be use consist in drugs and/or treatments known to cause cytotoxic or debilitating effects that impact the patient's general condition of quality of life.

Since the toxicity of any drug or treatment that can harm the body as a whole or its components is directly related to the magnitude of the doses used and the duration of treatment, the minimization of adverse side effects and/or its intensity or frequency can be obtained either by the minimization of the required quantities of such other drugs and treatments or by providing a longer period of time for their use, which is made possible by the present invention, as shall be demonstrated in this report, with examples of practical use.

Another benefit provided by the present invention is that it allows the use of higher doses or more intensive regimens than those allowed with other cytotoxic drugs or treatments to be selected for use in association or combination, if needed. This shall occur because of the remarkable ability of the biological response modifier selected as a key component of the present invention (proteic aggregate of ammonium and magnesium phospholinoleate-palmitoleate anhydride) to reverse and/or minimize some of the most harmful effects of such compounds and/or treatments, when present in the combination or association of drugs and treatments described in the invention, as shall be exposed in this report, with examples of practical use.

Many times the need to reduce doses or periods of drug treatments and/or treatments due to the occurrence of side effects directly or indirectly related, mainly to myelosuppression, as shall be detailed in the present report, constitutes a factor that may contribute to the failure of treatments and the invention, and the maximization of the effect of all components of the association or combination made possible by the properties of this invention, shall provide any expert with knowledge of the state of the art with the advantageous option of reducing the doses of drugs, according to the case and the clinical situation involved.

Inversely, in cancer treatment higher doses or more intensive regimens are often necessary to maximize the effect of the drugs or treatments. In both situations, the use of the invention with its unique and amazing features may be feasible and useful, representing a considerable improvement in the state of the art compared to the existing therapeutic options or modalities.

The toxicity of the biological response modifier specifically selected as a key component of the present invention (proteic aggregate of ammonium and magnesium phospholinoleate-palmitoleate anhydride) is negligible, even at higher doses and does not interfere negatively with the other components, either drugs and/or treatments used in the combination or association, as reported by preclinical and clinical studies, and also according to supplementary data that shall be provided in this report, that is, its use as a key component of the present invention shall not cause any additional toxicity or adverse side effect.

The cited compound (proteic aggregate of ammonium and magnesium phospholinoleate-palmitoleate anhydride), which is a key component of the present invention has already been tested in toxicological studies in the state of the art, with the use of several animal species, including rodents, dogs, nonhuman primates, as well as in clinical trials with human patients, and has not shown any significant toxicity that might discourage its use. For a more recent example in the state of the art, please see: Duran N, Nunes I. et al, A biotechnological product and its potential as a new immunomodulator for treatment of animal phlebovirus infection: Punta Toro vírus—Antiviral Research, Volume 83, Issue 2, August 2009, Pages 143-147.

Absolute Novelty of the Present Invention

Analysis of the information already provided, and more data and relevant examples will be included in this report, shows that the present invention is a novelty and substantially differs from the any therapies and strategies in the state of the art, including any previous reference to the compound called proteic aggregate of ammonium and magnesium phospholinoleate-palmitoleate anhydride (PI 0305373-3, U.S. Ser. No. 10/978,683 e EPA 0426250.3.2405, PI 0801803-0 and WO/2009/097670), or any other claim or communication that has unequivocally presented a combination or association of drugs and treatments with the same purposes of the present invention, that is:

An association or combination of compounds and/or treatments comprising essentially the use of a biological response modifier (proteic aggregate of ammonium and magnesium phospholinoleate-palmitoleate anhydride) in association and/or combination with other drugs and/or treatments, for use in the preventive, curative or palliative treatment of chronic systemic diseases, such as cancer, which also allows reversion or minimization of other clinical problems associated to the primary disease and finally the correction and/or minimization of adverse side effects of the other drugs and/or treatments, as a practical outcome of its use.

Innovative and Integrated Solution for the Main Problems in the Treatment of Chronic Systemic Diseases, Such as Cancer The present invention represents or provides, thus, an association or combination of drugs and/or treatments that expresses or results in practice in a set of novel medicinal effects in the state of the art, for the preventive, curative or palliative treatment of chronic systemic diseases, such as cancer, other clinical complications associated and also deficiencies or unwanted side effects of the treatments of these diseases, as shall be detailed in this report, with examples of practical use.

Several aspects related to the treatment of chronic systemic diseases, such as cancer, are described below, which are important for the understanding of the present invention and the level of inventive activity involved, which can be understood by any expert with knowledge of the state of the art, without the need for further explanations:

(A)—The main existing treatments for chronic diseases, such as cancer, are not fully effective to ensure preventive or curative healing, (B)—In order to maximize the chances of success of the treatment of chronic diseases, such as cancer, chemotherapy treatments or protocols involving several drugs, and also treatment protocols involving, for example, the use of drugs and non-drug procedures in combination or association are widely used in the state of the art.

(C)—Chronic systemic diseases, such as cancer, are often preceded and/or followed by malfunctioning or compromised immune system and/or of its important components and/or functions.

(D)—The treatments of these diseases, such as chemotherapy and radiotherapy often suppress the immune system and/or negatively impact the functionality of its components, causing e.g. reduction or destruction of bone marrow stem cells, which is expressed in the amount and functionality of peripheral white blood cells, such as lymphocytes and neutrophils.

(E)—Adverse clinical conditions associated to the primary disease, such as cachexia or anorexia-cachexia syndrome, characterized by weight loss and accelerated depletion of muscle and fat tissue by most sufferers of chronic systemic diseases, such as cancer, are common findings in cancer patients and be aggravated by existing treatments against cancer in the state of the art.

Ideal Characteristics of a New Treatment: The Invention Possesses all Desirable Characteristics for the Treatment of Chronic Systemic Diseases (Cancer)

Considering all these aspects, it would be highly desirable and innovative that a treatment or drug for chronic systemic diseases, such as cancer, meets all these needs, as follows:

1) Increase the effectiveness or success rate of the existing drugs and/or treatments, 2) Recover or increase the effectiveness of the immune system and/or functionality of its components impaired by the disease, 3) Counteract or reduce the incidence or severity of side effects on cells of the immune system caused by the use of other drugs or treatments, 4) Act in a preventive, curative or palliative way regarding the important adverse clinical condition associated to these diseases and/or aggravated by the other drugs and/or treatments called cachexia, 5) Substantially improve the quality of life of patients.

The present invention consists precisely in a new combination of drugs and/or treatments which in a remarkable and innovative way, satisfies all the requirements of the aforementioned five ideal features of a new treatment, that is, those listed in items 1, 2, 3, 4 and 5.

Satisfaction of all these requirements or features was obtained in the invention, as it shall be demonstrated in the present report, with the use of the biological properties of the immunomodulator (proteic aggregate of ammonium and magnesium phospholinoleate-palmitoleate anhydride), which were combined in an innovative way with the therapeutic properties of other existing drugs and/or treatments, and, in a remarkable way, can maximize the therapeutic effect of the association or combination, eliminate or minimize suppression of the immune system often associated to the existing treatments, reverse or minimize primary and secondary cachexia and consequently improve the quality of life of patients.

The inventive activity consisted of a procedure for the creation of new therapeutic solutions that were both practical and feasible to face the challenges involved in the treatment of chronic systemic diseases, such as cancer. It started with the identification of the needs and difficulties associated to the treatment of these diseases, combined with the assessment of the therapeutic properties of drugs and treatments, and of the disadvantages of the drugs and treatments for such diseases available in the state of the art and the search for ways of overcoming or minimizing these shortcomings.

Following the identification of the deficiencies in the state of the art for the treatment of chronic systemic diseases, such as cancer, a combination of drugs and treatments aimed to solve or mitigate these deficiencies was deliberately designed, using new information and scientific data on the specific biological response modifier (proteic aggregate of ammonium and magnesium phospholinoleate-palmitoleate anhydride), not described until now in the state of art. Thus, the new information and scientific data on the above mentioned compound were combined with knowledge on the biological and therapeutic properties of the other compounds and/or treatments available for treatment of cancer and comorbities, resulting in an innovative association or combination of drugs and treatments that, after its elaboration, was tested in animal models and human beings, as shall be exposed in the present report.

For the purposes of the present invention, the biological and therapeutic properties of the biological response modifier (proteic aggregate of ammonium and magnesium phospholinoleate-palmitoleate anhydride), are added to the biological and therapeutic properties of the other drugs and/or treatments, when used in association or combination, creating a synergistic action wider than the biological properties of the isolated components Concomitantly and surprisingly, as shall be detailed in the present report, the use of the biological response modifier (proteic aggregate of ammonium and magnesium phospholinoleate-palmitoleate anhydride), specially selected for the present invention shall provide a remarkable contribution to reverse or minimize other symptoms and clinical pictures associated to the disease, such as cachexia, and in na innovative way will make it possible to reverse or minimize unwanted side effects on the immune system or its components used in association or combination, aimed to improve the general condition of the patient, positively impacting their quality of life.

That is, the outcome or the practical effect of the invention, or else, of the association of combination of several classes of medications and modalities of treatments available in the state of the art with the use of the biological response modifier (proteic aggregate of ammonium and magnesium phospholinoleate-palmitoleate anhydride), specifically selected for use as a key component and always present in any association or combination with these other elements, not only will have wider therapeutic effectiveness than any of its components individually considered, but will also make it possible to correct or minimize important adverse side effects of the other components that create obstacles to their use alone, as shall be shown in this report.

The present invention, a new association or combination of drugs and/or treatments that uses specifically the biological response modifier called in the state of the art proteic aggregate of ammonium and magnesium phospholinoleate-palmitoleate anhydride with other drugs and/or treatments for chronic systemic diseases, such as cancer, with the deliberate purpose of maximizing the therapeutic effectiveness of the association and also reverse or minimize immunosuppression or loss of functionality of the immune system and/or of any of its components, and finally treat, in an effective way, another clinical problem typical of this type of disorder (cachexia), either it is caused by the base disease and/or aggravated by other treatments, with strong positive impact on the quality of life of users, has not been described in the state of the art until now with these unique and remarkable characteristics and properties.

Although the invention uses components of several classes and types of drugs and/or treatments already known in the state of the art, it allows to obtain new effects for these drugs and/or treatments, when associated or combined, that have not been described in the state of the art until now, that is, possessing much more powerful therapeutic properties completely different than one might expect to obtain with the isolated use of its components, and which can be understood by any expert with knowledge of the state of the art, particularly after the explanations contained in the present report and the practical examples to be provided.

For explanatory purposes, it can be said that the role of the biological response modifier called in the state of the art proteic aggregate of ammonium and magnesium phospholinoleate-palmitoleate anhydride in the association or combination of drugs or treatments that characterizes the present invention can be understood as a type of adjuvant immunotherapy. The referred compound has a role similar to that of interferons and other exogenous cytokines, in the drug combinations or associations already known in the state of the art and mentioned in this report.

However, because of the evident benefits arising from the use of the biological response modifier (proteic aggregate of ammonium and magnesium phospholinoleate-palmitoleate anhydride) of being able to induce endogenous formation of interferon-gamma (IFN-gamma) and other key substances, such as cytokines (IL-2) that are essential to the proper functioning of the immune system in the face of disease, and as shall be seen in this report, the presence in the association or combination of this biological response modifier (proteic aggregate of ammonium and magnesium phospholinoleate-palmitoleate anhydride) also allows to add other remarkable and innovative therapeutic properties to the invention, with a much wider action than those reported in the state of the art, also for the biological response modifier (proteic aggregate of ammonium and magnesium phospholinoleate-palmitoleate anhydride) and for these other cytokines either isolated or in association, such as the ability to provide means of treatment for other clinical complications arising from the primary disease and, finally, the ability to solve or minimize adverse side effects of other drugs and treatments.

In view of these differentiating characteristics, the invention not only has wider action or therapeutic power than other associations or combinations of drugs and/or treatments in the state of the art that use the so-called adjuvant immunotherapy with the aforementioned cytokines, though from exogenous sources, because of its ability, conferred by the biological response modifier, of inducing or stimulating endogenous production of effector cytokines that trigger immune response, such as interferons (IFN-gamma) and interleukins (IL-2), and, if necessary and depending on the specific type of treatment for the patient, may allow the physician to consider minimizing the use of exogeneous cytokines, such as interferon, as well as other exogenous cytokines and/or reduce their doses when the regimens prescribed involve their association with other drugs, among other benefits.

This ability or property of the present invention, that is, physiological or endogenous induction of effector cytokines that trigger TH-1 type immune response, such as the IFN-gamma and IL-2, resulting from the use of the biological response modifier (proteic aggregate of ammonium and magnesium phospholinoleate-palmitoleate anhydride) in the invention also allows to obtain a significant economic advantage, besides the therapeutic benefits: Minimization or elimination of the occurrence of intolerance reactions or toxicity in patients, which are common side effects of the use of these cytokines that modulate immune response, such as interferons and interleukins obtained from exogenous sources, which often demand additional costs for their control.

For an expert with knowledge in the state of the art, the benefits of using substances of physiological or endogenous origin to replace or minimize the necessary amounts of the same substances, though obtained from exogenous sources, in the treatment of diseases, by minimizing the risk of adverse side effects such as allergic reactions are evident and need no further explanation.

The invention can be used in two ways:

1) Use of the biological response modifier (proteic aggregate of ammonium and magnesium phospholinoleate-palmitoleate anhydride) associated to regimens or protocols consisting in the combination of this specific immunomodulator with other drugs and/or non-drug treatments, the latter empirically chosen or selected by medical professionals at the beginning of therapy, among those available in the state of the art and that are deemed more appropriate to be used with the biological response modifier (proteic aggregate of ammonium and magnesium phospholinoleate-palmitoleate anhydride), depending on patient and disease state, as shall be detailed in the present report.

2) Use of the biological response modifier (proteic aggregate of ammonium and magnesium phospholinoleate-palmitoleate anhydride) as a component or part in the manufacture of new drugs, when combined or associated with other drugs of the most different types and categories, and also other non-drug treatments, as shall be detailed in this report.

An in order to ensure that the present invention is perfectly understood, some practical examples of its use in different tumors and pathologies of interest follow, as well as some comments and examples of use of other substances and associations that have not been described in the state of the art until now as therapies against these disorders.

These examples are also provided to help understanding the many possibilities and benefits provided by the invention for the treatment of chronic systemic diseases such as cancer, associated clinical problems and also for the correction of problems associated to other drugs and/or existing treatments in the state of the art.

It can be affirmed that any expert with knowledge in the state of the art based only on the information and practical examples to be provided in the present report should be able to fully understand and use the present invention to its full extent.

These practical examples are merely illustrative and do not intend to limit the scope of the present invention.

PRACTICAL EXAMPLE

Use of the Present Invention for the Treatment of Tumors in Experimental Animals—Use of Two Biological Response Modifiers Several experiments were conducted using the same experimental model of Lewis lung carcinoma (3 LL) in animals, where the therapeutic effect of the biological response modifier (proteic aggregate of ammonium and magnesium phospholinoleate-palmitoleate anhydride) used alone was assessed. Also, for comparative purposes, the present invention, that is, the biological response modifier (proteic aggregate of ammonium and magnesium phospholinoleate-palmitoleate anhydride) associated to another biological response modifier (Il-2) was assessed, as well as the biological response modifier (proteic aggregate of ammonium and magnesium phospholinoleate-palmitoleate anhydride) used in association with cytotoxic compounds (vindesine sulfate and cisplatin).

In the first experiment (Table A) the production of cytokines and survival provided by the biological response modifier (proteic aggregate of ammonium and magnesium phospholinoleate-palmitoleate anhydride) in the animals treated with the biological response modifier (proteic aggregate of ammonium and magnesium phospholinoleate-palmitoleate anhydride) used alone and in combination with another biological response modifier called Interleukin-2 (Il-2) was assessed for comparative purposes. The referred compound (Il-2) is widely use in the treatment of cancer in the state of the art. Data from this first experiment is shown in Table A.

In the second experiment (Table B) the use of the immunomodulator (proteic aggregate of ammonium and magnesium phospholinoleate-palmitoleate anhydride) used alone and in combination with two other cytotoxic compounds: vindesine sulfate and cisplatin, available in the state of the art and widely used in the treatment of cancer, were comparatively assessed in experimental animals. The data of this second experiment are contained in Table B and Table C.

Association or Combination of the Biological Response Modifier (Proteic Aggregate of Ammonium and Magnesium Phospholinoleate-Palmitoleate Anhydride) with Other Biological Response Modifiers and Chemotherapy Drugs General Experimental Drawing Animals: 3-week-old C57B1/6 female mice were used in all the experiments (Table A, Table B, Table C)

Tumor: Lewis lung carcinoma (3LL) was the tumor selected for all the in vivo assessments (Table A, Table B, Table C) in these experiments, with the cells maintained in culture medium and inoculated subcutaneously in the animals at the concentration of 6×105 cancer cells (3 LL) for each animal.

Biological Response Modifiers Used (Table A and Table B):
  a) Proteic aggregate of ammonium and magnesium phospholinoleate-palmitoleate anhydride
  b) Interleukin 2 (IL-2)
  Cytotoxic Chemotherapy Drugs Used (Table B and Table C)
  c) Vindesine sulfate
  d) Cisplatin Treatments: All treatments began 24 hours after the inoculation of cancer cells.

Observation period: The animals were evaluated during an observation period of 100 days in the survival experiment.

The animals used in the quantification of cytokines were observed until the 21st day.

Serum cytokine levels: In order to quantify the cytokine level in serum from mice, the blood samples were collected in the mice from retro-orbital puncture at the 21st day after the beginning of treatment and separate plasma pools were made from the blood samples.

The blood samples were maintained at 4° C. for 24 hours for clot retraction and were then centrifuged at 2700 rpm for 30 minutes. Quantitative analyses of IFN-gamma and IL-2 were made with the kit BD TM Cytometric Bead Array—Mouse Th1/Th2 Cytokine CBA (BD Biosciences, CA-EUA).

Experimental Protocol

1st Experiment—Practical effect of the invention—Animals treated with the biological response modifier (Proteic aggregate of ammonium and magnesium phospholinoleate-palmitoleate anhydride) associated to Interleukin 12 (IL-12). (Table A).

Animals: 3-week-old C57B1/6 female mice

Tumor model: Lewis lung carcinoma (3LL) in the 6×105 concentration of cancer cells (3 LL) for each animal.

Biological Response Modifiers Used: (Table A and Table B):
  a) Proteic aggregate of ammonium and magnesium phospholinoleate-palmitoleate anhydride
  b) Interleukin 2 (IL-2)

Two batches of 20 mice (C57BL/6) each one, inoculated with 3 LL cells (6×105 cells/animal) were treated only with daily intraperitoneal injections of the biological response modifier (proteic aggregate of ammonium and magnesium phospholinoleate-palmitoleate anhydride), as follows: 5.0 mg/kg/daily dose (Table A—Group 1—IM-1) and 0.5 mg/kg/daily dose (Table A—Group 2—IM 2), applied in three 3 weekly cycles. The animals were followed up for 100 days.

A third batch (Table A—NaCl—Group 3) with 20 animals was also inoculated with 3 LL cells (6×105 cells/animal), treated only with 0.2 ml of saline solution (NaCl 0.9%) and followed up for an equal period of time for control purposes.

A fourth batch of 20 animals (Group 4) inoculated with 3 LL cells (6×105 cells/animal), was treated with 0.5 mg/kg/day of the proteic aggregate of ammonium and magnesium phospholinoleate-palmitoleate anhydride (Table A—Group 4—IM-2) and Interleukin-12 (IL-12), 0.05 g/animal given jointly by intraperitoneal injections in 3 weekly cycles. The animals were followed up for 100 days.

A fifth batch of 20 animals (Table A—Group 5) inoculated with 3 LL cells (6×105 cells/animal) was treated with Interleukin-12 (IL-12), 0.1 µg/animal applied by intraperitoneal injection in 3 weekly cycles. The animals were followed up for 100 days, and the number of survivors was expressed in percentage.

The results are shown in Table A:

TABLE A

| groups, drugs and dosages | Days | % Survivors |
|---|---|---|
| Group 1 IM-1 (5 mg/kg) | 100 | 40 |
| Group 2 IM-2 (0.5 mg/kg) | 100 | 20 |
| Group 3 (Nacl 0.9%) | 100 | 3 |
| Group 4 IM-2 (0.5 mg/kg) + Il-2 (0.05 µg/animal) | 100 | 96 |
| Group 5 (IL-2-0.1 µg/animal) | 100 | 50 |

2° Experiment—Practical effect of the invention—Animals treated with the biological response modifier (Proteic aggregate of ammonium and magnesium phospholinoleate-palmitoleate anhydride) associated to vindesine sulfate and cisplatin (Table B and Table C).

Animals: 3-week-old C57B1/6 female mice

Tumor model: Lewis lung carcinoma (3LL) in the 6×105 of cancer cells (3 LL) for each animal.

Cytotoxic Chemotherapeutic Drugs Used (Table B and Table C)
  c) Vindesine sulfate
  d) Cisplatin Cytokine measurement (IFN-gamma and IL-2): kit BD TM Cytometric Bead Array—Mouse Th1/Th2 Cytokine CBA (BD Biosciences, CA-EUA)—(Table C).

Two batches of 20 mice (C57BL/6), with 10 males and 10 females each, transplanted with cells of Lewis lung carcinoma (3LL—6×105 cells/animal) were treated only with the proteic aggregate of ammonium and magnesium phospholinoleate-palmitoleate anhydride, intraperitoneally given at the 5.0 mg/kg/daily dose (Table B— group 1) and 0.5 mg/kg/daily dose (Table B— group 2), applied in 3 weekly cycles that started 24 hours after tumor inoculation. The animals were followed up for 100 days (Table B).

A third batch (Table B— group 3) with 20 animals was equally inoculated with 3 LL cells (6×105 cells/animal), treated only with 0.2 ml of saline solution (NaCl) at 0.9%, intraperitoneally given 3 times a week. The treatment began 24 hours after tumor inoculation and the animals were followed up for 100 days (Table B).

A fourth batch of 20 animals (Table B— group 4) inoculated with 3 LL cells (6×105 cells/animal), was treated with 0.5 mg/kg/day of proteic aggregate of ammonium and magnesium phospholinoleate-palmitoleate anhydride and vindesine sulfate (3 mg/kg) and cisplatin (1 mg/kg) jointly given by intraperitoneal injection 24 hours after tumor cell inoculation, in 3 weekly cycles. The animals were followed up for 100 days (group 4—Table B).

A fifth batch of 20 animals (Table B— group 5) inoculated with 3 LL cells (6×105 cells/animal) was treated only with vindesine sulfate (3 mg/kg) and cisplatin (1 mg/kg) administered together by intraperitoneal injection 24 hours after tumor cell inoculation, in 3 weekly cycles. The animals were followed up for 100 days (Table B).

A sixth batch of animals (Table C—Group 6) was treated only with saline solution (NacL 0.9%) intraperitoneally given 24 hours after tumor cell inoculation in 3 weekly cycles. The animals under this experiment were sacrificed on the 21th day after the beginning of the treatment for the measurement of the IL-2 and Interferon-gamma levels (Table C—Group 6).

A seventh batch of 20 animals (Table C—Group 7) inoculated with 3 LL cells (6×105 cells/animal) was treated with 0.5 mg/kg/day of proteic aggregate of ammonium and magnesium phospholinoleate-palmitoleate anhydride and vindesine sulfate (3 mg/kg) and cisplatin (1 mg/kg) administered together by intraperitoneal injection 24 hours after tumor cell inoculation, in 3 weekly cycles. These animals were also sacrificed on the 21° day after the application for the measurement of the IL-2 and Interferon-gamma levels (Table C—Group 7).

An eighth batch of 20 animals (Table C—Group 8) inoculated with 3 LL cells (6×105 cells/animal, was treated only with vindesine sulfate (3 mg/kg) and cisplatin (1 mg/kg) administered together by intraperitoneal injection 24 hours after tumor cell inoculation in 3 weekly cycles. These animals were sacrificed on the 21° day after the beginning of the treatment for the measurement of the IL-2 and Interferon-gamma levels (Table C—Group 8).

The cytokines (IFN-gamma and IL-2) were measured with the use of a BD TM Cytometric Bead Array—Mouse Th1/Th2 Cytokine CBA (BD Biosciences, CA-EUA) kit.

The results of these experiments are shown in Table B, for the percentage of survivors, and in Table C, for the cytokine levels (IFN-g and IL-2).

TABLE B

|  | Percentage of survivors | |
| --- | --- | --- |
|  | 21 Days (%) survivors | 100 Days (%) survivors |
| Group 1 | 100 | 41 |
| Group 2 | 100 | 19 |
| Group 3 | 100 | 18 |
| Group 4 | 100 | 90 |
| Group 5 | 100 | 60 |
| Group 6 | 0 | — |
| Group 7 | 0 | — |
| Group 8 | 0 | — |

TABLE C

| | Levels of IFN-g/IL-2 | | |
| --- | --- | --- | --- |
|  | Days after the beginning of treatment | Interferon-gamma (IFN-g) pg/ml | Interleukin-2 (IL-2) pg/ml |
| Group 6 (control) | 21 | 1256 ± 106 | 804 ± 75 |
| Group 7 | 21 | 1448 ± 80 | 890 ± 60 |
| Group 8 | 21 | 857 ± 38 | 730 ± 35 |

Discussion of the Results—Practical Use of the Invention—Association of the Biological Response Modifier (Proteic Aggregate of Ammonium and Magnesium Phospholinoleate-Palmitoleate Anhydride,) and Interleukin-12

The use of the present invention, that is, the association or combination of the biological response modifier (proteic aggregate of ammonium and magnesium phospholinoleate-palmitoleate anhydride) in the practical experiment contained in Table A has clearly demonstrated the use of the invention, consisting, in this case, in an association of the biological response modifier (proteic aggregate of ammonium and magnesium phospholinoleate-palmitoleate anhydride) with another biological response modifier, in this case, Interleukin-12 (IL-12) has a much more efficient therapeutic action regarding the survival of test animals assessed 100 days after the beginning of the experiment.

A it can be seen in Table A, the mice group given only the biological response modifier (proteic aggregate of ammonium and magnesium phospholinoleate-palmitoleate anhydride) alone had a 20% survival percentage (table A—Group-2—IM-2—0.5 mg/kg) and 40% (Table A—Group 1—IM-1—5.0 mg/kg), respectively, 100 days after tumor cell inoculation, and the group of animals treated only with IL-12 (group 5-IL-12-0.1 g/animal) had a survival rate of 50%.

Although the survival rate of animals treated with the biological response modifier (proteic aggregate of ammonium and magnesium phospholinoleate-palmitoleate anhydride) alone at its highest dosage (group Table A—1—IM-1—5 mg/kg), that is, 40% of the survivors is very similar to the survival rate of the group treated only with 11-12 (Table A—Group 5—IL-2—0.1 ug/animal) with a survival rate of 50%, the experiment reveals the remarkable effectiveness of the use of the present invention the use of the invention regarding the percentage of surviving animals.

It can be clearly seen that the therapeutic effectiveness of the invention, that is, of the combination of the biological response modifier (proteic aggregate of ammonium and magnesium phospholinoleate-palmitoleate anhydride) and Interleukin-12 (IL-12) is clearly greater than the effect obtained with the use of any of the other two compounds when used alone, regarding the percentage of surviving animals at the end of the experiment, which is a 96% percentage of survivors (Table A—Group 4).

Interestingly, the doses of the biological response modifier (proteic aggregate of ammonium and magnesium phospholinoleate-palmitoleate anhydride) and Interleukin 12 (IL-12) needed or used, when administered in the combination form made available for usage by the present invention, and with the purpose of obtaining a much greater therapeutic effect (Table A—Group 4) are much lower than those previously used, when administered alone, since the dose used in the association or combination for IL-12 to obtain a 96% survival rate (Table A—Group 4) is half the dose previously used, that is, 0.05 ug/animal (table A—Group 4) and the dose of the biological response modifier (proteic aggregate of ammonium and magnesium phospholinoleate-palmitoleate anhydride) is 0.5 mg/kg (Table A—Group 4).

It can be clearly seen that the use of the invention in this practical example, that is, the combination of the biological response modifier (proteic aggregate of ammonium and magnesium phospholinoleate-palmitoleate anhydride) with an exogenous cytokine, that is, the Interleukin-12 (IL-12) has a therapeutic effectiveness, in what concerns the number of surviving animals (96%—Table A—Group 4), much higher than the best results obtained for any of the other two compounds when used alone, that is, 40% of survivors (group 1—Table A) for the biological response modifier (proteic aggregate of ammonium and magnesium phospholinoleate-palmitoleate anhydride) and 50% for interleukin-12 (group 5—table A).

Therefore, a higher therapeutic effectiveness was obtained with the use of the present invention (Table A—Group 4), which is attested by the rate of surviving animals, with the administration of lower doses of both compounds, biological response modifiers, compared to the findings obtained for any of the other two aforementioned compounds, when used alone in this experiment.

Practical Use of the Invention—Association of the Biological Response Modifier (Proteic Aggregate of Ammonium and Magnesium Phospholinoleate-Palmitoleate Anhydride,) and Cytotoxic Drugs (Vindesine Sulfate and Cisplatin)—(Table B and Table C).

When the invention is used in another experiment reproducing a common situation in the state of the art, that is, a protocol of cytotoxic chemotherapy drugs in association (vindesine sulfate and cisplatin) with the necessary use, associated or combined, of the biological response modifier (proteic aggregate of ammonium and magnesium phospholinoleate-palmitoleate anhydride) the results obtained are similar (Table B).

Analysis of data in Table B, that is, the results obtained for vindesine sulfate and cisplatin (Table B) shows that the biological response modifier (proteic aggregate of ammonium and magnesium phospholinoleate-palmitoleate anhydride) used alone resulted in a survival rate of 41% of the experimental animals, when administered at a dose of 5 mg/kg (Group 1—Table B) and a survival rate of 19% for the same compound when used alone at a dose of 0.5 mg/kg (Group 2—Table B), which is almost the same effect obtained in the control group that received only 0.9% of NaCl (control group—group 3—Table B) and that had 18% of surviving animals after 100 days (Group 3—Table B).

The group that was given the combination of drugs/therapies that constitute the present invention, that is, the biological response modifier (proteic aggregate of ammonium and magnesium phospholinoleate-palmitoleate anhydride) at a dose of 0.5 mg/kg, associated to vindesine sulfate at a dose of 3 mg/kg and cisplatin (1 mg/kg) in 3 weekly cycles resulted in a survival rate of 90% in 100 days (Group 4—Table B), which is much higher than the survival rate of 60% (Group 5—Table B) obtained for the same dose of vindesine sulfate (3 mg/kg) and cisplatin (1 mg/kg) in 3 weekly cycles, however without the presence of the specific biological response modifier.

As it can be seen in the data from Table B, the use of the invention, that is, the biological response modifier (proteic aggregate of ammonium and magnesium phospholinoleate-palmitoleate anhydride) used in the lowest dose, that is, at the dose of 0.5 mg/kg, though associated to vindesine sulfate and cisplatin (Group 4—Table B), have made it possible to obtain a survival rate of 90% (Group 4—Table B), compared to the mere 19% when the biological response modifier was administered alone at the same dose of 0.5 mg/kg, (Group 2—Table B).

However, this 90% survival rate (Group 4—Table B) obtained with the use of the invention is also much higher than the result obtained with the combination of the cytotoxic agents only (chemotherapy protocol) used without the biological response modifier (proteic aggregate of ammonium and magnesium phospholinoleate-palmitoleate anhydride), which was only a 60% survival rate (Group 5—Table B).

Regarding the production of cytokines with effector mechanisms of immune response, it can be seen in Table C (cytokine quantification) a significant rise in the IFN-g and IL-2 levels for the group that used the combination of drugs/therapies that constitute the present invention (Group 7—Table C) compared to the levels found for the group that was given only the two cytotoxic compounds associated (Group 8—Table C).

Although the levels of effector cytokines and/or cytokines associated to a TH-1 type immune response) in the group that used the combination of drugs/therapies that constitute the present invention (Group 7—Table C) are similar to the levels found in the control group (Group 6—Table C), a significant rise was observed compared to the group that was given only the association of cytotoxic compounds (Group 8—Table C), which is very relevant, given the neoplastic process and the use of immunosuppressive compounds (cisplatin).

Presumably, the higher survival rates obtained for the group treated with the combination of drugs/therapies that constitute the present invention (Group 4—Table B) can be associated to the stimulation of the production of effector cytokines of the immune response (IFN-g and IL-2) caused by the presence of the biological response modifier (proteic aggregate of ammonium and magnesium phospholinoleate-palmitoleate anhydride) in combination or association with cytotoxic compounds (Group 7—Table C), a hypothesis that is corroborated by the levels of these cytokines compared to the levels in the control group (Group 6—Table C) and particularly the levels of effector cytokines compared to the levels obtained with the use of the association of cytotoxic compounds only (Table C—Group 8).

Obviously, the practical effect of the invention does not depend on the knowledge or elucidation of possible mechanisms of action of any components, including the increase in cytokine levels caused by the presence of the biological response modifier (proteic aggregate of ammonium and magnesium phospholinoleate-palmitoleate anhydride).

However, the practical result of the experiments shown in Table C is important because it reveals that the use of the invention, that is, the biological response modifier (proteic aggregate of ammonium and magnesium phospholinoleate-palmitoleate anhydride) leads to increased endogenous production of the levels of cytokines with effector mechanisms of immune response (IFN-g and IL-2), and more importantly, that this effect is maintained in the presence or with the use of cytotoxic and immunosuppressive drugs.

The ability of the present invention (Table C), or else, the endogenous induction of cytokines with effector mechanisms of immune response, even in the presence of a chronic systemic disease (cancer) and of immunosuppressive drugs, reveals that besides triggering a immune system response (TH-1 response) associated to the state of the art as necessary to assist the response or reaction of the host body to neoplasias, it shows the full effectiveness of this invention, that is, of the biological response modifier (proteic aggregate of ammonium and magnesium phospholinoleate-palmitoleate anhydride) of causing an (endogenous) increase in the number of cytokines with effector mechanisms of immune response (IFN-g and IL-2), or else, in clinical practice, its use in the invention shall also counterbalance the immunosuppressive effect of other drugs that might be used in association or combination.

The remarkable property of the invention, that is, the endogenous production of effector cytokines (IFN-gamma and IL-2), confirms the effectiveness of the invention in practical situations where experts with knowledge of the state of the art who would no longer need to use exogenous cytokines, or in the reduction of cytokine doses in chemotherapy protocols where such use is associated to other drugs or non-drug treatments.

Finally, it can be easily seen in data from Table B that the present invention, that is, the association or combination of the biological response modifier (proteic aggregate of ammonium and magnesium phospholinoleate-palmitoleate anhydride) is also fully effective for use in treatment regimens that include more than one chemotherapy drug (chemotherapy protocols) with therapeutic gains for the combination or association, or else, generating medical benefits greater than those obtained with the use of any of the isolated compounds (Group 4—Table B).

For the purposes of the present invention, that is, for the preventive, curative or palliative treatment of chronic systemic diseases such as cancer, the use of the biological response modifier must or shall be associated to at least one compound, drug or other non-drug treatment. More than one compound, drug or non-drug treatment can be used, including in the form of combination or association between these other elements.

These data of the practical example (Table B and Table C) also reveal one of the useful aspects of this invention, because it not only proves that the invention has wider therapeutic action than the therapeutic action of the isolated components of the association or combination. Also, it can be affirmed that the present invention will make it possible to use lower doses of the agents or compounds to obtain a greater effect than that obtained with higher doses of the isolated compounds. This will create significant therapeutic, economic and quality-of-life benefits that can be clearly understood by any expert with knowledge of the state of the art without the need for further explanations.

Extrapolation from Experimental Results

In view of the practical examples given, and for the purposes of the present invention, any expert with knowledge of the state of the art can understand that the practical use of the invention, that is, the effect of the biological response modifier (proteic aggregate of ammonium and magnesium phospholinoleate-palmitoleate anhydride) in association or combination with other compounds, either cytotoxic or other anti-cancer drugs, such as biological response modifiers or immunotherapy drugs, could be maximized, that is, the use of the association or combination is more powerful or therapeutically effective than the use of the isolated compounds, so that depending on the case in question and on the patient status, lower or higher doses of the compounds could be used and finally more than one drug or compound could be associated to the biological response modifier (proteic aggregate of ammonium and magnesium phospholinoleate-palmitoleate anhydride).

An in order to ensure that the present invention is perfectly understood, some practical examples of its use in different tumors and pathologies of interest follow, as well as some comments and examples of use of other substances and associations that have not been described in the state of the art until now as therapies against these disorders.

Furthermore, new and remarkable data not known in the state of art until now, concerning to one of the components of the invention, that is, the biological response modifier (proteic aggregate of ammonium and magnesium phospholinoleate-palmitoleate anhydride), related with the invention, are provided.

Toll-Like Type Cell Receptors (Toll-Like Receptors) and Immune Response—State of the Art The so-called toll like receptors or TLRs are cell transmembrane proteins that form a family of cell receptors located in the surface of macrophages and other specialized cells of the immune system such as the dendritic cells, and are considered in the state of the art essential components of the innate immune system.

They are involved in molecular recognition of components of bacterial and viral components, essential for the activation of the immune response, or else, its function consists in the recognition of molecular components of invading microorganisms that are practically invariable, and based on such recognition, it triggers an immune response to eliminate these foreign invaders.

These molecular components of invading microorganisms are also called ligands. The ligands, recognized by toll-like receptors, are practically invariable in most microorganisms and may consist of lipopolysaccharides (LPS), endotoxins, lipoproteins, viral nucleic acids and other substances.

After the stimulation of TLRs by these ligands, several signaling proteins are activated, which, in turn, cause transcription factors such as AP-1, NF-κB and IRFs to be activated, and the latter induce the secretion of pro-inflammatory and effector cytokines that will initiate immune response.

Toll-Like Receptors and Carcinogenesis

With the new advancements in science, toll-like receptors are no longer considered mere participants in the innate immune response to foreign pathogens. They also trigger other immune responses and orchestrate other cellular and physiological processes, including and of particular interest with respect to the present report, processes involved in carcinogenesis. For a brief introduction to the current state of the art, please see: Seth Rakoff—Nahoum and Ruslan Medzhitov—Toll-like receptors and cancer—Cancer Nature Reviews—Vol. 9—January—2009.

Assessment of the Receptor Ligand Binding Ability and of the Activation of Toll-Like Receptors by the Biological Response Modifier Assessment of the ability of biological response modifiers of activating toll-like receptors is of utmost importance in the state of the art, not only to elucidate the possible mechanisms of action of these compounds, but also for guiding the construction of new practical applications.

Previous state of the art information is available (PI—0305373-3, PI 0801803-0, U.S. Ser. No. 10/978,683, EPA 0426250.3.2405, WO/2009/097670) on the ability of the biological response modifier (proteic aggregate of ammonium and magnesium phospholinoleate-palmitoleate anhydride) of inducing or stimulating the endogenous production of cytokines with effector mechanisms of TH-1 type immune response, especially the Interleukin-2 (IL-2) and the Interferon-gamma (IFN-g), which is confirmed by experiments in animal models included in the present report (Table C). In view of this, the product was used in an in vitro experiment to explore and quantify the possible ability of this specific compound to act also as a ligand or agonist for toll-like cellular receptors.

This connection between the presence or stimulus to the production of cytokines with effector mechanisms of TH-1 type immune response, known to be stimulated in animal models, that is, endogenously by the biological response modifier (proteic aggregate of ammonium and magnesium phospholinoleate-palmitoleate anhydride) and a possible initial activation by these compounds of toll-like receptors expressed by immune system cells was a hypothetical possibility, because this type of immune response (TH-1-type response) may be sometimes associated to immune responses triggered, after activation of toll-like receptors, by compounds whose molecular formula contain e.g. of elements or components such as lipopolysaccharides, lipids or nucleic acids, which are able to work as toll-like receptor agonists or ligands. For illustrative purposes, we cite: Fearon et al. Science 1996; 272:50-53 and Medzhitov et al. Cell 1997; 91:295-298.

The experimental proof of the surprisingly and remarkable ability of the biological response modifier (proteic aggregate of ammonium and magnesium phospholinoleate-palmitoleate anhydride) of binding to toll-like receptors in cells, which had occurred in the way is shown below, has provided important additional informations, not contained in the state of art, to guide the choice or deliberate selection of the referred compound as a especially useful component in innovative and absolutely unprecedented practical uses, as will be fully describe in the present report.

A standard experiment in the state of the art performed to demonstrate and quantify the ability of the biological response modifier (proteic aggregate of ammonium and magnesium phospholinoleate-palmitoleate anhydride) to act as a ligand (agonist) or stimulator of toll-like cell receptors is provided below for illustrative purposes and does not intend to limit the scope of the present invention.

Binding Ability of the Biological Response Modifier (Proteic Aggregate of Ammonium and Magnesium Phospholinoleate-Palmitoleate Anhydride) for Toll-Like Cell Receptors—Practical Experiment Material and Methods:

Samples in three concentrations (0.5 µg/mL, 5 µg/mL, and 50 µg/mL) of the biological response modifier (proteic aggregate of ammonium and magnesium phospholinoleate-palmitoleate anhydride) were dissolved in dimethylsulfoxide (DMSO at 1%) at the concentration of 1% and incubated with 293 TLR cells (HEK293 cells) in microplates, in duplicate, for 20 hours.

Standard compounds, that is, ligands known for TLR 3 to TLR9 in predetermined concentrations were also incubated in microplates with 293 TLR cells (HEK293 cells) for 20 hours.

Subsequently, absorbance readings were taken of the microplates by fluorescence at 650 nm using a Beckman Coulter AD 340C Absorbance Detector device with three concentrations of the biological response modifier (proteic aggregate of ammonium and magnesium phospholinoleate-palmitoleate anhydride) incubated with the HEK293 cells and readings were also taken of the microplates incubated with the same cells and the control substances, for comparative assessment of the percentage of binding of the aforementioned compounds to toll-like receptors expressed in HEK293 cells.

Samples proteic aggregate of ammonium and magnesium phospholinoleate-palmitoleate anhydride: 0.5 µg/ml, 5 µg/ml, and 50 µg/ml in DMSO at 1%

Cells: HEK293 cells expressing human TLRs (TLR 2 to TRL 9)

Controls (ligands)
   TLR2: HKLM (heat-killed *Listeria monocytogenes*)—108 cells/ml
   TLR3: Poly (I: C)—1 µg/mL
   TLR4: *E. coli* K12 LPS 100 ng/ml
   TLR5: *S. typhimurium* flagellin—100 ng/ml
   TLR7: CL097—1 µg/mL
   TLR8: CL075—1 µg/mL
   TLR9: CpG ODN 2006—1 µg/mL
   NF-κB Control cells: TNFα—100 ng/ml
Results (Tables T-1 and Table T-2)

TABLE T-1

| | | Screening 1 | | | |
|---|---|---|---|---|---|
| Cells 293/ | Number of Ligand | MRB 50 µg/mL | MRB 5 µg/mL | MRB 0.5 µg/mL | Controls+ |
| hTLR20. | 0.139 | 2.289 | 0.904 | 0.204 | 2.434 |
| hTLR3 | 0.127 | 0.082 | 0.088 | 0.086 | 3.440 |
| hTLR4 (MD2-CD14) | 0.127 | 0.994 | 0.083 | 0.071 | 2.573 |
| hTLR5 | 0.151 | 0.244 | 0.194 | 0.152 | 3.662 |
| hTLR7 | 0.132 | 0.054 | 0.076 | 0.073 | 3.222 |
| hTLR8 | 0.122 | 0.072 | 0.085 | 0.085 | 3.313 |
| hTLR9 | 0.131 | 0.063 | 0.098 | 0.111 | 2.582 |
| Cells NF-κB Controls | 0.073 | 0.065 | 0.070 | 0.067 | 2.221 |

| | Screening 2 | | | |
|---|---|---|---|---|
| Cells 293/TLR | MRB 50 µg/mL | MRB 5 µg/mL | MRB 0.5 µg/mL | Controls+ |
| hTLR2 | 0.139 | 2.133 | 0.630 | 0.251 | 2.595 |
| hTLR3 | 0.120 | 0.078 | 0.094 | 0.085 | 3.287 |
| hTLR4 (MD2-CD14) | 0.131 | 0.938 | 0.079 | 0.075 | 3.468 |
| hTLR5 | 0.131 | 0.190 | 0.155 | 0.157 | 3.798 |
| hTLR7 | 0.125 | 0.046 | 0.055 | 0.072 | 3.359 |
| hTLR8 | 0.114 | 0.070 | 0.115 | 0.100 | 3.338 |
| hTLR9 | 0.115 | 0.074 | 0.105 | 0.113 | 2.519 |
| Cells NF-κB Controls | 0.065 | 0.054 | 0.060 | 0.073 | 2.042 |

Units = OD (650 nm)

TABLE T-2

| Cells 293/TLR (% ligands) | MRB 50 µg/mL | MRB 5 µg/mL | MRB 0.5 µg/mL | Controls |
|---|---|---|---|---|
| hTLR2 | 88%* | 31%(***) | 9% | 100% |
| hTLR3 | 2% | 3% | 3% | 100% |
| hTLR4 (MD2-CD14) | 32% | 3% | 2% | 100% |
| hTLR5 | 6% | 5% | 4% | 100% |
| hTLR7 | 2% | 2% | 2% | 100% |
| hTLR8 | 2% | 3% | 3% | 100% |

TABLE T-2-continued

| Cells 293/TLR (% ligands) | MRB 50 µg/mL | MRB 5 µg/mL | MRB 0.5 µg/mL | Controls |
|---|---|---|---|---|
| hTLR9 | 3% | 4% | 4% | 100% |
| Cell NF-κB Controls | 3% | 3% | 3% | 100% |

Observations: Table T1 (numerical values for OD=650 nm). Table T2 (% bindings)=Average of screening 1 and screening 2 values (table T-1)

Legend: MRB=Proteic aggregate of ammonium and magnesium phospholinoleate-palmitoleate anhydride Results: A concentration of 5 ug/ml of the compound (proteic aggregate of ammonium and magnesium phospholinoleate-palmitoleate anhydride) was found to be able to bind to 31% of HEK293 cells that express TLR2, and the same compound at a concentration of 50 ug/ml can bind to 88% of HEK293 cells that express TLR-2.

A concentration of 50 ug/ml of the compound (proteic aggregate of ammonium and magnesium phospholinoleate-palmitoleate anhydride) was found to be able to bind to 32% of HEK293 cells that express the TLR-4 receptor.

None of the concentrations use for the biological response modifier has proven to be able to bind to HEK293 cells that express TLR-3, TLR-5, TLR-7, TLR-8 and TLR-9.

Conclusions: The biological response modifier (proteic aggregate of ammonium and magnesium phospholinoleate-palmitoleate anhydride) has a significant binding/stimulatory ability for TLR-2 at the concentration of 5 ug/ml that corresponds to 31% (Table T-2) of the stimulus of the standard ligand for this receptor, used as control.

The biological response modifier (proteic aggregate of ammonium and magnesium phospholinoleate-palmitoleate anhydride) has a significant binding/stimulatory ability (agonist) both for TLR-2 and TRL-4 at a concentration of 50 ug/ml corresponding to 88% (Table T-2) and 32% (Table T-2) respectively, of the stimulus of the standard ligands for these receptors (controls).

Extrapolation of Results—State of the Art for the Practical Use of Ligand Compounds for Toll-Like Receptors The proof of the remarkable ability of the biological response modifier (proteic aggregate of ammonium and magnesium phospholinoleate-palmitoleate anhydride) to bind to TLR-2 and TLR-4 receptors, as shown in Table T-1 and Table T-2, that is, to act as an agonist and/or stimulator of these important elements that initiate and/or trigger immune response, including the innate immune response and the so-called adaptive immune response, added to other new information contained in the present report, allows the elaboration of new and entirely unprecedented practical applications and never before reported in the state of the art for the compound mentioned, that is, its deliberate use in the present invention as a therapeutic adjuvant and/or as a component in associations of drugs and treatments for the following situations of great interest to medicine, that will be cited in this report for illustrative purposes only, and in any way will be limited to or restricted by these examples:

a) As therapeutic adjuvant for the treatment of precancerous and cancerous lesions, associated to several inducing and/or carcinogenic agents such as chemical compounds. For illustrative purposes, please see: Gregory M Barton et al., Toll-like receptor 2 on inflammatory monocytes induces type I interferon in response to viral but not bacterial ligands. Nature Immunology, published online 4 Oct. 2009; doi: 10.1038/ni.1792.

In the particular case of precancerous lesions, e.g. associated to tissue changes caused by the action of viruses, agonist compounds (ligands) or stimulators of toll-like receptors can act additionally in the case of precancerous lesions such as pathological modifications of the cervical epithelium called cervical dysplasia caused by many types of human papilloma virus (HPV) inducing or stimulating the increase in the production of cytokines related to immune response of the TH-1 type, such as the tumor necrosis factor (TNF), interferon-gamma and interleukin-2 (IL-2), which may help inhibit the synthesis of viral proteins, and, thus, help prevent the further recognition and destruction of these cells infected by the immune system, minimizing the chances of occurrence of cell damage, chronic inflammation and consequently the carcinogenic processes associated to such events. For examples of the state of the art, please see: Guidotti L G, Chisari F V: Cytokine-mediated control of viral infections. Virology 2000; 273: 221-22 and Seth Rakoff-Nahoum and Ruslan Medzhitov—Toll-like receptors and cancer-Cancer Nature Reviews—Vol. 9—January—2009.

b) As therapeutic adjuvant for the treatment of precancerous and cancerous lesions, also associated to other nonviral carcinogenic agents such as chemical compounds, solar radiation and others, through the control of the mechanisms of cell repair and regeneration, modulation of inflammatory processes and, improving the healing process. For examples of the state of the art, please see: Larsen, P. H., Holm, T. H. & Owens, T. Toll-like receptors in brain development and homeostasis. Sci. STKE 2007, pe 47 (2007) and Michelsen, K. S. & Arditi, M. Toll-like receptors and innate immunity in gut homeostasis and pathology. Curr. Opin. Hematol. 14, 48-54 (2007) and also, Dvorak, H. F. Tumors: wounds that do not heal. Similarities between tumor stroma generation and wound healing. N. Engl. J. Med. 315, 1650-1659 (1986) and finally, Seth Rakoff—Nahoum and Ruslan Medzhitov—Toll-like receptors and cancer—Cancer Nature Reviews—Vol. 9—January—2009.

In view of the above, according to the prevalent understanding in the current state of the art in medicine, biological response modifiers also able to act by means of activation of toll-like receptors, such as the compound named imiquimod, are increasingly used to treat precancerous lesions caused by inducing or carcinogenic agents of various types, including viruses, chemical compounds and radiations that are usually preceded or accompanied by reactive and chronic inflammation, since the role of chronic inflammatory processes as a relevant carcinogenic factor is increasingly recognized in the state of the art.

In the state of the art, according to important authors, the compound called imiquimod, which is a biological response modifier, is reported in the state of the art medical literature as able to induce powerful immunomodulatory responses, via signaling in the immune system activated or mediated by toll-like receptors expressed by dendritic cells; more precisely TL-7 and TLR-8 type receptors shows antitumor activity that does not damage normal cells. For an example of the state of the art, we cite: Panelli M. et al.—Sequential gene profiling of basal cell carcinomas treated with imiquimod in a placebo-controlled study defines the requirements for tissue rejection—Genome Biol. 2007; 8(1): R8. Published online 2007 Jan. 15. Doi: 10.1186/gb-2007-8-1-r8.

Imiquimod is also reported in a clinical study with 169 patients as an effective preventive treatment for skin carcinoma, one of the most common types of tumor triggered by precancerous skin lesions, with a significant degree of protection against tumor recurrence in the 2 (two) years after therapy. For the state of the art, we cite: Quirk C, Gebauer K, Owens M, Stampone P., Two-year interim results from a 5-year study evaluating clinical recurrence of superficial basal cell carcinoma after treatment with imiquimod 5% cream daily for 6 weeks. Australas J Dermatol. 2006 November; 47(4): 258-65.

Although brief, the indications and references are representative of the most recent state of the art of toll-like cell receptors and provide indication of their importance to the invention.

The remarkable ability of the biological response modifier (proteic aggregate of ammonium and magnesium phospholinoleate-palmitoleate anhydride) of being able to bind to toll-like receptors (TLRs) can be more appreciated in the context of the present report, with several relevant quotes, that indicating that because of its ability to act as an agonist, the referred compound can have new and remarkable practical uses.

A description of the state of the art regarding the problems and obstacles in the state of the art involving the treatment of chronic diseases such as cancer, related to the use of the present invention to provide assistance in overcoming or minimizing such problems and obstacles.

Effect of the Biological Response Modifier in Precursor Cells in the Bone Marrow and in Peripheral Blood—Practical Experiments with Monkeys and Rodents—Extrapolation of Results As already explained in this report, it is widely accepted in the state of the art that the use of cytotoxic chemotherapy agents and other treatments have great practical limitations caused by myelosuppression and its clinical consequences, anemia and neutropenia, only the latter being of particular interest for the purposes of the present invention.

This is due to the fact that most drugs used for the treatment of chronic systemic diseases such as cancer, particularly cytotoxic compounds or treatments, may inhibit the growth and differentiation of several types of precursor cells located in the bone marrow, including precursor cells of the leukocyte series that are responsible for the production of specific types of peripheral blood cell populations that fight infections, especially those called neutrophils.

As a result of suppression in precursor cells of the leukocyte series located in the bone marrow patients treated with chemotherapy drugs often experience sharp falls of these cell populations (neutrophils) in the peripheral blood.

This condition called neutropenia may cause clinical or subclinical infections due to the reduction in the number of these defense cells, which may lead to the hospitalization of patients, with establishment of antibiotic treatments and/or reduction in the doses of cytotoxic drugs or finally causing the interruption of the treatment of the primary disease. For an example, we can cite: Fisher, D. C. and Peters, W. P.—Advances in the clinical use of granulocyte colony-stimulating factor and granulocyte-macrophage colony-stimulating factor to intensify cancer chemoterapy. Curr. Op. Hematol; 1, 221 (1994).

In view of this situation, compounds with the specific ability of stimulating the development of precursor cells in the bone marrow have been used as adjuvant therapies in combination with chemotherapy, aimed to correct or minimize the adverse effect of therapies and treatments against cancer, particularly neutropenia, acting in the precursor cells located in the bone marrow.

This indicates that because of this undesirable condition or side effect associated to the use of several types of drugs or treatments, other associated drugs should be used to attempt to correct side effects associated or caused by these therapies, added to the chemotherapy used for the treatment of the primary disease.

Among the compounds used for this purpose in the state of the art, it is worth mentioning the myeloid growth factors or else growth factors for granulocytes and macrophages.

The practical use of these substances, however, faces many limitations, such as the occurrence of side effects and the high treatment cost. There are also some adverse side effects of intensity ranging from moderate to severe, including bone pain, and, less frequently; the referred compounds may cause excessive cellular proliferation, leading to treatment discontinuation.

Therefore, it is undeniable that if it were possible to eliminate or at least minimize in chemotherapy or treatment protocols the use of any additional drugs merely aimed to counterbalance and/or correct adverse side effects of other treatments, that is immunosuppression, this would be undoubtedly a significant improvement in the state of the art in the treatment of chronic systemic diseases such as cancer, leading to significant therapeutic, economic and quality of life benefits.

The use of the present invention, that is, the association or combination of a specially selected biological response modifier (proteic aggregate of ammonium and magnesium phospholinoleate-palmitoleate anhydride) in combination with other cytotoxic compounds, or other compounds, has been proven in clinical practice to be able to increase therapeutic effectiveness compared to the isolated use of the components of the association or combination (Table A and Table B), and has also been found to be able to increase the production of cytokines with effector mechanisms of TH-1 type immune response, considered in the state of the art as essential to fight and control infections and cancer (Table C).

As shown below, through practical examples, the use of the present invention, that is, the association or combination of a specially selected biological response modifier (proteic aggregate of ammonium and magnesium phospholinoleate-palmitoleate anhydride) combined or associated to chemotherapy drugs or other drugs is not only able to improve anti-cancer therapeutic effectiveness of all the components of the association or combination, as it has been shown in the present report (Table A, Table B), but also increasing the production of effector cytokines related to the immune response, which has also been demonstrated in this report (Table C).

Interestingly and surprisingly, though, the use of the present invention, that is, the association or combination of the biological response modifier (proteic aggregate of ammonium and magnesium phospholinoleate-palmitoleate anhydride) with other drugs and treatments not only improves its effectiveness, as it has already been mentioned, but, also, in a remarkable way, makes it possible to prevent, correct or minimize undesirable effects of the use of myelosuppressive drugs on the progenitor cells of the bone marrow, that is, the use of the present invention makes it possible to correct, prevent or minimize suppression of bone marrow progenitor cells and its consequences, including neutropenia.

Therefore, the use of the present invention will make it possible in practice to associate a stronger therapeutic effect against the primary disease. Also surprisingly, it will be able to prevent, revert or minimize the possible immunosuppressant effect caused by drugs and/or treatments used in combination or association, particularly in the case of cytotoxic and/or myelotoxic compounds or treatments.

And in order to demonstrate, in clinical practice, the remarkable effect of this invention, some examples of its practical use in experiments and clinical assays follow.

These examples are given for explanatory purposes only, and by no means intend to limit the scope of the present invention.

Experiments and Previous Knowledge

In additional experiments carried out to evaluate its toxicity according to safety standards of new medicines, the biological response modifier (proteic aggregate of ammonium and magnesium phospholinoleate-palmitoleate anhydride) was used alone in Capuchin monkeys (*Cebus apella*) in three doses.

These animals were not suffering from any illness and were not given any additional drug or compound except the biological response modifier (proteic aggregate of ammonium and magnesium phospholinoleate-palmitoleate anhydride) and saline solution (NaCl 0.9%), the latter for control purposes.

Experimental:

Animals and Doses Used

Male Capuchin monkeys (*Cebus apella*) were used, 16 animals in total divided into four groups:

Control Group (four animals): Was given saline solution (NaCl 0.9%) at the same concentration as the experimental substance Low Dose Group—LD—(four animals): Was given intramuscularly 5 mg/kg/day of the proteic aggregate of ammonium and magnesium phospholinoleate-palmitoleate anhydride for 30 days.

Medium Dose Group—MD—(four animals):—Was given intramuscularly 10 mg/day of the proteic aggregate of ammonium and magnesium phospholinoleate-palmitoleate anhydride for 30 days.

High Dose Group—HD—(four animals): Was given intramuscularly 30 mg/day of the proteic aggregate of ammonium and magnesium phospholinoleate-palmitoleate anhydride for 30 days.

The animals were observed daily for 30 days, weighed daily and sacrificed at 30 days of the experiment, with blood samples taken for blood tests at the beginning and end of the experiment. The results are shown in Table D.

The main organs of the animals were extracted, preserved in formalin at 10%, and processed through the usual techniques for preparation of histological tests and the slides containing samples of micrometric thickness of the relevant tissues were stained with hematoxilin-eosin (HE) and analyzed for tissue and structural cell changes in light microscope, with the bone marrow tissues of the animals and the following changes observed in precursor cells for the leukocyte series being of particular interest for the purposes of the present report:

Histopathological findings—Bone marrow tissues: Regarding the animals (*Cebus apella*) that were given the biological response modifier (proteic aggregate of ammonium and magnesium phospholinoleate-palmitoleate anhydride) for four weeks (30 days, the histological findings in the bone marrow tissues have shown that the progenitor cells of the granulocytic series (leukocyte) were very activated, that is, in a proliferation and differentiation process, whereas the control animals did not show any relevant sign of activation for these specific cellular populations, for comparison purposes.

No changes were detected in the progenitor cells of the bone marrow for the erythrocyte series in the animals treated with the biological response modifier and in the control animals.

Blood tests: Results and discussion Consequently, due to the activation of the precursor cells in the bone marrow, the blood tests of animals treated with the compound showed dose-dependent changes in the elements of the leukocyte series measured in the peripheral blood, with a greater number of lymphocytes (**) (Table D) and granulocytes, compared to the control animals, and with the variation in the population of neutrophils (*) (Table D) at the end of the experiment (30 days) being of particular interest.

TABLE D

Monkeys Hematol. parameters

| Blood tests | Controls NaCl (0.9%) | LD Group 5 mg/kg/day | MD Group 10 mg/kg/day | HD Group 30 mg/kg/day |
|---|---|---|---|---|
| Erythrocytes ($10^6$/mm$^3$) | 6.7 ± 2 | 6.1 ± 0.1 | 5.1 ± 0.02 | 4.7 ± 0.1 |
| Hematocrit | 48.7 ± 0.7 | 45.0 ± 1.1 | 39.3 ± 0.7 | 36.8 ± 1.2 |
| Hemoglobin (g/dl) | 16.0 ± 0.6 | 14.7 ± 0.3 | 13.0 ± 0.0 | 11.5 ± 0.3 |
| Leukocytes | 11.8 ± 2.5 | 16.6 ± 4.1 | 18.9 ± 4.8 | 25.4 ± 2.3 |
| Neutrophils ($10^3$/mm$^3$) | 7.2 ± 1.4 | 9.7 ± 3.8 | 10.8 ± 3.0 | 16.5 ± 1.7* |
| Eosinophils ($10^3$/mm$^3$) | 0.16 ± 0.04 | 0.62 ± 0.2 | 0.92 ± 0.3 | 0.4 ± 0.8 |
| Lymphocytes ($10^3$/mm) | 4.2 ± 1.0 | 5.8 ± 0.6 | 6.9 ± 1.7 | 7.9 ± 0.8** |
| Monocytes | 0.32 ± 0.09 | 0.32 ± 0.09 | 0.43 ± 0.2 | 0.64 ± 0.81 |

The elements of the erythrocyte series did not change significantly (increased or reduced) compared to the controls in the blood tests (Table D), reflecting the non-activation of the cell precursors of these bone marrow elements by the compound.

Conclusion: The histological findings of the bone marrow tissues of *Cebus apella* monkeys (Table D) that did not have any previous illness, show that the biological response modifier (proteic aggregate of ammonium and magnesium phospholinoleate-palmitoleate anhydride) can stimulate, in the bone marrow of animals treated with the product, the growth and differentiation of neutrophils and lymphocytes in progenitor cells, with the consequent increase of these elements in peripheral blood, which can be seen in blood tests of the animals done at the end of the experiment.

Results: Evolution of the mean body weight

TABLE P

Evolution of the mean body weight (30 days)

| | Controls (C) NaCl (0.9%) 30 days N = 4 | LD Group 5 mg/kg/ day × 30 days N = 4 | MD Group 10 mg/kg/day × 30 days N = 4 | HD Group 30 mg/kg/day × 30 days N = 4 |
|---|---|---|---|---|
| Initial weight | 2.6 kg | 2.3 | 2.7 | 3.2 |
| Final weight | 2.7 kg | 2.5 | 2.9 | 3.1 |
| (Variation (weight) and variation %). | 100 gr (3.8%) | 200 gr (8.6%) | 200 gr (7.4%) | −100 gr (3.1%) |

Discussion: Except for the group given the highest dose (HD—30 mg/kg) of the biological response modifier, which had an average weight loss (−3.1%—Table P), all the other animals in the study groups had a significant average weight gain (Table P: LD=+8.6% and MD=+7.4%), that is, mean final weight compared to the mean initial weight, if compared to the mean weight of the control group animals (C—Table P) that were injected with saline solution (NaCl 0.9%) in the same period.

The aforementioned experiments conducted in a species phylogenetically close to humans show that the use of the biological response modifier (proteic aggregate of ammonium and magnesium phospholinoleate-palmitoleate anhydride), even at high concentrations, does not have any toxic effect on the average body weight of the animals.

On the contrary, a preliminary indication that the compound could act in the mechanisms involved in the control of satiety and/or creation of body mass is suggested by the experiment, though healthy animals were used.

The small weight loss in the group that received the highest dose (30 mg/kg—Table P) in relation to the initial weight possibly reflects a higher level of stress in the animals of this group, caused by the greater amount of the compound inoculated intramuscularly. The greater the amount of compound injected, the more intense is the pain caused by the repeated intramuscular injections.

The small average weight gain of the control group (+3.8%—Table P) after 30 days of the experiment is possibly due to the fact that the animals were given plenty of food during the experiment and also because they were confined (individual cages), which reduced the expenditure of energy, resulting in weight gain.

Animal Experiments—Practical Example of the Use of the Present Invention for the Correction of Problems Associated to the Current Treatments—Neutropenia and Opportunistic Infections Histological findings for the bone marrow tissues of *Cebus apella* monkeys (Table D), in the experiment cited in the present report (Table D) show that the biological response modifier (proteic aggregate of ammonium and magnesium phospholinoleate-palmitoleate anhydride) is able to stimulate in the bone marrow of healthy animals treated with the product the growth and differentiation of neutrophils and lymphocytes of progenitor cells, with the consequent increase of these elements in the peripheral blood expressed in their number in the blood tests of animals at the end of the experiment.

That is, the compound (proteic aggregate of ammonium and magnesium phospholinoleate-palmitoleate anhydride) when used isolated has clearly induced a dose-dependent increase in the populations of neutrophils and lymphocytes in the peripheral blood of the monkeys that did not have any previous illness at the time they were treated with the compound, compared to the controls (Table D).

Extrapolation of the Results for Use in the Invention

The biological response modifier (proteic aggregate of ammonium and magnesium phospholinoleate-palmitoleate anhydride) has already been reported in the state of the art as able to induce the increase in the stimulation factors of the myeloid lineage in healthy mice and Ehrlich carcinoma-bearing mice (PI—0305373-3, U.S. Ser. No. 10/978,683, EPA 0426250.3.2405), which is partially reproduced below:

"PI—0305373-3: (A dose-dependent increase in the number of precursor cells of granulocytes-macrophages in the bone marrow (CFU-GM) of Balb/c mice, both normal and intraperitoneally inoculated with Ehrlich ascites tumor was observed with subcutaneous treatment for 7 days, with doses of the compound that is the object of the present invention varying from 0.5 to 5.0 mg/kg. The dose of 5.0 mg/kg administered for a 7 day period, before or after tumor inoculation, was particularly effective in modulating myelopoiesis in tumor-bearing mice. At the same time, the same treatment protocol has significantly reduced the number of CFU-GM in the spleen and also the splenomegaly of animals inoculated with Ehrlich ascites tumor. The compound of the present invention had no in vitro effects on the growth and differentiation of precursor cells of granulocytes-macrophages of the bone marrow from normal Balb/c donor mice. These findings clearly indicate that the compound that is the object of the present invention maximizes the immune regulatory mechanisms of bone marrow precursor cells, which are involved in the control of the changes caused by the tumor in the blood-lymphpoietic system of the host—PI—0305373-3"

Therefore, the state of the art reports an action of the biological response modifier (proteic aggregate of ammonium and magnesium phospholinoleate-palmitoleate anhydride) when used alone, on the tumor mechanisms involved in the differentiation of precursor cells of the bone marrow of healthy and Ehrlich carcinoma-bearing mice. (PI—0305373-3, U.S. Ser. No. 10/978,683, EPA 0426250.3.2405).

In order to confirm the action of the biological response modifier (proteic aggregate of ammonium and magnesium phospholinoleate-palmitoleate anhydride) on precursor cells of leukocytes in the bone marrow, a new series of experiments suitable for the purposes of the present invention was conducted with an animal species phylogenetically close to humans, that is, *Cebus apella* monkeys. The results from the blood tests of these animals are shown in Table D.

Based on the ability detected in the biological response modifier of inducing the activation of precursor cells of the bone marrow on healthy animals (monkeys, Table D), and also in healthy and Ehrlich carcinoma-bearing Bal/c mice, a different and innovative practical use of the biological response modifier (proteic aggregate of ammonium and magnesium phospholinoleate-palmitoleate anhydride) has been made available, according to the needs of invention, that is:

The practical use of the biological response modifier (proteic aggregate of ammonium and magnesium phospholinoleate-palmitoleate anhydride) in the association or combination of drugs and/or treatments that characterize the present invention, that is, the incorporation of the biological response modifier (proteic aggregate of ammonium and magnesium phospholinoleate-palmitoleate anhydride) in the invention, for the treatment of patients affected by chronic systemic diseases such as cancer, not only with the purpose of improving the antitumor effectiveness of the combination or association, but also providing it with a different and innovative therapeutic property that has not been described in the state of the art: The biological response modifier (proteic aggregate of ammonium and magnesium phospholinoleate-palmitoleate anhydride) will be used in the present invention for reversal or minimization of immunosuppression and neutropenia in this particular type of patients or diseases, which are aggravated by cytotoxic and/or myelosuppressive treatments in clinical practice.

This new therapeutic usefulness added to the invention is of utmost importance in the of medicine, since virtually all patients affected by these diseases undergo treatments that include a wide range of immunosuppressive and/or myelosuppresive and/or myelotoxic drugs and/or therapies, e.g. chemotherapy and/or radiotherapy, and, thus, are at high risk of developing immunosuppression and neutropenia associated or caused by such treatments.

The association or combination of the biological response modifier (proteic aggregate of ammonium and magnesium phospholinoleate-palmitoleate anhydride) specially selected as a component of associations or combinations of drugs and treatments, which characterizes the present invention, now for new and different purposes, that is, to make it possible in practice that the referred association or combination is able to minimize or correct immunosuppression and neutropenia caused by other drugs and/or treatments, besides the maximized therapeutic effects against the primary disease (cancer), not only is an inventive activity, but also confers a new and remarkable ability to the present invention not described in the state of the art, also for the biological response modifier (proteic aggregate of ammonium and magnesium phospholinoleate-palmitoleate anhydride).

In the state of the art in PI—0305373-3 U.S. Ser. No. 10/978,683 e EPA 0426250.3.2405 the descriptions of the immunological effects of the biological response modifier concern only its effect when used alone as a immunomodulator in experiments with healthy and Ehrlich carcinoma-bearing animals, which is totally different from the present invention that uses the referred compound for a new and entirely different practical application, that is, for the treatment of myelosuppression and neutropenia, when used in the form of associations or combinations with other drugs and/or treatments.

Moreover, the ability of correcting or minimizing the immunosuppressive effect provided by the invention, due to the presence in the association or combination of the biological response modifier (proteic aggregate of ammonium and magnesium phospholinoleate-palmitoleate anhydride) is much wider than the combinations currently available or reported in the state of the art for other biological response modifiers used in adjuvant immunotherapy, associated to chemotherapy drugs for similar purposes, e.g. stimulators of the myeloid series (G-CSF and GM-CSF) able to stimulate only the proliferation of neutrophils, whereas the present invention, due to the presence of the biological response modifier and its distinct properties, can not only stimulate an increase in the neutrophil population, but also the production of lymphocytes.

Based on current data obtained with the use of the biological response modifier (proteic aggregate of ammonium and magnesium phospholinoleate-palmitoleate anhydride) used alone in healthy animals (Table D) and animals with cancer treated only with the cited compound (PI—0305373-3 U.S. Ser. No. 10/978,683, EPA 0426250.3.2405,), a new and entirely different use of the compound was provided, that is:

The invention has included the biological response modifier (proteic aggregate of ammonium and magnesium phospholinoleate-palmitoleate anhydride) in the combination or association of treatments and drugs, not only to maximize the antitumor effect, but also and in an innovative way, with the purpose of effectively treating, concomitantly or simultaneously, immunosuppression and neutropenia of patients that in the course of treatment of this type of diseases are or should be using immunosuppressive and/or cytotoxic drugs and/or treatments, as shall be demonstrated by practical examples in the present report.

It is well known to anyone with reasonable knowledge of the state of the art that almost all patients undergoing cancer treatment use cytotoxic and/or immunosuppressive treatments and drugs that lead to the usual adverse effects, particularly neutropenia and/or its most severe manifestation, febrile neutropenia, as described in the present report, which can be prevented or minimized with the use of the present invention.

This remarkable ability of the present invention, that is, its action on the cancer process and the simultaneous ability of treating immunosuppression and neutropenia mainly associated with the use of cytotoxic and/or immunosuppressive compounds offers a significant comparative advantage when the invention is used in clinical practice compared to the associations of drugs and/or treatments available in the state of the art that do not include the biological response modifier in their formulations and/or chemotherapy and/or treatment protocols.

For illustrative purposes, if the biological response modifier (proteic aggregate of ammonium and magnesium phospholinoleate-palmitoleate anhydride) is associated to a hypothetic cytotoxic drug, called drug (X) in a hypothetical drug formulation, but that can be used in clinical practice and according to the object of this invention, not only its use (in the form or an association or combination) will be more effective to treat cancer with the (X) drug, as shown in examples of the present report (Table A, Table B and Table C) than the isolated use of the (X) drug, but also the use of the invention, that is, the biological response modifier associated to the cytotoxic drug (X) will concomitantly or simultaneously make it possible to prevent or minimize neutropenia caused by an adverse and undesirable side effect produced by the cytotoxic properties of the drug (X) if used alone, as it shall be demonstrated through practical example, as follows.

To obtain a similar effect, that is, reversal or minimization of neutropenia, in the current state of the art the (X) drug could be used, for example, with other compounds able to stimulate the production of neutrophils, such as myelopoiesis inducing compounds (C-CSF or GM-CSF). However, this would imply higher costs and lower therapeutic effects against the primary illness, since the association of the biological response modifier (proteic aggregate of ammonium and magnesium phospholinoleate-palmitoleate anhydride) with the drug (X) has a higher therapeutic effect against the neoplasia than the isolated use of drug (X), as it has been shown in the present report through practical examples (Table A, Table B, Table C).

In order to demonstrate in practice that the desired effect of the invention, that is, prevention and/or correction of immunosuppression, which has an impact on the production of the white blood cells in peripheral blood, particularly neutrophils and lymphocytes, occurs in the presence of chronic systemic disease (cancer), and more importantly for the purposes of this invention, when patients receive cytotoxic and myelosuppressive drugs, some examples of the use of the present invention in an animal model (Table L) and a clinical assay involving patients with cancer using several immunosuppressive and cytotoxic drugs (chemotherapy and radiotherapy) that aggravate other clinical conditions, such as cachexia, are provided (Table H and Table M).

Moreover, the referred example that concerns the use of the invention for the treatment of human patients will show the remarkable possibility of using the invention against one of the most important causes of morbidity of chronic systemic diseases such as cancer, associated to the primary disease and/or aggravated by the current state of the art treatments, namely: the morbid medical condition characterized by rapid weight loss that is associated to cancer and/or its treatments called cachexia.

The examples cited in this report are merely illustrative and do not intend to limit the scope of the present invention.

Use of the Invention—Practical Examples—Immunosuppression and Neutropenia—Animal Models Animals: 3-week-old C57B1/6 female mice were used in all the experiments.

Tumor: Lewis lung carcinoma (3LL) was the tumor selected for all the in vivo assessments (Table A, Table B, Table C) in these experiments, with the cells maintained in culture medium and inoculated subcutaneously in the animals at the concentration of 6×10$^5$ cancer cells (3 LL) for each animal.

Chemotherapy drugs and doing used: vindesine sulfate (3 mg/kg) and cisplatin (1 mg/kg) intraperitoneally, 3 times a week for 4 weeks.

Biological response modifier and dosing: Proteic aggregate of ammonium and magnesium phospholinoleate-palmitoleate anhydride (0.5 mg/kg), intraperitoneally, 3 times a week for 4 weeks.

The data from this experiment is shown in Table L, which is part of the present report.

Experimental Design:

A batch of 40 animals (Table L—group A) inoculated with 3 LL tumor cells (6×105 cells/animal), was treated with the vindesine sulfate (3 mg/kg) and cisplatin (1 mg/kg) compounds administered together by intraperitoneal injection 24 hours after tumor inoculation, in 3 weekly cycles, during 4 weeks. The animals were followed up for 30 days (Table L—Group A).

Of these animals, 10 were sacrificed in the beginning of the experiment prior to tumor inoculation and administration of the compounds (Table L—control group) for the establishment of the reference values for the white blood cells (leukocyte count) and the other 30 animals were treated and followed up until the end of the experiment (30 days), when they were also sacrificed for blood collection.

Another batch of 40 animals (Table L—Group B) inoculated with 3 LL cells (6×105 cells/animal), was treated with 0.5 mg/kg/day of the proteic aggregate of ammonium and magnesium phospholinoleate-palmitoleate anhydride and vindesine sulfate (3 mg/kg) and cisplatin (1 mg/kg), administered together by intraperitoneal injection 24 hours after tumor inoculation, in 3 weekly cycles, for 4 weeks. The animals were followed up for 30 days (Table L).

Of these animals (Table L—Control group), 10 were sacrificed in the beginning of the experiment prior to tumor inoculation and the administration of the compounds for the establishment of the reference values for the white blood cells (leukocyte count) and the other 30 animals were treated and followed up until the end of the experiment (30 days), when they were also sacrificed for blood collection.

Blood samples of the two groups (Group A and Group B) were obtained by puncturing the orbital plexus of the animals at the appropriate collection periods.

Leukocyte counts were made in the peripheral blood of the treatment and control animals, in the beginning and at the end of the experiment.

The global count of cells was performed by automated methods using a Coulter counter—STKS model.

The specific and differential count of leukocytes was made in Giemsa-stained blood smears, (total 100 cells).

Results: Leukocyte count—(Table L)

Discussion of the results:

TABLE L

| ×10³ cells/mm³ | Leukocyte count | | |
|---|---|---|---|
| | Group C (controls) No of animals = 20 | Group A No of animals = 30 | Group B No of animals = 30 |
| Collection period (days) | 10 | 30 | 30 |
| Leukocytes | 15.80 ± 4.8 | 14.2 ± 4.0 | 18.3 ± 2.2 |
| Lymphocytes × 10³ | 14.6 ± 3.9 | 13.8 ± 3.7 | 17.8 ± 4.1 |
| Neutrophils × 10³ | 0.95 ± 0.8 | 0.26 ± 0.9 | 1.6 ± 0.6 |
| Monocytes × 10³ | 0.1 ± 0.1 | 0.3 ± 0.1 | 0.2 ± 0.1 |
| Eosinophils × 10³ | 0.0 ± 0.0 | 0.0 ± 0.0 | 0.3 ± 0.1 |
| Basophils × 10³ | 0.1 ± 0.1 | 0.0 ± 0.0 | 0.0 ± 0.0 |

As expected, the use of vindesine and cisplatin has shown a depressant effect on the number of neutrophils measured in the peripheral blood of the animals that were given these substances. (Table L—Group A) compared to the control animals (Table A—Group C).

It can be seen that the animals that used the present invention (Table L—Group B), that is, the association or combination of cytotoxic drugs (vindesine+cisplatin) with the biological response modifier (proteic aggregate of ammonium and magnesium phospholinoleate-palmitoleate anhydride) showed a number of neutrophils in the peripheral blood comparatively much higher than those found in the group that used the combination of cytotoxic drugs (Table L—Group A), and is also higher than the number of neutrophils in the control group (Table L—Group C).

It can also be seen that the number of lymphocytes in the peripheral blood of Group B—Table L, that is, the animals that used the invention is comparatively much higher than the number of lymphocytes of the animals of Group A—Table L that were only given the vindesine and cisplatin association (Group A—Table L), and is also higher than the number of these elements in animals of the control group (Group C—Table L).

Therefore, this practical experiment makes it possible to realize or demonstrate that the present invention, when used in the treatment of chronic systemic disease (cancer), that is, with the use of the biological response modifier (proteic aggregate of ammonium and magnesium phospholinoleate-palmitoleate anhydride) associated or combined with compounds with myelotoxic properties, is capable of reverting or minimizing neutropenia associated to the referred myelotoxic drugs.

The use of the present invention, which includes the biological response modifier (proteic aggregate of ammonium and magnesium phospholinoleate-palmitoleate anhydride) in treatment protocols that use cytotoxic and/or myelotoxic drugs or else in formulations of drugs, will not only make it possible to increase the number of circulating neutrophils, preventing or minimizing the additional use of myeloid lineage stimulating factors (G-CSF and GM-CSF), but also strongly stimulates the production of lymphocytes in the peripheral blood (Group B—Table L), which are also very important cells used by the immune system to fight infections and cancer. Such effect is not obtained with the use of G-CSF and GM-CSF, which only stimulate the production of neutrophils.

However, the use of the invention, that is, the biological response modifier (proteic aggregate of ammonium and magnesium phospholinoleate-palmitoleate anhydride) associated to chemotherapy drugs in the case, was found in clinical practice to induce the maintenance and/or correction of the immunological ability expressed by the increased number of neutrophils, and even more surprisingly, of lymphocytes, in the presence of cancer, associated to the use of chemotherapy drugs known to be immunosuppressive (vindesine sulfate).

A clinical trial using humans for the demonstration of the remarkable abilities of the invention for the preventive, curative or palliative treatment of cancer and some of its most serious complications, that is, immunosuppression and neutropenia, and also the so-called anorexia-cachexia syndrome or cachexia is described for illustrative purposes only.

Use of the Invention—Practical Example—Experiments with Humans—Immunosuppression and Neutropenia—Anorexia-Cachexia Syndrome (Table H and Table M)

Besides the immunosuppression and neutropenia that occur in chronic systemic diseases and are usually aggravated by the use of immunosuppressive and cytotoxic drugs and/or treatments, another adverse clinical condition called anorexia-cachexia syndrome (ACS), or simply cachexia, occurs in cancer patients, and is also associated with immunological and inflammatory factors, as well as other factors caused by tumor-host interaction, and which may also be aggravated by the drugs and treatments used.

As extensively explained in the present report the so-called anorexia-cachexia syndrome (ACS), or else cachexia, is a serious multi-factor pathological condition that involves, among other factors, increased energy consumption by tumor cells, release of mechanisms that control satiety reducing food intake, the cytokines produced by tumor and host cells and the associated inflammatory reactions that can be related to metabolic abnormalities typical of the referred syndrome, which is characterized by the progressive and irreversible depletion of muscle and fat tissues, causing several complications.

Cachexia is considered one of the causes that contribute to treatment failure and one of the main factors that influence the high rate of mortality associated to chronic systemic diseases such as cancer. As also explained in the present report, cachexia can be classified into primary or secondary: Primary cachexia, which is related in the current state of the art to the metabolic and/or immunological consequences of the presence of the tumor associated to changes in the inflammatory response of the host organism.

As for secondary cachexia, it can result from reduced nutrient intake and absorption due to obstructions of the gastrointestinal tract caused by cancer, anorexia caused by the treatment and massive bowel resections. The low food intake may also be related to adverse reactions to cancer treatment, such as nausea and vomiting due to cytotoxic drugs, which reduce the appetite, particularly mucositis and enteritis caused by cytotoxic chemotherapy and radiotherapy, in a non-exhaustive list.

It is widely recognized in the state of the art that the use of cytotoxic drugs or other treatments can damage not only cancer cells, which are the desired targets, but also reach healthy cells with a high renewal rate indiscriminately, and, among these, cells of the gastrointestinal epithelium, causing a clinical pathological called mucositis.

Mucositis, a pathological condition characterized by significant changes in the oral and intestinal epithelium, caused by several mechanisms associated to the inflammatory response in the body of the patient under treatment, adversely affects the ability to absorb nutrients and, consequently, is often cited as a cause of secondary cachexia or an important factor for its aggravation. For an example of the state of the art, please see: Sonis S T 2004—The pathobiology of mucositis. Nat Rev Cancer 4:277-284 e ainda; Sonis S T, Elting L S, Keefe D, Peterson D E, Schubert M, Hauer-Jensen M, Bekele B N, Raber-Durlacher J, Donnelly J P, Rubenstein E B 2004 Perspectives on cancer therapy-induced mucosal injury: pathogenesis, measurement, epidemiology, and consequences for patients. Cancer 100:1995-2025.

For this reason, oral and gastrointestinal mucositis are frequent complications of antitumor drug or radiation therapy, which may interfere with the effectiveness of the treatments by, among other things, reducing the doses of chemotherapy drugs or radiotherapy, and may also increase the cost of treatment, impairing the quality of life of patients.

The two conditions (primary and secondary cachexia) often occur together in one individual or patient, since virtually all patients with such chronic diseases are given cytotoxic or aggressive drugs for, such as radiotherapy and others. Thus, besides primary cachexia that is caused by the disease itself, cachexia secondary to cancer treatment that includes aggressive therapeutic interventions used in the current state of the art may also occur.

The current state of the art treatments for cachexia, or else, anorexia-cachexia syndrome (ACS), both primary and secondary, are represented by the so-called nutritional therapy and some classes of compounds or drugs, already described in the present report and briefly detailed below.

Nutritional therapy or treatment of the states of anorexia-cachexia frequently involves the use of special nutrients, e.g. polyunsaturated fatty acids (PUFAs) such as the eicosapentaenoic acid (EPA) and the doxosahexaenoic acid (DHA), the aminoacids glutamine, arginine and the nucleotides used in nutritional products and dietary supplements, due to their nutritional properties and also because they act as immunomodulators (glutamine, arginine).

As shown in the present report, some types of compounds or drugs are also used in the treatment of primary and secondary cachexia, including, among others: Non-steroidal anti-inflammatory drugs (megestrol acetate, ibuprofen), steroidal anti-inflammatory drugs (hydrocortisone, cortisone, corticosterone, dexamethasone, betamethasone, prednisolone, prednisone, methylprednisolone, budesonide, beclomethasone), derivatives of tetrahydrocannabinol (dronabinol), enzyme inhibitors (eicosapentaenoic acid, hydrazine sulfate), hormones (melatonin, somatropin) epithelial or mucosal protectors (sulfacrate) and others.

As also widely described and demonstrated in the present report, the biological response modifier (proteic aggregate of ammonium and magnesium phospholinoleate-palmitoleate anhydride) can modulated the immune response (Table C), both isolated and associated with other compounds used in the treatment of chronic systemic diseases such as cancer (Table A, Table B) and it is known that the modulation of immune response can be useful in the treatment of anorexia-cachexia, because of the use in the state of the art of compounds that modulate the inflammatory response in the treatment of chronic systemic diseases such as polyunsaturated fatty acids (PUFAs).

Also, the biological response modifier (proteic aggregate of ammonium and magnesium phospholinoleate-palmitoleate anhydride) contains aminoacids used in the state of the art in several formulations, as already mentioned in the present report, for the treatment of patients with the anorexia-cachexia syndrome (ACS) or cachexia, including arginine (Arg). For the qualitative and quantitative distribution of the constituents of the biological response modifier, please see: (PI—0305373-3 U.S. Ser. No. 10/978,683, EPA 0426250.3.2405).

The biological response modifier (proteic aggregate of ammonium and magnesium phospholinoleate-palmitoleate anhydride) also contains linoleic acid (PI—0305373-3 U.S. Ser. No. 10/978,683, EPA 0426250.3.2405) which is a polyunsaturated fatty acid (or PUFA), belonging to the same class or type of fatty acids that are specially selected in the state of the art as constituents of some types of formulations used in the nutritional therapy for the treatment of cachexia, or else they are isolated used as a drug for the same purpose, as it is described in the present report.

The present report contains new and important information that demonstrate that the biological response modifier (proteic aggregate of ammonium and magnesium phospholinoleate-palmitoleate anhydride) is also a ligand (agonist) for toll-like cell receptors (Table T1 and Table T-2).

Stimulants for toll-like receptors are mentioned in the current state of the art as having an essential role or participation in several mechanisms responsible for the repair of cell damage and in cell regeneration, including epithelial tissues that are known to be affected or impaired by cytotoxic treatments and compounds. For illustrative purposes of the most recent state of the art, please see: Michelsen, K. S. & Arditi, M. Toll-like receptors and innate immunity in gut homeostasis and pathology. Curr. Opin. Hematol. 14, 48-54 (2007) and Toll-like receptors and cancer—Seth Rakoff—Nahoum and Ruslan Medzhitov—Nature—Reviews—Cancer—January 2009-vol. 9.

Also, there are new data and preliminary experimental indications in the present report (Table P) according to which, when the compound was used in non-human primates a mean weight gain was detected in the animals that used the biological response modifier (proteic aggregate of ammonium and magnesium phospholinoleate-palmitoleate anhydride) during the experiment, suggesting an anabolic effect for the compound, though the animals were healthy.

Finally, based on the practical experiments with hamsters that were given the carcinogenic compound called dimethylbenzanthracene (DMBA) contained in the present report, and also on clinical trials on humans suffering from cervical dysplasia associated to the human papilloma virus or HPV (Table P-1 and Table P-2), it can be affirmed that the compound can effectively repair cell damage in the inner and outer layers of the epithelium, that is, favoring the regeneration of cells with damage similar to the one caused by cytotoxic compounds and treatments, e.g. damage caused to the epithelium of the gastrointestinal tract.

In the case of the practical experiment in hamster, where the aggressive and carcinogenic is the DMBA, it must be stressed that this carcinogenic agent alone can cause extensive damage to the epithelial cells, producing intense local inflammatory reaction, regardless of its carcinogenic role.

Since it is accepted in the state of the art that the so-called anorexia-cachexia syndrome (ACS), or cachexia, is caused by, among other things, immunological factors involved in inflammatory processes produced by the tumor-host interaction, and that primary cachexia can be further aggravated, for example, by inflammatory responses of anticancer chemotherapy, particularly when cytotoxic drugs and other therapeutic interventions that damage the inner epithelial tissues such as radiotherapy are used, it can be seen that most current curative or palliative treatments for this pathological condition involve nutritional replacement therapies and/or the use of aminoacids and fatty acids with anti-inflammatory and/or immunomodulatory action, and also some classes of drugs such as steroidal and non-steroidal anti-inflammatory compounds: The purpose here is to provide at least a minimum level of protection to the patient, although indirect and/or palliative.

Evidently, all the agents and therapies cited in the present report, regardless of their actual effectiveness, should be used as adjuvant therapy, that is, for the preventive, curative or palliative treatment of primary and secondary cachexia, an adjuvant therapy should be adopted only to fight or treat primary and/or secondary cachexia with the use of the referred compounds, and it is not uncommon that more than one type of such anti-cachexia treatments or compounds are used in association or combination for the same patient.

Of course, this is not an ideal situation. Given that the control of primary and/or secondary cachexia is undeniably an important factor for a favorable outcome of the disease, for increasing the effectiveness of treatments and at the same time reducing its undesirable toxicity, and finally improving the quality of life of patients. Therefore, it is highly desirable that new products, preferably with a broad spectrum of activity, are available to face all the problems associated to the disease (primary cachexia), as well as the problems usually caused and/or aggravated by the treatments used in the state of the art to fight cancer (secondary cachexia).

In view of all the biological properties previously cited in the present report, regardless of their recognized immunomodulatory ability, presence of aminoacids and polyunsaturated fatty acids (PUFAs) in their molecular formula, which are used in the treatment of cachexia, the modulatory properties of inflammation and/or cellular repair and regenerative properties possibly associated to the presence of toll-like cell receptors, and more importantly, the remarkable abilities or properties for the protection and/or regeneration of cells of the inner and outer layers of the epithelial tissue, shown in practical examples in the present report, the biological response modifier (proteic aggregate of ammonium and magnesium phospholinoleate-palmitoleate anhydride) was specially selected as part of this invention with the specific purpose of providing an adjuvant therapy in primary cachexia and/or secondary cachexia.

The referred selection and its practical effects on the treatment of cachexia, as shall be explained in this report, is undoubtedly an innovative use of this compound, that has not been described in the state of the art until now, either for the biological response modifier (proteic aggregate of ammonium and magnesium phospholinoleate-palmitoleate anhydride) alone, or for the effect of its association or combination with other treatments and compounds to fight cancer and concomitantly and/or simultaneously in cachexia. This new practical application incorporated or provided by the present invention can by no means be considered a simple or obvious consequence of the state of the art.

Practical Example of the Use of the Invention for Reversal of Immunosuppression and Cachexia A practical example of the use of the present invention in cancer patients is provided, that is, the use of the biological response modifier (proteic aggregate of ammonium and magnesium phospholinoleate-palmitoleate anhydride) in a clinical trial, where the referred compound was associated to chemotherapy and radiotherapy protocols, in a comparative assessment (control group).

This example shall include data on the evolution of the main elements of the white blood cells, through blood tests (Table H), and also the evolution of body weight (Table M), to demonstrate in practice the innovative and remarkable properties of the invention in the prevention or treatment of immunosuppression and neutropenia, and also for the preventive, curative and palliative treatment of cachexia.

Objectives of the Clinical Trial:

(A) Assess in clinical trial on cancer patients receiving cytotoxic chemotherapy and/or radiotherapy, the effect of the invention on the leukocyte series, with the purpose of demonstrating its usefulness for the prevention and/or reversal of immunosuppression and neutropenia, and consequently minimizing or avoiding the occurrence of infections caused by cytotoxic chemotherapy and/or radiotherapy.

(B) Assess in clinical trial with patients receiving cytotoxic chemotherapy and/or radiotherapy, the effect of the invention on the evolution of body weight to demonstrate its usefulness in the preventive, curative or palliative treatment of cachexia or the anorexia-cachexia syndrome in the referred patients.

Experimental Protocol

A group of 85 cancer patients using chemotherapy and/or radiotherapy was selected for the use of the present invention, that is, the combination or association of the biological response modifier (proteic aggregate of ammonium and magnesium phospholinoleate-palmitoleate anhydride) with at least one other cancer treatment, that is, a combination or association with chemotherapy and/or radiotherapy (Group A and Group B) and compared to patients who received only the standard drugs in the state of the art (Group C).

The patients of the present study had solid tumors and have been given at least one type of cytotoxic/myelotoxic drug in association with other non-drug treatments (radiotherapy) or were treated with protocols of cytotoxic/myelotoxic drugs.

The patients treated by radiotherapy (RT) were given also at least one type of myelotoxic drug.

Associated drugs or protocols of chemotherapy drugs used in this clinical trial: EC (Etoposide+Cisplatin), VIP (Vinblastine+Ifosfamide), Cisplatin, VICE (Vincristine+Ifosfamide+Carboplatin+Etoposide), FCE (5-Fluoruacil+Cyclophosphamide+Epirubicin), DMCVB (Doxorubicin, Mitoxantrone, Cyclophosphamide, Vindesine and Bleomycin).

Clinical and laboratory follow-up: The patients of the three groups (A, B e C) were monitored through clinical tests, including weekly weight assessment and blood tests (complete blood count) with blood samples collected on the day immediately preceding the application of the biological response modifier, at the beginning of the cycles of treatment and at the end of the assessment period.

Hematological measurements: Leukocyte and erythrocyte counts were performed by using an automated counter.

Assessment of cachexia: The change in body weight is considered the most reliable marker for the analysis of the evolution of primary and secondary cachexia, including the assessment of the effect of specific drugs and therapies.

Therefore, all patients (Group A, Group B and Group C) were weighted on the Day immediately preceding (PI) the beginning of the application and then were weekly assessed until the end of the experiment, with the use of a precision mechanical scale.

The patients that participated in the clinical trial were divided into three groups:

Group A: Patients receiving chemotherapy (CT) and/or radiotherapy (RT) which was associated with the use of the (proteic aggregate of ammonium and magnesium phospholinoleate-palmitoleate anhydride) during the treatment period with CT and RT.

Number of patients: 25

Dose and dose regimen for all patients in Group A: 5 mg/m2/day in the form of suspension, using sterile saline solution as diluent (NaCl) at 0.9%. by intramuscular injection.

Duration of the protocol: 60 days

Group B: Patients that completed their initial cycles of chemotherapy (CT) and/or radiotherapy (RT) which was associated to the use of the biological response modifier (proteic aggregate of ammonium and magnesium phospholinoleate-palmitoleate anhydride) in the interval between the end and the beginning of the new cycles of CT and/or RT.

Number of patients: 30

Dose and dose regimen of the biological response modifier for all patients in Group B: 5 mg/m2/day in the form of suspension, using sterile saline solution as diluents (NaCl) at 0.9% by intramuscular injection.

Duration of the protocol: 60 days

Group C: The hematological and clinical parameters were obtained and analyzed, including the evolution of the body weight of 30 patients under cancer treatment, receiving the usual treatment that involves chemotherapy (CT) and/or radiotherapy (RT), without the use of the biological response modifier associated to the treatments, for comparison purposes (control group).

Number of patients: 30

Duration: 60 days

Practical Example—Results: Group A: Patients Using the Biological Response Modifier Associated to Chemotherapy and/or Radiotherapy Group A—TOTAL LEUKOCYTES (percentages): Of the 25 patients, 18 (72%) had higher leukocyte values compared to the initial leukocyte values, 6 (24%) had decreased values compared to the initial values. The values of one patient (4%) remained unchanged.

Group A—NEUTROPHILS (percentages): Of the 25 patients, 18 (72%) had higher values compared to the initial neutrophil values, 6 (24%) had lower values compared to the initial values of neutrophils. The values of one patient (4%) remained unchanged.

Group A—LYMPHOCYTES: (percentages): Of the 25 patients, 16 (64%) showed higher values compared to the initial values of lymphocytes, 3 (12%) had lower values compared to the initial values. The values of six of the 25 patients (24%) remained unchanged.

Group A—ERYTHROCYTES (percentages): There were no significant changes in the levels of erythrocytes and hemoglobin during the trial, assessed in the beginning (TI) and at the end (TF) of the experiment.

Practical Example—Results: Group B: Patients with Associated Use (Sequential) of the Biological Response Modifier after the End of the Initial Cycles of Chemotherapy and Radiotherapy.

Results

Groups B—TOTAL LEUKOCYTES (percentages): Of the 28 patients, 25 (90%) had higher leukocyte values compared to the initial values and 3 patients (10%) had lower values compared to the initial values.

Group—NEUTROPHILS (percentages): Of the 28 patients, 22 (around 78%) had higher neutrophil values compared to the initial values. In 5 patients (17%) there were lower values compared to the initial values and in only 1 of the 28 patients (3%) the values of neutrophils remained unchanged.

Group B—LYMPHOCYTES: (percentages): Of the 28 patients, 24 (85%) had higher lymphocyte values compared to the initial values. In 4 of the 28 patients (15%) there were lower values compared to the initial values.

Group B—ERYTHROCYTES (percentages): No significant changes in the levels of erythrocytes and hemoglobin were detected during the trial, assessed in the beginning (TI) and at the end (TF) of the experiment.

Practical Example—Results: Group C: Patients Using Chemotherapy (CT) and/or Radiotherapy (RT) not Associated TI the Biological Response Modifier.

Results

Groups C—TOTAL LEUKOCYTES (percentages): Of the 30 patients, 3 (10%) had higher values of leukocytes compared to the initial values and 21 patients (70%) had lower values compared to the initial values. The leukocyte values of de 6 (20%) patients remained unchanged.

Group C—NEUTROPHILS (percentages): Of the 30 patients, 28 (93%) had lower values of neutrophils compared to the initial values, and of these patients, 4 (14%) had severe neutropenia, that is, a neutrophil count of less than 900 per cubic millimeter accompanied by fever (febrile neutropenia), though without the identification or location of the infectious focus. The neutrophil values of 2 patients (7%) remained unchanged.

Group C—LYMPHOCYTES: (percentages): Of the 30 patients, 4 (13%) had higher values of lymphocytes compared to the initial values. In 21 of the 30 patients (70%) there were lower values compared to the initial values. The lymphocyte values of 5 patients (17%) remained unchanged.

ERYTHROCYTES (percentages): No significant changes were found in the levels of erythrocytes and hemoglobin during the trial, assessed in the beginning (TI) and at the end (TF) of the experiment.

Episodes of Febrile Neutropenia Reported During the Observation Period

Of the 30 patients in Group C, 4 patients, all male individuals, (14%) had severe neutropenia, that is, a neutrophil count of less than 900 cubic millimeter and accompanied by fever (febrile neutropenia), though without the identification or location of the infectious focus Episodes of Infection Reported During the Observation Period:

Of the 30 patients in Group C, 3 of them, all male individuals, (10%) had episodes of s herpes simplex (HSV-1) of moderate intensity and 2 female patients (around 7%) had fungal infection of moderate intensity caused by *candida* sp. in the genital region, that is, 17% of the total number of these patients had episode of infection by opportunistic agents (Table H—Group C) during the observation period.

Treatment of the Episodes of Neutropenia and Infection

The patients with febrile neutropenia (Group C) were treated with the standard procedure, that is, prophylaxis using empirical intravenous antibiotic therapy.

The patients with herpes simplex (HSV-1) (Group C) were treated with acyclovir (injectable) and the patients with fungal infection were treated with Fluconazole.

TABLE H

Evolution of the leukocyte values per group of patients (Values in %)

|  | Final values higher than initial values | Final values lower than initial values | Final values unchanged | % of patients with gain or maintenance of the leukocyte values |
|---|---|---|---|---|
| TOTAL LEUKOCYTES | Group A: 72% | Group A: 24% | Group A: 4% | Group A: 76% |
|  | Group B: 90% | Group B: 10% | Group B: 0% | Group B: 100% |
|  | Group C: 10% | Group C: 70% | Group C: 20% | Group C: 30% |
| NEUTROPHILS | Group A: 72% | Group A: 24% | Group A: 4% | Group A: 76% |
|  | Group B: 78% | Group B: 17% | Group B: 3% | Group B: 81% |
|  | Group C: 0% | Group C: 93% | Group C: 7% | Group C: 7% |
| LYMPHOCYTES | Group A: 64% | Group A: 12% | Group A: 24% | Group A: 88% |
|  | Group B: 85% | Group B: 15% | Group B: 0% | Group B: 85% |
|  | Group C: 13% | Group C: 70% | Group C: 17% | Group C: 30% |
| FEBRILE NEUTROPENIA (%) | Group A: 0% |  |  |  |
|  | Group B: 0% |  |  |  |
|  | Group C: 14% |  |  |  |
| EPISODES OF IDENTIFIED INFECTION | Group A: 0% |  |  |  |
|  | Group B: 0% |  |  |  |
|  | Group C: 17% |  |  |  |

EVOLUTION OF BODY WEIGHT—GROUP A: Of the 25 patients, 15 (60%) showed positive change in body weight measured after 60 days compared to the initial weight. In 4 patients (16%) there was weight loss compared to the initial body weight. In 6 patients (24%), the weight remained unchanged.

EVOLUTION OF BODY WEIGHT—GROUP B: Of the 30 patients, 15 (50%) showed positive change in body weight measured after 60 days compared to the initial weight. In 2 patients (approximately 7%) there was a weight reduction compared to the initial weight. In 13 patients (approximately 43%), the weight remained unchanged.

EVOLUTION OF BODY WEIGHT—GROUP C: Of the 30 patients, 26 (approximately. 87%) had weight loss compared to the initial weight. In 4 (approximately 13%) patients the weight remained unchanged. None of the patients in this group gained weight compared to the initial values.

In GROUP C, 6 patients (20%) had weight loss greater than 10% compared to the initial values, which can be considered a criterion that characterizes the presence of cachexia or its aggravation.

TABLE M

Weight evolution by groups of patients (values in %)

|  | Final body weight greater than initial body weight | Final body weight lower than initial body weight | Final body weight equal to initial body weight | Percentage of patients with weight gain or weight maintenance | Percentage of patients with weight loss greater than 10% in the observation period |
|---|---|---|---|---|---|
| Group A | 60% | 16% | 24% | 84% | 0% |
| Group B | 50% | 7% | 43% | 93% | 0% |
| Group C | 0% | 87% | 13% | 13% | 20% |

Discussion of Results:

The use of the present invention provides remarkable results in clinical practice, and it has been demonstrated in animal experiments (Table L) and clinical trials in humans (Table H) that the use of the present invention, that is, the association or combination of the biological response modifier specially selected to be part of this invention (proteic aggregate of ammonium and magnesium phospholinoleate-palmitoleate anhydride) with other drugs or chemotherapy known to be cytotoxic and depressors of the myeloid series can correct and/or counterbalance its effects.

In the blood test of the animals (Table L) and in that of humans (Table H) that used the invention, not only an increased number of neutrophils, but also of lymphocytes, which are important components of the immune system that protect the body against invasion by infectious agents and also against cancers were found.

Another important observation concerning the purposes of the present report is that the use of this invention has produced a significant difference in the percentage of reported cases of febrile neutropenia and infection that affected the patients of group C, who did not use the invention, or else, of the total patients in Group C (100%), 14% were found to have febrile neutropenia and 17% of the patients in this group had one episode of infection characterized throughout the 60 days of treatments and observation.

Notably and surprisingly, compared to Group C, none of the patients who were treated with the invention (Table H—Group A and Group B) had severe neutropenia, febrile neutropenia or opportunistic infection during the period (60 days) of the trial, although 24% of the patients in Group A had lower values of neutrophils (Group A—Table H) than those in the beginning of the treatment and 17% of the patients of Group B had shown lower values of neutrophils (Group B—Table H) than those observed in the beginning of the clinical trial.

These data show that the use of the invention, through the presence of the biological response modifier (proteic aggregate of ammonium and magnesium phospholinoleate-palmitoleate anhydride) is able to counterbalance in practice the immunosuppressive effects of the treatments used in combination or association, that is, cytotoxic chemotherapy and radiotherapy combined with chemotherapy (Table H—Group A and Group B).

Additionally, the use of the invention in clinical practice has another advantage, which is the ability to stimulate the production of lymphocytes when compared to the use of other current therapeutic agents in the state of the art, and used in combination or association with chemotherapy and/or radiotheraopy treatments to revert or minimize neutropenia, the so-called myeloid series stimulating factors (C-CSF, GM-CSF) that have the ability to act in progenitor cells of the bone marrow to produce neutrophils. However, no cases of increase in the number of lymphocytes in the peripheral blood related to its use are reported in the state of the art.

One possible theoretical possibility suggested by the proven ability of connection of the biological response modifier to toll-like cell receptors, the so-called TLR-2 and TLR-4 (Table T-1 and Table T-2) is that the action of the biological response modifier (proteic aggregate of ammonium and magnesium phospholinoleate-palmitoleate anhydride) that is wider than that of myeloid series stimulating factors (C-CSF, GM-CSF) that is, the biological response modifier (proteic aggregate of ammonium and magnesium phospholinoleate-palmitoleate anhydride) might activate immune cells endowed with toll-like receptors (TLRs), such as macrophages and dendritic cells, which, in turn, would trigger the mechanisms that induce the stimulus to the production and differentiation of neutrophils from bone marrow precursors, as well as to lymphocyte proliferation and differentiation from the precursor cells in the bone marrow.

Another theoretical possibility to explain the additional capacity to induce lymphocytosis of the invention can be based on the proven ability of the biological response modifier (proteic aggregate of ammonium and magnesium phospholinoleate-palmitoleate anhydride) to attach itself or bind to toll like cell receptors (TLR-2 and TLR-4—Table T-1 and Table T-2), and once this binding is effected, the referred dendritic cells and macrophages are activated. Dendritic cells and macrophages are known to have these types of cell receptors in their surface and also antigen presenting cells that present antigens to T lymphocytes (T-4 lymphocytes or T-Helper), triggering the immune processes responsible for the differentiation and proliferation of the lymphocytes, elements extremely important in the fight against infections and cancer.

Regardless of the possible mechanisms of action, the effect or usefulness of any invention must be proven in practice and the clinical trial performed with humans has demonstrated in practice the remarkable effects of the present invention, which had already been demonstrated in animal experiments (Table L) of reverting or minimizing immunosuppression and neutropenia when administered to patients under cancer treatment using chemotherapy drugs (known to be myelotoxic) and radiotherapy (known to be immunosuppressive).

The adverse effects of chemotherapy and radiotherapy on the white blood cells evaluated in these patients through laboratory blood tests were avoided and/or reverted, since a marked increase in the number of neutrophils and lymphocytes was observed in the blood tests of patients of the groups (Table H—Group A and Group B) that used the present invention, that is, the biological response modifier (proteic aggregate of ammonium and magnesium phospholinoleate-palmitoleate anhydride) combined or associated to chemotherapy and radiotherapy compared to group (Table M—Group C) that did not use the present invention.

This laboratory effect on the white blood cells in patients that used the invention, that is, the biological response modifier (proteic aggregate of ammonium and magnesium phospholinoleate-palmitoleate anhydride) associated to chemotherapy and radiotherapy was also followed by remarkable and beneficial effects, since the episodes of febrile neutropenia and infection did not occur in the groups that used the invention (Group A and Group B—Table M) compared to the group (Group C—Table M) that did not use the invention.

The remarkable ability of the present invention constituted by the biological response modifier, in combination or association, of providing a preventive, curative or palliative treatment for immunosuppression and neutropenia caused by the use of cytotoxic and/or myelotoxic drugs was proven by the examples of experimental tests in animal models (Table L) and also by the effects in humans (Table M). This new practical application incorporated or provided by the present invention can by no means be considered a simple or obvious consequence of the state of the art.

Hence, the invention, that is, the biological response modifier (proteic aggregate of ammonium and magnesium phospholinoleate-palmitoleate anhydride) can be used in combination or association to prior, concomitant or subsequent treatment with various cytotoxic and/or myelotoxic compounds, drugs or treatments, which can be selected empirically at the time of treatment planning in practice, or even during the treatment, by adding, besides the increased anticancer effect conferred to the association or combination, the remarkable ability of treating immunosuppression and neutropenia in a preventive, curative or palliative character.

Also, when the invention is used in the manufacture of new drugs, in the form of associations or combinations, the presence of the biological response modifier (proteic aggregate of ammonium and magnesium phospholinoleate-palmitoleate anhydride) in the composition of such formulations, shall confer to the association or combination of drugs that include the invention, the same properties, that is, besides maximizing the anticancer effect of the association or combination, the invention shall concomitantly prevent, revert or minimize the immunosuppressive effect and/or neutropenia of any cytotoxic and/or myelotoxic drugs selected for use in association or combination with these new drugs.

Treatment of Cachexia—Discussion and Extrapolation of Data from the Clinical Trial (Table M).

Moreover, rapid weight loss, a sign usually associated to the presence of the malnutrition-cachexia syndrome or to the beginning of its manifestation or aggravation, was clearly prevented in the groups (Group A and Group B—Table M) compared to the control groups (Group C—Table M) during the experiment period.

On the contrary, in a remarkable way, 60% of the patients in the groups that used the invention (Group A-60%—Table M) and 50% (Group B—50%—Table M) had weight gain compared to the initial weight. Only 16% of these patients (Group A—Table M) and 7% (Group B—Table M), respectively, had a final body weight lower than the initial body weight. However, none of these patients had weight loss greater than 10% of the body weight compared to the initial weight in the beginning of the clinical trial.

In marked contrast with the group of patients subjected only to chemotherapy and/or radiotherapy without the use of the present invention (Group C—Table M), that is, of the biological response modifier used in association or combination (proteic aggregate of ammonium and magnesium phospholinoleate-palmitoleate anhydride), it can be seen in Table M that 87% of these patients had a final weight lower than the initial weight (Group C—Table M) (Group C—Table M) and finally 20% of these patients (Group C—Table M) were found to have a weight loss greater than 10% of the body weight compared to their initial weight, which characterizes the occurrence of cachexia.

None of the patients in Group C (Group C—Table M) had weight gain compared to the weight in the beginning of the experiment, and only 13% of these patients (Group C—Table M) maintained the initial body weight.

As it can be seen in Table M regarding weight gain or maintenance, with both parameters assessed in comparison with the initial levels, 84% of the patients in Group A (Group A—Table M) and 93% of the patients in Group B (Group B—Table M) maintained their weight or gained weight, whereas for Group C (Group C—Table M), only 13% of the patients maintained their initial body weight.

It should be noted that patients in all groups were being treated with protocols involving the combination of chemotherapy drugs and/or radiotherapy, with at least one anticancer drug, that is, all patients were receiving cytotoxic drugs, which could cause or aggravate, by local or systemic aggression, organic tissues and/or processes, thus contributing to additional weight loss in patients and because of the aggravation of cachexia (secondary cachexia).

In view of these remarkable results, it can be seen that the use of the invention prevented the weight loss that characterizes cachexia or its aggravation, which usually occurs with patients in cancer treatment and because of the drugs administered to treat this systemic disease, and thus, this invention can also be used in clinical practice for this purpose, that is, for the preventive, curative or palliative treatment of primary and secondary cachexia.

Hypothesis for the Anti-Cachectic Effect of the Invention

Given that it is a consensus in the state of the art that primary and secondary cachexia have a multifactorial origin, several concurring factors may help explain the remarkable effects of the present invention regarding weight maintenance and/or gain and the good status of patients in the groups that used the invention in this clinical trial.

The various hypotheses that can be formulated for the remarkable practical effect of this invention in the prevention or treatment of cachexia in the clinical trial, for illustrative purposes only, and without intending to limit the scope of the present invention, in view of the current state of the art scientific knowledge combined to the information on the biological properties of the components of the invention, and finally of the practical experiments contained in the present report, include maximization of anticancer effect by the invention, modulation of the immune response in the tumor-host interaction that is more beneficial for the patient, e.g., with reduced release of cytokines such as IL-6 and TNF, decrease in the reactive inflammatory response to the drugs and treatments administered and/or also the protection/restoration of epithelial tissues damaged by local or systemic side effects of cytotoxic treatments or drugs.

Besides the hypotheses mentioned, an additional factor can also be raised, again for merely illustrative purposes and understanding, once the capacity of reversion and/or minimization of immunosuppression and neutropenia observed in these patients produced by the present invention, as shown in Table H, may represent an additional benefit for the maintenance of a better overall clinical status of these patients, since the groups that used the invention (Group A and Group B—Table M) coincidentally were also those for whom the level of neutrophils and lymphocytes were maintained or increased, which may have also contributed to the good clinical status of patients, albeit indirectly through the inhibition of colonization of patients by opportunistic microorganisms.

It must be stressed that the group with greater incidence of immunosuppression and neutropenia, including episodes of febrile neutropenia and infection by opportunistic pathogens (Group C—Table H) is the same group of patients with the highest percentage of weight loss in the clinical trial (Group C—Table M), and 17% of the patients (Group C—Table M) had clear signs of primary and/or secondary cachexia.

Clinical Trial—Final Conclusions

Consequently, the biological response modifier (proteic aggregate of ammonium and magnesium phospholinoleate-palmitoleate anhydride) can be combined or associated to prior, concomitant or subsequent treatment with various cytotoxic and aggressive compounds, drugs or treatments administered during cancer treatment.

And these other drugs and/or treatments can be selected empirically at the time of treatment planning or even during treatment, in practice, adding in practice besides the increased anticancer effect conferred to the association or combination, the remarkable ability of providing preventive, curative or palliative treatment for immunosuppression and neutropenia.

Also, when the invention is used in the manufacture of new drugs for the treatment of chronic systemic diseases such as cancer, that is, in the form of associations or combinations, the presence of the biological response modifier (proteic aggregate of ammonium and magnesium phospholinoleate-palmitoleate anhydride) shall confer to the association or combination of drugs that contain the invention, the same properties, that is, besides maximizing the anticancer effect of the association or combination, the invention shall concomitantly prevent, revert or minimize the cytotoxic and/or aggressive effect that favors the aggravation of cachexia of any drugs selected for use in association or combination with these new drugs.

Finally, the invention, that is, the biological response modifier (proteic aggregate of ammonium and magnesium phospholinoleate-palmitoleate anhydride) can be used in clinical practice in the form of association or combination, for administration with prior, concomitant or subsequent treatment with various compounds used in the state of the art for the specific treatment of primary and secondary cachexia, and the referred anti-cachectic drugs and/or treatments can be selected empirically at the time of treatment planning or even during treatment, adding, in practice, besides the increased anticancer effect conferred to the association or combination, the remarkable ability of providing preventive, curative or palliative treatment for primary and secondary cachexia.

When the present invention is used in the manufacture of new drugs in the form of associations or combinations with other classes of anti-cachectic drugs, the presence of the biological response modifier (proteic aggregate of ammonium and magnesium phospholinoleate-palmitoleate anhydride) shall ensure that the association or combination of drugs containing the invention maximizes the effect of the new drug association for the preventive, curative or palliative treatment of primary and secondary cachexia.

It can be also affirmed that the administration of the invention to the groups that used it (Group A and Group B—Tables H and M) has provided, in practice, a double and remarkable beneficial effect, even in the presence of cytotoxic and/or myelosuppressive drugs and/or treatments, these being factors known in the current state of the art to aggravate cachexia, that is, the invention has clearly influenced the reversal or minimization of neutropenia and cachexia.

None of the participants in the clinical trial that used the present invention reported any additional adverse side effect that could be associated to the use of the invention, with most complaints related to clinical symptoms such as nausea and abdominal pain, which was expected given the cytotoxic medication and/or radiotherapy administered to all patients. However, these complaints were as frequent as those reported by patients in the group (Group C— Control) who has been given chemotherapy drugs and/or radiotherapy alone, without the present invention.

On the contrary, the patients in groups that used the invention have shown a remarkable improvement in the general clinical status at the end of the clinical trial, attested by the weight maintenance or gain in almost all these patients (Group A and Group B—Table P) and by complete absence of febrile neutropenia and opportunistic infection (Group A and Group B—Table H) when compared to the general clinical status of those patients who did not use the invention (Group C) at the end of the clinical trial.

The following topic refers to the use of the invention for cancer prevention preceded by a general review of the prior art for purposes of explanation and understanding of the invention.

Precancerous Lesions and Evolution of these Lesions to Cancer—State of the Art

It is well established in the state of the art that various types of tumors, particularly tumors of the skin, lung, digestive tract and cervix may originate or develop from precancerous lesions.

In the state of the art, these precancerous lesions are correlated to changes in normal cell populations caused by the chemical action of aggressive agents such as tobacco, alcohol and other toxic products considered inducers or promoters (carcinogens) of lung, upper and lower gastrointestinal and urinary bladder cancers, solar radiations as inducer-promoter of skin cancer (e.g. malignant melanoma, basal cell carcinoma, squamous cell carcinoma) and finally cellular changes caused by viruses, particularly the human papilloma virus—HPV (ex: cervical dysplasia, female cervical cancer and male genital cancer).

In the current state of the art it is of utmost importance that these precancerous lesions are identified early and the appropriate treatments are established for prophylactic and/or therapeutic purposes.

In addition to behavioral changes recommended for the elimination or minimization of risk factors and/or aggravation of these situations, e.g. elimination of smoking to prevent lung, gastrointestinal and urinary tract cancer, avoid unprotected sun exposure in the case of skin cancer, change patterns of sexual behavior in the case of the human papilloma virus (HPV) in the state of the art, some preventive and/or corrective therapies for these situations are available, which shall be described in the present report.

However, there is plenty of room for the development of new compounds and treatments, and a new option is the present invention, which, as will be shown in this report, presents novel and remarkable applications for this specific need, that is, the preventive treatment for cancer.

Also, practical examples are provided to help understand the novelty and usefulness of the present invention when used in cancer prophylaxis, that is, in the treatment of precancerous lesions, which are of high risk, since they may progress to cancer if left untreated.

These examples were produced for illustrative purposes only and do not intend to limit the scope of the present invention.

Treatment of Precancerous Epithelial External and Internal Lesions—State of the Art Skin cancer is the most common type of cancer today. In the US alone, estimates indicate that between 900,000 and 1,200.000 new cases of skin cancer (non-melanoma) are diagnosed each year. (Schuitmaker, J. J.; Baas, P.; van Leengoed, H. L. L. M.; van der Meulen, F. W.; Star, W. M.; van Zandwijk, N.; J. Photochem. Photobiol. 1996, B34, 3).

The most common precancerous skin lesions are actinic keratosis, which has a 10-25% chance of becoming malignant. For examples of the state of the art, we cite: Marks R, Foley P, Goodman G et al. Spontaneous Remission of Solar Kerotoses: the Case for Conservative Management. Br J Dermatol. 1986; 115:649-55, and also: Richard G, Gogau M D. Connexins: a Connection with the Skin Squamous Cell Carcinoma. Exp Dermatol Review. 2000; 9:77-96.

Sun exposure is the main environmental agent implied in actinic keratosis and induction of skin cancer. For an example of the state of the art, please see: Kripke M L. In: Fitzpatrick T B, Eisen A Z, Wolff K, Freedberg I M, Austen K F eds. Dermatology in General Medicine. New York: Mc Graw-Hill; 1993. p. 797-804.

The effectiveness of treatment for most cancers, including skin cancer and the associated precancerous lesions is directly related to early detection and treatment. The malignant melanoma of skin, due to its great potential to spread to other tissues and organs, is the biggest challenge.

For precancerous epithelial lesions, the treatment of choice is surgery to remove the affected tissue, and depending on the degree of involvement of the affected area, chemotherapy (including immunotherapy) and localized radiotherapy can be also administered.

Among the cytotoxic drugs used to treat precancerous skin lesions, including actinic keratosis, is 5-Fluoruacil [IUPAC (5-fluoro-1H-pyrimidine-2,4-dione) Molecular formula ($C_4H_3FN_2O_2$), CAS (51-21-8), ATC (L01BC02) PubChem (3385), DrugBank (APRD00516)] used in formulations for topical application.

Photodynamic therapy with the use of sensitizing substances is also available in the state of the art for the treatment of precancerous and cancerous lesions.

In short, this type of therapy is based on the associated use of photosensitizing substances, that is, substances that respond by releasing toxic substances to the target cells, when exposed to polarized light, laser and pulsed light.

The phototherapeutic agent tends to concentrate on the affected tissue (Hamblin, M. R.; Newman, E. L.; J. Photochem. Photobiol. 1994, B23, 3), although the mechanisms for this selectivity are not yet elucidated in the state of the art.

It is known that, at least in part, this selectivity is a result of the association of the phototherapeutic agent with lipoproteins of the plasma, which carries the referred agent mostly to abnormal cells, because these cells have a high number of low-density lipoprotein (LDL) receptors, due to its high demand for cholesterol. (Levy, J. G.; Trends in Biotechnol. 1995, 13, 14).

This knowledge has proved useful for the development of more selective phototherapeutic procedures: the use of lipoproteins, and more recently, of specific antibodies (monoclonal antibodies) associated to the phototherapeutic agent, resulted in the high selectivity of the treatment, with preservation of a much greater number of healthy cells. For examples in the state of the art, we cite: Reddi, E.; J. Photochem. Photobiol. 1997, B37, 189 e a 62-65 e Hoebke, M. J.; J. Photochem. Photobiol. 1995, B28, 189.

The 5-aminolevulinic acid (5-ALA) can be cited as an example of photosensitizing agent in the state of the art. After impregnating the skin tissue, it has the ability to capture the irradiation of a concentrated light when it is directed to the area to be treated, and through photochemical mechanisms reactive forms of oxygen are produced that can cause tissue destruction in the irradiated area.

Photodynamic therapy has the ability to eliminate actinic keratoses, which are precancerous skin lesions, and is also recommended for the treatment of superficial, non-melanoma skin tumors (e.g. squamous cell carcinoma and basal cell carcinoma). For an introductory example to the state of the art, we cite: Bock, G.; Harnett, S.; Photosensitizing Compounds: their Chemistry, Biology and Clinical use, Wiley, Chichester, 1989.

Photodynamic therapy is also indicated for the therapeutic or palliative treatment of precancerous lesions and cancer in superficial tissues of internal organs (e.g. lung, bladder, cervix, esophagus).

The compound named Imiquimod: [IUPAC (-(2-methylpropyl)-3 5,8-triazatricyclo [7.4.0.02,6]trideca-1(9), 2(6), 4,7,10,12-hexaen-7-amine), Molecular formula: (C14H16N4), CAS (99011-02-6), ATC (D06BB10), PubChem (57469) DrugBank (APRD01030)] is a biological response modifier that has recently become available in the state of the art and used topically.

It is approved for the treatment of genital lesions caused by HPV and also for the treatment of precancerous skin lesions such as actinic keratosis and epithelial cancer such as superficial squamous cell carcinoma and non-invasive melanoma.

Although the mechanism of action is unknown, the use of the compound is associated to the stimulus to the production of cytokines associated with TH-1 immune response (inflammatory response), which in turn activate defense cells of the immune system such as macrophages and NK cells, considered essential to the body's defense against intracellular pathogens and cancer. For an example of the state of the art, we cite: Miller, R. L., et al. Imiquimod applied topically: a novel immune response modifier and a new class of drug. Int J Immunopharmacol. 1999 January; 21(1): 1-14.

The most frequent complication in the use of the imiquimod are localized skin reactions, ranging from moderate to intense. For the state of the art, we can cite: Francesco Lacarrubba, et al. Advances in the use of topical imiquimod to treat dermatologic disorders, Ther Clin Risk Manag. 2008 February; 4(1): 87-97.

The compound (imiquimod) is reported in a clinical study with 169 patients for the preventive treatment of skin carcinoma, with a significant rate of protection against tumor recurrence within 2 (two) years after therapy. For the state of the art, we can cite: Quirk C, Gebauer K, Owens M, Stampone P., Two-year interim results from a 5-year study evaluating clinical recurrence of superficial basal cell carcinoma after treatment with imiquimod 5% cream daily for 6 weeks. Australas J Dermatol. 2006 November; 47(4): 258-65.

Caustic products are also used and surgical procedures are performed by mechanical, electrical (cauterization) and freezing (cryosurgery) to eliminate and/or remove precancerous lesions in women (cervical dysplasias), which are associated to the human papilloma virus (HPV).

In the state of the art, the anti-HPV preventive vaccine (HPV-16/18 AS04-adjuvant vaccine), used as adjuvant immunotherapy in a study involving young women, has been reported as having a prophylactic or preventive effect in the treatment of cervical cancer, since it has significantly reduced the number of cervical dysplasias (called precancerous conditions) in the patients that participated in the clinical trial.

For an example in the state of the art: J Paavonen, P Naud, J Salmerón, C M Wheeler, S-N Chow, D Apter, H Kitchener, X Castellsague, J C Teixeira, S R Skinner, J Hedrick, U Jaisamrarn, G Limson, S Garland, A Szarewski, B Romanowski, F Y Aoki, T F Schwarz, W A J Poppe, F X Bosch, D Jenkins, K Hardt, T Zahaf, D Descamps, F Struyf, M Lehtinen, G Dubin—Effectiveness of human papillomavirus (HPV)-16/18 AS04-adjuvanted vaccine against cervical infection and precancer caused by oncogenic HPV types (PATRICIA): final analysis of a double-blind, randomised study in young women", The Lancet, Volume 374, Issue 9686, Pages 301-314, 25 Jul. 2009., DOI: 10.1016/S0140-6736(09) 61248-4.

Therapeutic vaccination against HPV using quadrivalent vaccine (anti-HPV vaccine-types 6, 11, 16, 18) also reported as an efficient prophylactic or preventive therapy in the treatment of precancerous lesions in the genital area in women. For an example of the state of the art, please see: Effectiveness of a Quadrivalent Prophylactic Human Papillomavirus (Types 6, 11, 16, and 18) L1 Virus-Like-Particle Vaccine Against High-Grade Vulval and Vaginal Lesions: A Combined Analysis of Three Randomized Clinical Trials,"—The Lancet (2007; 369(9574): 1693-1702).

Monoclonal antibodies that block receptors of epidermal growth factors, such as Cetuximab may block the evolution or growth of abnormal cells, still in the premalignant stage, and, thus, they are being proposed and used also for the preventive treatment of precancerous lesions of upper gastrointestinal tract.

Also, monoclonal antibodies combined with photodynamic or photosensitive agents are being proposed for the treatment of precancerous and/or cancerous lesions, in order to increase the therapeutic action.

Gastroesophageal Reflux Disease (GERD)—Esophagus or Barret's Syndrome-Association with Cellular Damage and Precancerous Lesions.

The so-called gastroesophageal reflux disease (GERD) or reflux esophagitis is a pathological condition resulting from backflow (gastroesophageal reflux) of part of the stomach contents into the esophagus, triggering intense symptoms and other complications.

If not diagnosed and treated appropriately, GERD may evolve to changes in the esophageal epithelium called Barrett's esophagus or Barrett's syndrome.

The so-called Barrett's esophagus or syndrome is considered a GERD complication, which is characterized by abnormal changes (dysplasias) in cells of the lower esophagus, with the mucosa of this anatomical region being progressively replaced by a mucosa with histological features similar to those of the lining of the stomach and intestine (metaplasia).

Metaplasia is an alteration that occurs when adult cells, of epithelial or mesenchymal origin, are replaced by other types of cells. Metaplasia is interpreted as an attempt of the body to replace a type of cell exposed to an aggressive factor by another type of cell more apt to face that factor.

Additionally, the same hostile stimulus that generated metaplasia and cell dysplasias, when persistent or chronic, can induce neoplastic transformation. As examples we cite the carcinoma of squamous cells caused by metaplastic cells in the respiratory tract and Barrett's esophagus and adenocarcinoma.

Macroscopically the so-called Barrett's esophagus appears as a change in which the normal pink tissue of the esophagus is replaced by a tissue of a more reddish color, resembling the lining of the stomach.

Microscopically, the cell changes in people affected by Barrett's esophagus or syndrome, who develop cancer in the course of the syndrome, typically evolve through a series of steps, beginning with low-grade dysplasia which may become a high-grade dysplasia, and finally cancer.

For all these factors, the cellular change (dysplasia) associated to Barrett's esophagus or syndrome is considered a potentially precancerous condition, often progressing to malignant tumor of the esophagus, adenocarcinoma being the most frequent type.

Therefore, patients with Barrett's syndrome should undergo periodic endoscopies and biopsies of the upper digestive tract, at least once a year, to check the degree of change of the cells within the tissues surrounding the internal organs.

In case of appearance of more abnormal cell changes (high-grade dysplasias), the period between endoscopies with biopsy can be significantly reduced, and they can be performed every two or three months.

When cell dysplasia evolves to cancer, surgical removal of the esophagus is the standard procedure, usually followed by radiotherapy and/or chemotherapy.

Treatment of Precancerous Lesions in the Epithelium of the Digestive Tract—Gastroesophageal Reflux Disease—Barrett's Esophagus or Syndrome—State of the Art Drugs: For the pharmacological treatment of GERD the following classes of drugs are used: Antacids, H2 blockers, proton pump inhibitors, prokinetics and mucosal protectors.

Antacids are intended to neutralize the stomach acid and are produced mainly with aluminum hydroxide and magnesium hydroxide. They have no therapeutic action on GERD, and are used as palliative measures to minimize the discomfort of the disease.

The compounds known as H2 blockers act by making the stomach produce less acid. They are effective in patients with mild symptoms or those in maintenance treatment, after the crisis. They include famotidine, cimetidine and ranitidine.

The compounds known as proton pump inhibitors are the first choice of treatment of reflux and shall also be useful in patients who did not respond to H2 blockers. The usual examples include: omeprazol, esomeprazol, lansoprazol, pantoprazol, rabeprazol.

Prokinetics are compounds that can help reduce reflux, but are not usually used as the only treatment. They help the stomach empty the acid faster, reducing the time period during which reflux can occur. The most common prokinetics are metoclopramide, domperidone and cisapride.

Mucosal protectors are compounds aimed to protect the natural lining of the esophagus. One example is the sucralfate [IUPAC: (Hexadeca-µ-hydroxytetracosahydroxy[µ8-[1,3,4, 6-tetra-O-sulfo-β-Dfructofuranosyl-α-D-glucopyranoside tetrakis (hydrogen sulfate)8-)]]hexadecaaluminum), molecular formula: ($C_{12}H_{54}A_{116}O_{75}S_8$) CAS (54182-58-0), ATC A02BX02, PubChem (6398525) DrugBank (APRD01238)] which has the ability to bind to hydrochloric acid in the stomach, plugging the secretion and hence possess cytoprotective properties.

Surgical Treatments:

Corrective measures: Usually the treatment of Barrett's esophagus or syndrome involve measures aimed at controlling the so-called gastroesophageal reflux disease (GERD) or reflux esophagitis.

Among these corrective measures regarding GERD, we can cite the surgery to correct the hiatal hernia, when part of the stomach protrudes into the chest, which occurs in most patients with severe reflux esophagitis.

The surgery (esophagectomy) with total removal of the esophagus, is the standard procedure for the treatment of cancer, but can also be used for treating Barrett's syndrome, when there is high-grade dysplasia. This is a complex surgical procedure, with high risk of postoperative complications, though it can eliminate the dysplasia or the cancerous tissue, with low relapse rate.

Cryotherapy is a surgical procedure that uses carbon dioxide or liquid nitrogen to freeze the cells in the affected region in the esophagus. The frozen tissue dies and is progressively replaced by healthy tissue. Depending on the extent of the affected area, multiple sessions or treatments must be performed. The procedure is used to treat both Barrett's syndrome and localized, early stage esophagus cancer.

The so-called endoscopic mucosal resection is another surgical procedure used to treat both Barrett's syndrome and esophagus cancer in early stages. The procedure is based on injection of saline below the affected area, forming a well-defined elevation or capsule, which allows the surgeon to cut or sever the abnormal tissue, leaving the esophagus intact.

Combined Therapies

Photodynamic therapy is a surgical procedure combined with the use of drugs, beginning with the intravenous injection of a compound sensitive to certain wavelengths of light. A few days after injection of this compound, a laser that is attached to an endoscope is placed inside the esophagus, generating high energy beams of light in the affected region. The interaction between light and photoactive substance produces waves of energy that destroy the cells in the region subjected to laser. Photodynamic therapy is used to treat both Barrett's syndrome and esophagus cancer in their early stages. It is also used for treatment of esophageal cancer recurrence after surgery, alone or combined with endoscopic resection.

Photodynamic therapy produces larger ablation volumes than any ablative method. However, it presents a high risk of complications in the postoperative period.

The latest combination treatment for intestinal cellular dysplasia (Barrett's esophagus or treatment) available in the state of the art is the so-called endoscopic radiofrequency ablation.

In this type of surgical procedure combined with high frequency waves two types of devices are used, one being a spherical or balloon diffuser coupled to a catheter and a power generator. The device is inserted into the esophagus, placed in contact with the surface of the affected area and emits radio waves of high frequency that destroy the damaged tissue, which will be replaced by healthy tissue.

Another type of device based on the same principle allows the application of focal therapy, being more used for the removal of tissue (waves of energy/heat) in small size lesions or to treat relapses.

A clinical study involving 127 patients with Barrett's esophagus or syndrome and high and low-grade dysplasia was subjected to this type of surgery, that is, endoscopic radiofrequency ablation, using the aforementioned devices. The results of this study showed a high rate of eradication dysplasias and metaplasias in the postoperative period. They also show a significant decrease in the rate of progression to cancer in these patients. For an example in the state of the art, we cite: Nicholas J. Shaheen et all, Radiofrequency Ablation in Barrett's Esophagus with Dysplasia—The New England Journal of Medicine—Volume 360:2277-2288 May 28, 2009 Number 22.

Problems and Obstacles in the Treatment of Precancerous Lesions—Need for Improvements Given the importance of early treatment to prevent the development of precancerous lesions to cancer and the continuing need for improvement in the treatments of these conditions of great clinical importance, some practical examples of the invention, that is, of the use of the biological response modifier as a new therapeutic option, and, thus, not known in the state of the art for the treatment of the aforementioned conditions, will be provided.

The biological response modifier (proteic aggregate of ammonium and magnesium phospholinoleate-palmitoleate anhydride) is reported in the state of the art as possessing curative properties in cancer, ie, after the disease has manifested itself (PI—0305373-3 U.S. Ser. No. 10/978,683, EPA 0426250.3.2405).

However, there is no report in the state of the art involving its use as a preventive therapy for cancer, i.e. to treat the so-called precancerous lesions, either alone or in the form of associations or combinations with other non drug treatments.

With the latest scientific advances, new and remarkable knowledge was obtained regarding the biological properties of the biological response modifier (proteic aggregate of ammonium and magnesium phospholinoleate-palmitoleate anhydride), which was found to be suitable for the purposes of the present invention, including preventive treatment of cancer, being specially selected as an adjuvant therapy for the preventive, curative or palliative treatment of precancerous lesions, as shall be detailed in the present report.

A strong reason for the use of the biological response modifier (proteic aggregate of ammonium and magnesium phospholinoleate-palmitoleate anhydride) in the preventive treatment of cancer concerns the fact that the ability of the aforementioned compound of binding to toll-like receptors and, thus, acting as a stimulator (agonist) was established in experiments performed specifically for the purposes of the present invention, as shall be demonstrate in the present report. And this binding property to the referred receptors is shown in Table T-1 and Table T-2 has not been described in the current state of the art for this compound.

For the purposes of the present invention, this ability to bind to toll-like receptors of the biological response modifier (proteic aggregate of ammonium and magnesium phospholinoleate-palmitoleate anhydride) has played a key role in its use for this purpose, once according to the latest scientific advances, these receptors (toll-like receptors) are also involved in the maintenance of homeostasis in cell repair and regeneration processes. For a general view of the most recent state of the art regarding these receptors and their influence on the aforementioned processes, please see: Seth Rakoff—Nahoum and Ruslan Medzhitov—Toll-like receptors and cancer-Cancer Nature Reviews—Vol. 9—January—2009.

The link between chronic inflammation and cancer has long been recognized in the state of the art, that is, the important role played by reactive inflammatory processes in the modification of a normal cell to cancer cell (carcinogenesis), and given the therapeutic effects obtained in clinical trials for events (cachexia) that can also be related to reactive inflammation, as one of its various causes, and new experimental data demonstrating the ability of the biological response modifier (proteic aggregate of ammonium and magnesium phospholinoleate-palmitoleate anhydride) of binding to toll-like cell receptors, and which indicate a role played by this compound in cell repair and regeneration processes, this compound has been deliberately selected as part of the present invention for the preventive treatment of cancer when the damage or carcinogenic factor is related to cell transformation associated to carcinogenic factors and/or agents, as will be extensively explained in the present report. This new practical application incorporated or provided by the present invention can by no means be considered a simple or obvious consequence of the state of the art.

Therefore, in order to demonstrate the applicability or usefulness of the compound, a biological response modifier (proteic aggregate of ammonium and magnesium phospholinoleate-palmitoleate anhydride) for the purposes of the present invention, the action of the referred compound was evaluated, in clinical practice, through an appropriate experimental model, on inflammatory and carcinogenic processes and also on the process of transformation of cell dysplasia into cancer, aiming to obtain its practical use as a preventive therapy for cancer, according to one of the purposes of the present invention.

Subsequently, after a brief explanation on models for experimental studies on carcinogenesis and on the treatment of precancerous lesions in the state of the art, some practical examples of the use of the present invention will be provided. These examples are produced for the sole purpose of illustrating the state of the art and do not intend to limit the scope of the present invention.

Experimental Models for Carcinogenesis

Since most precancerous lesions related to the aggressive action of external agents such as solar radiation, chemical substances such as alcohol and tobacco are located in the external (skin) or internal (gastrointestinal tract, bladder) epithelial tissues, it is important to choose the appropriate experimental model in order to reproduce as accurately as possible the situations that occur in practice.

In order to evaluate, in clinical practice, the effectiveness of the biological response modifier for the treatment of precancerous lesions caused or induced by aggressive agents the experimental model involving chemically induced carcinogenesis in hamsters (*Mesocriatus auratus*), using the carcinogenic compound called 7,12-dimethilbenz (a) anthracene or else dimethyl benzanthracene, or the abbreviation DMBA in the state of the art.

The compound called DMBA, named 7,12-dimethylbenz (a) anthracene (dimethylbenzanthracene-DMBA) according to IUPAC standards. Molecular formula:

($C_{20}H_{16}$), CAS (57-97-6 Y), PubChem (6001) is a chemical compound belonging to the class of polycyclic aromatic hydrocarbons, described in the state of the art as a complete carcinogen, which initiates and promotes neoplasias.

Because of these features, DMBA is unique amongst inducing drugs, being widely used studies of chemically-induced carcinogenesis, without the need for additional adjuvant substances to trigger the neoplastic process. For an example of the state of the art: O'Neill P. Environmental chemistry. 3rd ed. New York: Blackie Academic & Professional; 1998.

Animal models that use hamsters treated with DMBA solution are widely used in the study of cancer derived from precancerous lesions (dysplasias) induced by this carcinogenic product in epithelial tissues of the upper aerodigestive tract (mouth, tongue, esophagus) and. Thus, the referred experimental model is adequate to demonstrate the practical usefulness, that is, the therapeutic ability of the biological response modifier (proteic aggregate of ammonium and magnesium phospholinoleate-palmitoleate anhydride) for this situation of interest for the purposes of the present invention.

Therefore, in order to establish the practical usefulness of the compound to be used for the preventive treatment of cancer, the experiment reports the action of the biological response modifier (proteic aggregate of ammonium and magnesium phospholinoleate-palmitoleate anhydride) in an experimental model of induced carcinogenesis in Syrian golden hamsters using the hydrocarbon compound 7,12-Dimethylbenzanthracene (DMBA) to induce neoplasia in the tissues of the epithelial lining of the mouth of the animals.

The results obtained can be extrapolated to all those situations that involve the formation and evolution of precancerous lesions in the outer and inner epithelium, induced or promoted by external aggressive agents (carcinogens), such as chemical agents, solar radiation and finally precancerous cell change associated to viruses, as will be extensively explained in the present report.

The practical example that follows is for illustrative purposes only and does not intend to limit the scope of the present invention.

Example of the Practical Use of the Biological Response Modifier (Proteic Aggregate of Ammonium and Magnesium Phospholinoleate-Palmitoleate Anhydride) in an Experimental Model of Carcinogenesis by DMBA Materials and Methods:

Animals: Syrian golden hamsters (*Mesocriatus auratus*) males and females aged 60 days with mean body weight between 95 and 100 grams Inducer of carcinogenesis: 7,12-dimethilbenz (a) anthracene (DMBA, Sigma Aldrich).

Biological response modifier: Proteic aggregate of ammonium and magnesium phospholinoleate-palmitoleate anhydride Dosage: 10 mg/kg/day per animal Route of administration: subcutaneous Experimental Procedure:

60 Syrian golden hamsters (*Mesocriatus auratus*), 30 males and 30 females aged 60 days and with a mean body weight between 90 and 100 grams were used.

The animals were distributed into six groups: three treatment groups and three control groups, with 10 animals in each group, corresponding to three experimental periods at 7, 13 and 20 week intervals.

The animals were individually identified with ear tags.

The animals were observed and weighed daily and the events, including changes in behavior and possible deaths, were recorded.

DMBA solution (0.5% in mineral oil) was applied topically to the cheek pouch of each animal using a brush, three times a week.

The biological response modifier (proteic aggregate of ammonium and magnesium phospholinoleate-palmitoleate anhydride) was applied every day in the groups treated with 10 mg/kg/subcutaneous DMBA diluted in saline. The animals in the control group were subcutaneously injected the same volume of saline alone.

At the end of each period established for each experimental group, that is, in the 7th, 14th and 20th weeks, the animals in the treatment groups and control groups (10 animals in each group) were sacrificed.

The left cheek pouch of each animal was removed, fixed in 10% buffered formaldehyde for macroscopic evaluation and preparation of slides for histological examination.

For histological examinations, the cheek pouches were included in paraffin blocks, and then 5-µm thick sections were cut using a microtome and stained with hematoxilin-eosin (H.E.) for assessment of cellular changes and comparison between the control group and the treatment groups.

Results: Although clinical manifestations were not observed on macroscopic examination for the control and treatment groups, in the 7th week the histological examination of the tissues of the cheek pouches of all the animals in the control group (DMBA) sacrificed in this period showed significant changes, with various degrees of atypia (dysplasias).

None of the animals in the treatment group sacrificed in the 7th week showed significant atypias on the histological examinations of tissue extracts of the cheek pouches of the animals.

On the 8th week, all animals in the control (DMBA), that is, 100%, showed clinical changes on macroscopic examination consisting of leukoplakia in the same region painted with the carcinogen, which was very swollen (congested). Only two animals, that is, 20% of the treatment group showed discrete macroscopic lesions compared to the control animals.

On the 14th week, the histological examination of tissue extracts of the cheek pouches of the animals in the control group (DMBA) showed microscopic changes consistent with squamous cell carcinoma, that is, 100% of the animals. Of the animals in the treatment group that were sacrificed on the 14th week, although two of them had discrete macroscopic lesions, only one had microscopic lesions in the tissue consistent with squamous cell carcinoma, that is, 10% of the animals.

On the 20th week, besides macroscopic changes consisting in leukoplakia, generalized congestion of the area painted with DMBA and signs of bleeding in isolated spots, histological examination of the tissues of cheek pouches of all animals in the control group (DBMA), that is, 100% of the animals also showed microscopic lesions consistent with squamous cell carcinoma.

Two animals in the control group (DMBA) died in the 18th and 19th weeks, that is, 20% of the animals. None of the animals in the group treated with the biological response modifier died during the experiment.

The cheek pouches of these animals that died during the 18th and 19th weeks were preserved for histopatological examination and also showed microscopic changes consistent with squamous cell carcinoma.

Of the animals in the treatment group sacrificed in the 20th week, two had macroscopic changes consisting of leukoplakia and congestion in the area painted with DMBA, though more discrete than in the control group. However, on microscopic examination, the tissue of the cheek pouch of these animals, that is, 20% of the total revealed signs and changes consistent with squamous cell carcinoma.

Discussion of the results: The use of the biological response modifier (proteic aggregate of ammonium and magnesium phospholinoleate-palmitoleate anhydride) had a remarkable protective effect against DMBA-induced carcinogenesis in the animals of this experiment compared to the animals in the control group treated with 0.9% saline.

That is, whereas 100% of the animals in the control group (DMBA) treated with NaCl (0.9%) alone had microscopic signs in the oral epithelium consistent with squamous cell carcinoma, only 20% of the animals treated with the biological response modifier (proteic aggregate of ammonium and magnesium phospholinoleate-palmitoleate anhydride) had cellular changes consistent with carcinoma in the tissue of the cheek pouch, in the group treated and followed up for the longest period of time, that is, (20) twenty weeks.

This remarkable and surprisingly effect involving the biological response modifier (proteic aggregate of ammonium and magnesium phospholinoleate-palmitoleate anhydride), that is, prevention of the occurrence and/or evolution of the dysplasia to cancer in living beings, in this case, experimental animals, was not described in the state of the art until now.

Although the mechanisms of action of this protective effect are largely hypothetical, it should be stressed that this protection begins in the early state of cell change, since the animals treated with the biological response modifier (proteic aggregate of ammonium and magnesium phospholinoleate-palmitoleate anhydride) examined in the 7th week did not show significant macroscopic and microscopic changes compared to the non-treated control animals.

One hypothesis on the mechanism of action can be related to the stimulus to toll-like cell receptors by the biological response modifier (proteic aggregate of ammonium and magnesium phospholinoleate-palmitoleate anhydride), with reports in the state of the art on the action of ligands for TLR-2 and TLR-4 and mechanisms of protection and regeneration of cellular tissue damaged by various factors. The data shown in Table T1 and Table T2 show the ability of the biological response modifier (proteic aggregate of ammonium and magnesium phospholinoleate-palmitoleate anhydride) of binding to TLR-2 and TLR-4 receptors.

Another hypothetical possibility is the existence of a dual mechanism of action, that is, that the compound (proteic aggregate of ammonium and magnesium phospholinoleate-palmitoleate anhydride), besides providing a protective effect that is possible due to the ability of this compound to act as a ligand (agonist) for toll-like cell receptors, which induce cell repair mechanisms, also induces or stimulates the action of the immune system on epithelial cells affected in their early precancerous stage, destroying them and, thus, ensuring a preponderance of healthy cells in the epithelial region.

Regardless of the mechanisms of action, the remarkable practical result of the experiment encourage its immediate use as a preventive therapy for situations of high risk for the development of neoplasias, that is, in the treatment of precancerous lesions, e.g. those occurring in skin carcinomas, malignant melanoma and other skin tumors, or else it can be used in the preventive treatment of uterine cancer that starts with changes in uterine epithelial cells caused by the action of various types of the human papillomavirus (HPV).

Or else, and finally for tumors of the digestive tract and/or upper airway tract (mouth, throat) derived from precancerous lesions of the lining epithelium, as shall be extensively demonstrated in the present report, with practical examples of the use of the invention. Other examples and references of the current state of the art are provided below to help understanding the remarkable and innovative properties of this invention.

Precancerous Lesions and Cervical Dysplasia and Evolution to Cancer—Associated Factors—Treatment—State of the Art The so-called cervical dysplasia is considered a premalignant or precancerous change or modification of the epithelial cells of the cervix. For illustrative purposes, we cite: Kumar, Vinay; Abbas, Abul K.; Fausto, Nelson; & Mitchell, Richard N. (2007). Robbins Basic Pathology ((8th ed.) ed.). Saunders Elsevier. Pp. 718-721.

In some cases, cervical dysplasia remains stable or is eliminated by the immune system However, if untreated; it may become a chronic condition and progress to cervical cancer.

Cervical dysplasia is routinely diagnosed in clinical practice using the Papanicolaou test, also named Pap smear or Pap test, for the early detection of lesions.

The Pap smear test is a routine test where cells from the cervix (uterus) are collected for the cytological examination of the smear.

Besides its classical use for the assessment of tissue in the cervical region, the Pap test is also used for the evaluation of the effectiveness of the treatments.

The results of Pap smears are grouped in 5 (five) categories: Class I indicates absence of abnormal cells, class II usually indicates inflammation or infection and Class III indicates the presence of changed cells (dysplasia).

Class III can be subdivided into three subclasses or other types of dysplasia: mild, moderate or severe.

Cauterization is generally indicated in the mild and moderate types. In severe dysplasia, the removal of a segment of the cervix called conization or other surgical measures may be necessary.

Class IV represents a highly suspicious result of malignancy, and Class V is considered representative of a manifested neoplasia.

Determinants for Cervical Dysplasia—Chronical Infection by HPV

In the state of the art, it is well established that the determinants (causes) of most chronic cervical dysplasias is the infection by the human papilloma vírus—HPV, which is sexually transmissible. There are around 100 types of HPV identified, of which one dozen are implied in the process that generates cervical dysplasia and its progression to cervical cancer.

The HPV-16 and HPV-18 types are said to be responsible for 60% of the cases of cervix cancer in the world. We cite: Munoz N, Castellsague X, de Gonzalez A B, Gissmann L. Chapter 1: HPV in the etiology of human cancer. Vaccine. 2006; 24 Suppl 3:S1-S10.)

The types HPV 6, HPV-11, HPV-16, HPV-18, HPV-33 and HPV-45 are considered to be of high risk for carcinogenesis. For an example of the early state of the art, we cite: Schiffman, M. H., 1992. Recent progress in defining the epidemiology of human papillomavirus infection and cervical neoplasia. Journal of the National Cancer Institute. 84(6): 394-398.

All these types (HPV 6, HPV-11, HPV-16, HPV-18, HPV-33, HPV-45) cited and recognized as being of high risk for carcinogenesis are associated to the development of cervical dysplasias, that is, precancerous lesions because they may evolve into cancer. The presence and characterization of these viral types are assessed after the confirmation of cervical dysplasia, through various laboratory techniques, such as in situ hybridization, hybrid capture, PCR).

There is no scientific consensus so far whether the cellular changes called dysplasias (cervical dysplasia) can be directly associated to viral activity (direct cytopathic effect) or indirectly, that is, due to cellular changes induced by the pathogen-host interaction (indirect cytopathic effect) or finally, by the combination of both situations or causes.

Nevertheless, regardless of the causal factors of cervical dysplasia it is evident for any expert with knowledge of the state of the art, without the need for further explanations, that the concomitant treatment of the primary carcinogenic cause, that is, of the chronic viral infection performed before, during or after the treatment or removal of dysplasia, which is a lesion usually associated to HPV, is an important condition for the success of the therapy, because it reduces the chances of recurrence of infection that can lead again to dysplasia.

Thus, an hypothetical ideal treatment for the precancerous cellular condition or change, that is, cervical dysplasia, which is associated to chronic infection by HPV, should fight or eliminate the changed cells (dysplasia) and at the same time control the causative agent, that is, the HPV. As will be shown in the present report, the invention has both abilities.

Cervical Dysplasia—Preventive Therapies—Treatment Options

Since chronic infection by HPV is known to be associated to the induction of dysplasias and evolution to cancer, various treatments were developed and are available in the state of the art to attempt to control and/or eliminate the viruses and associated lesions and/or at least provide a palliative treatment of dysplasias and cancer For examples of the state of the art: Jung W W, et al. Strategies against human papillomavirus infection and cervical cancer. J Microbiol. 2004 December; 42(4):255-66 e ainda; Scheinfeld N, Lehman D S. An evidence-based review of medical and surgical treatments of genital warts. Dermatol Online J. 2006 Mar. 30; 12(3):5.

Infection by HPV can be described in three main forms of presentation: clinical, subclinical and latent. The clinical form, with the presence of macroscopic lesions (genital warts) in the anogenital region; the subclinical form, characterized by the presence of diffuse epithelial hyperplasia and dysplasia, seen through the colposcope and after application of contrast medium (acetic acid) and the latent form, that is, without histological changes, though with the presence of the viral DNA detected by techniques such as hybridization, hybrid capture or PCR (polymerase chain reaction).

The traditional treatments aimed mostly to the elimination of lesions associated to HPV or its clinical manifestations, such as genital warts, involve local therapies, with the use of caustic agents such as podophyllin and its derivatives and also trichloroacetic acid.

The most widely used techniques with varying degrees of success in the state of the art are: local excision, cryotherapy, CO2 laser vaporization and electrocauterization. However, the surgical treatments for the clinical and subclinical forms of HPV are not very efficient and have a high degree of recurrence. They involve long periods of time and are often painful and/or disfiguring.

Main Problems Involving Surgical Treatments for the Elimination of Dysplasias

Surgical procedures to remove HPV infected tissues can be painful and impractical for the treatment of extensive lesions. In the state of the art there is great controversy as to whether the frequent post-treatment recurrences are due to reactivation of subclinical infection or derived from normal epithelium left untreated. For examples of the state of the art, we cite: Krebs, H.-B., 1989. Management strategies. Clinical Obstetrics and Gynecology. 32(1): 200-213.

The most frequent complications include pain, local secretion, ulceration, infection and delayed healing. Permanent scarring may also occur. The results are conflicting in terms of recurrence and persistence of subclinical lesions. For examples of the state of the art, we cite: Ling, M. R., 1992b. Therapy of genital human papillomavirus infections. Part II: Methods of treatment. International Journal of Dermatology. 31(11): 769-776.

Recent Advances in the State of the Art—Immunotherapy

In the state of the art, the use of immunotherapy for the treatment of HPV infection and the damage caused by this virus to the cells (dysplasias) started with BCG vaccination, also used in the treatment of tuberculosis, and with locally applied interferons to increase immunity, with mixed results. For examples of the state of the art, we cite: Kraus, S. J. & Stone, K. M., 1990, Management of genital infection caused by human papillomavirus—Reviews of Infectious Diseases. 12 (supl. 6): S620-S632.

With the development of new compounds, immunotherapy becomes an attractive therapeutic option in the state of the art for the treatment of HPV infections. Some new compounds available in the state of the art follow:

Imiquimod: [(IUPAC: -(2-methylpropyl)-3,5,8-triazatricyclo[7.4.0.02,6]trideca-1(9), 2(6), 4,7,10,12-hexaen-7-amine, Molecular formula: C14H16N4, CAS (99011-02-6) ATC (D06BB10) PubChem (57469) DrugBank (APRD01030)] is a topical biological response modifier that has been recently made available in the state of the art.

It is approved for the treatment of genital lesions caused by HPV in women, as well as for the treatment of precancerous skin lesions in individuals of both sexes, such as actinic keratosis and epithelial cancer, e.g. superficial squamous cell carcinoma and malignant melanoma in its early stage of development.

Imiquimod is known to be able to act as a ligand (agonist) to cell membrane receptors for toll like receptors or TLR, being able to activate the so-called TLR 7 and 8 receptors also associated to viral recognition by cells that express such receptors. Agonists (stimulants) of toll-like receptors (TLRs) act as biological response modifiers because they can activate the effector mechanisms of specialized cells of the immune system, the dendritic cells, which have these specific receptors at their surface.

Although the mechanism of action of imiquimod and similar molecules on cancer is hypothetical because it is not fully elucidated, the use of this compound in neoplasia, according to several authors, also stimulates the production of cytokines associated to TH-1 immune response, which in turn activate defense cells of the immune system, such as macrophages and NK cells, essential to the body's defense against intracellular pathogens and cancer. For an example of the state of the art, we cite: Miller, R. L., et al. Imiquimod applied topically: a novel immune response modifier and a new class of drug. Int J Immunopharmacol. 1999 January; 21(1): 1-14.

Recent studies suggest also a dual mechanism of action for imiquimod and resiquimod, that is, acting like agonists (stimulants) for toll-like receptors (TLRs), and, thus, like biological response modifiers and also acting on the opioid growth development factor or OGF, which would explain their antitumor, regardless of the effect on the immune system. For an example of the state of the art, we cite: Ian S. Zagon et. Al, Imiquimod Upregulates the Opioid Growth Factor Receptor to Inhibit Cell Proliferation Independent of Immune Function, Experimental Biology and Medicine 233: 968-979 (2008).

The use of Imiquimod is reported in a clinical study with 169 patients as a preventive treatment for skin carcinoma, with a significant degree of protection against tumor recurrence within 2 (two) years after treatment. For an example in the state of the art, we cite: Quirk C, Gebauer K, Owens M, Stampone P., Two-year interim results from a 5-year study evaluating clinical recurrence of superficial basal cell carcinoma after treatment with imiquimod 5% cream daily for 6 weeks. Australas J Dermatol. 2006 November; 47(4): 258-65.

The most frequent complication in the use of imiquimod is skin responses ranging from moderate to intense. Headache, bone pain and intestinal problems associated to the use of the product are reported. For an example in the state of the art, we cite: Francesco Lacarrubba, et al. Advances in the use of topical imiquimod to treat dermatologic disorders, Ther Clin Risk Manag. 2008 February; 4(1): 87-97.

Resiquimod [IUPAC (1-[4-amino-2-(ethoxymethyl)imidazo[4,5-c]quinolin-1-yl]-2-methylpropan-2-ol), molecular formula: C17H22N4O2, CAS (144875-48-9), PubChem (59603)].

The compound named resiquimod is indicated for use as biological response modifier. Also, due to its ability to bind to toll-like receptors, it can also act as an adjuvant of therapeutic vaccines, or else, to assist in or induce an increased TH-1 response, maximizing the effect of these therapeutic vaccines. For an example of the state of the art, we cite: Mark A Tomai et. al, Resiquimod and other immune response modifiers as vaccine adjuvants, Expert Review of Vaccines, October 2007, Vol. 6, No. 5, Pages 835-847, DOI 10.1586/14760584.6.5.835.

Advances in the State of the Art—Prophylactic and Therapeutic Vaccines Against HPV The most recent advance in the state of the art concerns the development of vaccines against HPV, which act in a preventive way against the main carcinogenic types of HPV (HPV-6, HPV-11, HPV-16 and HPV-18). They are only efficient for women who have not yet reached sexual maturity or with no prior infection with HPV. There is still not a therapeutic vaccine against HPV that ensures their elimination in patients already infected or with a previous history of infection.

Preventive vaccines against the most prevalent viral types are available in the state of the art, that is, bivalent vaccine against HPV 16/18 and tetravalent against the HPV 6/11/16/18 types.

Its impact on public health is still limited, mainly because of the lack of mass vaccination programs. When used for therapeutic purposes in patients with HPV infection the current vaccines have shown modest results, albeit it did have some effect on cervical dysplasias.

In the state of the art, the anti-HPV bivalent vaccine (HPV-16/18 AS04-adjuvant vaccine) in a study involving young women is reported to have also a prophylactic or preventive effect on cervical cancer, besides an antiviral action against HPV, since it has significantly decreased the number of precancerous lesions (cervical dysplasia) in the patients that participated in the clinical trial.

For an example of the state of the art: J Paavonen, P Naud, J Salmerón, C M Wheeler, S-N Chow, D Apter, H Kitchener, X Castellsague, J C Teixeira, S R Skinner, J Hedrick, U Jaisamrarn, G Limson, S Garland, A Szarewski, B Romanowski, F Y Aoki, T F Schwarz, W A J Poppe, F X Bosch, D Jenkins, K Hardt, T Zahaf, D Descamps, F Struyf, M Lehtinen, G Dubin—Effectiveness of human papillomavirus (HPV)-16/18 AS04-adjuvanted vaccine against cervical infection and precancer caused by oncogenic HPV types (PATRICIA): final analysis of a double-blind, randomised study in young women", The Lancet, Volume 374, Issue 9686, Pages 301-314, 25 Jul. 2009., DOI: 10.1016/S0140-6736(09)61248-4.

Therapeutic vaccination against HPV using quadrivalent vaccine (anti HPV 6/11/16/18 vaccine) is also reported as being effective as a prophylactic or preventive therapy in the treatment of precancerous lesions in the vaginal region. For an example of the state of the art: Efficacy of a Quadrivalent Prophylactic Human Papillomavirus (Types 6, 11, 16, and 18) L1 Virus-Like-Particle Vaccine Against High-Grade Vulval and Vaginal Lesions: A Combined Analysis of Three Randomized Clinical Trials,"—The Lancet (2007; 369(9574): 1693-1702).

Treatment of Precancerous Lesions and Cervical Dysplasias—State of the Art

In the state of the art, it is widely accepted that the first stage of development of cervical cancer is the condition known as dysplasia, which occurs when squamous cells in the cervical region become abnormal in size and shape and begin to multiply.

Cervical dysplasia (III degree Papanicolaou) is classified as mild, moderate or severe, depending on the degree of cellular abnormality on microscopic examination.

In mild dysplasia, abnormal cells appear only on the surface layer of cervix. This condition may progress if not timely treated, evolving to severe dysplasia.

If not treated, severe dysplasia will progress in most cases to the maximum stage or degree, which is early cervical cancer, also known as carcinoma in situ.

Chemical abrasion with the use of caustic products such as podophyllin, as well as surgical procedures performed by mechanical, electrical (cauterization) and freezing (cryosurgery) means are used to eliminate and/or remove cervical epithelial lesions usually associated to the action of the human papillomavirus (HPV).

In the state of the art, the anti-HPV vaccine (HPV-16/18 AS04-adjuvant vaccine) is reported in a study involving young women to have a prophylactic or preventive effect on cervical cancer too, having significantly reduced the number of precancerous lesions (cervical dysplasia) in the patients that participated in the clinical trial.

For an example in the state of the art: J Paavonen, P Naud, J Salmerón, C M Wheeler, S-N Chow, D Apter, H Kitchener, X Castellsague, J C Teixeira, S R Skinner, J Hedrick, U Jaisamrarn, G Limson, S Garland, A Szarewski, B Romanowski, F Y Aoki, T F Schwarz, W A J Poppe, F X Bosch, D Jenkins, K Hardt, T Zahaf, D Descamps, F Struyf, M Lehtinen, G Dubin—Efficacy of human papillomavirus (HPV)-16/18 AS04-adjuvanted vaccine against cervical infection and precancer caused by oncogenic HPV types (PATRICIA): final analysis of a double-blind, randomised study in young women", The Lancet, Volume 374, Issue 9686, Pages 301-314, 25 Jul. 2009., DOI: 10.1016/S0140-6736(09)61248-4.

Therapeutic vaccination against HPV using quadrivalent vaccine (anti-HPV vaccine 6/1/11/16/18 is also reported to have some prophylactic or preventive effectiveness on the treatment of precancerous lesions in the vaginal region. For an example in the state of the art: Efficacy of a Quadrivalent Prophylactic Human Papillomavirus (Types 6, 11, 16, and 18) L1 Virus-Like-Particle Vaccine Against High-Grade Vulval and Vaginal Lesions: A Combined Analysis of Three Randomized Clinical Trials,"—The Lancet (2007; 369(9574): 1693-1702)

Regardless of the techniques used to remove tissue damaged or changed, it is evident for any expert with knowledge of the state of the art that the success of preventive, curative or palliative treatments of precancerous lesions, that is, cervical dysplasias of any nature, with progression to cancer avoided, is also influenced by the efficient treatment of the main causative agent, that is, HPV, particularly the carcinogenic types (HPV 6/11/16/18).

Treatment of Precancerous Lesions and Cervical Dysplasias—Current Problems—State of the Art In the state of the art, the recurrence rates for all the current excision or surgical treatments used to eliminate/treat precancerous cervical lesions or alterations (dysplasias) are very high, precisely because of the great difficulty in eliminating the main causative agent, that is, the human papilloma virus or HPV.

Preventive vaccines (bivalent anti-HPV 16/18 and tetravalent HPV-6/11/16/18) are only effective in patient without HPV and have little effect on patients with chronic dysplasia, post-infection by HPV, as mentioned in the present report.

However, the importance of the immunotherapeutic approach in providing viable solutions for the problem should be considered, once there are solutions in the state of the art for the treatment of HPV based on immunotherapy, such as anti-HPV preventive vaccines and also new biological response modifiers such as the imiquimod and resiquimod.

Given these facts and the recognized immunomodulatory properties of the biological response modifier (proteic aggregate of ammonium and magnesium phospholinoleate-palmitoleate anhydride) and its remarkable effect on epithelial dysplasias induced in hamsters by carcinogenic agents (DMBA) also described in the present report, the compound was specially selected also for use in the treatment of cervical dysplasia associated to the human papillomavirus, in combination with the current state of the art treatments.

Another factor that has led to the deliberate selection of the biological response modifier (proteic aggregate of ammonium and magnesium phospholinoleate-palmitoleate anhydride) as a component of the invention is its action as a product capable of stimulating toll-like receptors, including TRL-2 receptors (Table T-1 and Table T-2) that are involved in the triggering the immune response against bacteria and viruses. For an example of the recent state of the art, we cite: Gregory M Barton et al., Toll-like receptor 2 on inflammatory monocytes induces type I interferon in response to viral but not bacterial ligands. Nature Immunology, published online 4 Oct. 2009; doi:10.1038/ni.1792.

Other studies have related the TLR-4, also stimulated by the biological response modifier specifically selected for the present invention (proteic aggregate of ammonium and magnesium phospholinoleate-palmitoleate anhydride), (Table T 1 and Table T2) as also able to recognize viral structural proteins. For examples of the state of the art, we cite: Kurt-Jones, E. A. et al. Pattern recognition receptors TLR4 and CD14 mediate response to respiratory syncytial virus. Nature Immunol. 1, 398-401 (2000) and also: Georgel, P. et al. Vesicular stomatitis virus glycoprotein G activates a specific antiviral Toll-like receptor 4-dependent pathway. Virology 362, 304-313 (2007).

Finally, given the need to eliminate or prevent cellular dysplasia, the ability of the biological response modifier (proteic aggregate of ammonium and magnesium phospholinoleate-palmitoleate anhydride) of binding to toll-like receptors is of great relevance in view of the scientific advances that related toll-like receptors to important cell repair and regeneration processes, since inflammatory response is undeniably associated to cervical dysplasia in HPV infection.

For all these reasons, the biological response modifier (proteic aggregate of ammonium and magnesium phospholinoleate-palmitoleate anhydride) was specially selected as a component to be associated or combined to several state of the art preventive, curative and palliative treatments of precancerous cervical lesions (dysplasias) associated to HPV.

In order to demonstrate in practice the effectiveness of the present invention in the treatment of HPV-related cervical dysplasia, an example of its use in a clinical trial involving patients with chronic and recurrent HPV infection and cervical dysplasias associated to the infection ranging from mild to moderate, who did not respond satisfactorily to standard treatments in the state of the art, that is, electrocauterization surgery. The practical example that follows is for illustrative purposes only and does not intend to limit the scope of the present invention.

Practical Example of the Use of Present Invention—Use of the Biological Response Modifier in Recurrent HPV Infection and Cervical Dysplasia.

Clinical study: Post surgical application of the biological response modifier (proteic aggregate of ammonium and magnesium phospholinoleate-palmitoleate anhydride) in 20 women with medium to severe dysplasia and HPV seropositivity.

A clinical study involving 20 women with medium to severe dysplasia, confirmed by laboratory tests (III degree Papanicolaou) and HPV seropositivity (PCR method) was conducted.

All patients had previous history of routine surgical procedures for removal of the damaged tissue (electrocauterization) before the clinical trial, with recurrence of dysplasia and infection in all the cases.

The patients underwent routine examinations before the clinical trial for evaluation of dysplasia (Papanicolaou test) and cervical smears were taken for human papillomavirus (HPV) testing and typing.

Of the 20 patients that participated in the clinical trial, 10 were classified as suffering from moderate cervical dysplasia associated to HPV 11, 5 with moderate cervical dysplasia associated to HPV 18 and 5 with severe cervical dysplasia associated to types HPV-16 and HPV-18.

The results of the tests of patients on admission to the trial are shown in Table P-1

TABLE P-1

Classification of the degree of cervical dysplasia and viral typing performed on admission to the clinical trial (basal)

| Number of patients | Mild dysplasia () | Moderate dysplasia | Severe dysplasia () | Type of HPV associated (*) |
|---|---|---|---|---|
| 10 | — | 10 | — | HPV 11 |
| 5 | — | 5 | — | HPV 18 |
| 5 | — | — | 5 | HPV 16/18 |

(*) Method for detection and viral typing: PCR - Kit Amplicor (HPV) - Roche
(**) Method for detection and classification of cervical dysplasia: Papanicolaou Periodicity: Collection of cervical smear for the test and classification of dysplasia and HPV were performed in the pretreatment period (basal) and 6 months after the end of the clinical trial.

Clinical and laboratory characterization: Patients who were previously treated with electrocauterization and showing signs of cervical dysplasia classified into medium to severe upon admission to the clinical trial.

Viral typing: All patients (100%) had at least one viral type considered high risk for developing malignancy on admission, and five patients (25%) showed association of more than one viral type (HPV 16e HPV 18).

Clinical trial design: All patients underwent again surgery, that is, electrocauterization for removal of the changed tissue (dysplasia).

They were also given a 5 mg/m2 dose of the biological response modifier intramuscularly, in physiological saline (NaCl 0.9%) in three cycles of application, as follows:

Dosage: 3 (three) cycles of 10 doses of 5 mg/m2 for all patients, injected intramuscularly, with the first dose starting 1 day after electrocauterization.

Follow-up: The patients were followed monthly by clinical examinations and colposcopy.

Final assessment: The patients were assessed again 6 (six) months or 180 days after the end of the surgical procedure associated to the applications of the biological response modifier for dysplasia and presence of HPV.

Results: The results are shown in Table P-2 and then discussed.

TABLE P-2

Classification of the degree of cervical dysplasia and viral typing after the clinical trial (T: 180 days after the end)

| Number of patients | Mild dysplasia () | Moderate dysplasia () | Severe dysplasia (**) | HPV type associated (*) |
|---|---|---|---|---|
| 20 | — | — | — | — |
| 1 | — | — | — | HPV 18 |
| 1 | — | — | — | HPV 16/18 |

(*) Method for detection and viral typing: PCR - Kit Amplicor (HPV) - Roche
(**) Method for detection and classification of cervical dysplasia: Papanicolaou Discussion of the results: The use of the present invention, that is, the biological response modifier associated to a surgical procedure (electrocauterization) showed remarkable results in the patients that participated in the clinical trial, acting on the cervical dysplasia and on the causative agent (HPV).

Although the sample is limited in number, it should be noted that all patients have previously undergone the same surgical procedures for removal of changed tissue (cervical dysplasia) and relapsed, that is, 100% of recurrence was observed.

The recurrence rate with the use of the invention, that is, the biological response modifier associated to surgery (electrocauterization) was 0% (zero percent), that is, none of the twenty patients showed any sign of dysplasia during assessment 180 days after the beginning of the clinical trial, although 2 (two) of them, that is, 10% of the patients still had HPV at that time (180 days after the beginning of the trial) compared to the recurrence rate of 100% for cervical dysplasia and viral presence at the beginning of the experiment reported in the same patients who received only surgical treatment.

It should be noted that these patients did not show cervical dysplasia anymore during the assessment period (180 days after the end of the clinical trial), which clearly demonstrates the direct effect of the invention on cellular change (cervical dysplasia), that is, on precancerous cells, regardless of the presence of the virus, since the laboratory tests of these patients showed the presence of residual HPV in 2 (two) patients.

This effect of the invention on the precancerous lesion (cervical dysplasia) regardless of the presence of the virus has been demonstrated, for all patients had moderate to severe dysplasia on admission to the clinical trial and after being treated with the present invention dysplasia was completely eliminated, though HPV was detected in a few patients (10%) (Table P-2).

Absolute Novelty of the Invention for the Treatment of HPV-Related Cervical Dysplasia.

The use of the biological response modifier (proteic aggregate of ammonium and magnesium phospholinoleate-palmitoleate anhydride) as a component of drug associations or combinations against facultative or strict intracellular pathogens or parasites is described in PI 0801803-0 and WO/2009/097670, which includes general antiviral action, once these pathogens are classified as strict intracellular parasites.

This previous invention (PI 0801803-0, WO/2009/097670), that is, the practical use of the biological response modifier (proteic aggregate of ammonium and magnesium phospholinoleate-palmitoleate anhydride) for the treatment of infections caused by intracellular parasites is substantially different from the present invention, including specific treatment of associated precancerous lesions or HPV-related cervical dysplasias.

The previous invention (PI 0801803-0, WO/2009/097670) concerns the use of the biological response modifier (proteic aggregate of ammonium and magnesium phospholinoleate-palmitoleate anhydride) for the curative treatment of infectious diseases, including those of viral origin.

As for the present invention, it is intended for a completely different purpose, that is, the practical use of the biological response modifier (proteic aggregate of ammonium and magnesium phospholinoleate-palmitoleate anhydride) associated to other non-drug and/or drug treatments also for the preventive treatment of cancer, and also the treatment of precancerous lesions in various organs and tissues, including cervical dysplasias, which are precancerous lesions associated and/or induced by the direct and/or indirect cytopathic effect of several HPV viruses.

As will be extensively exposed in the present report, although it is highly desirable that a compound or treatment also helps eliminate viruses, particularly those capable of inducing cellular changes that may evolve to cancer, and the present invention has also this additional ability for the specific case of oncogenic viruses such as the HPV, this is not sufficient to ensure its success in the treatment of precancerous lesions, that is, in controlling or eliminating such precancerous lesions.

In order to be recognized as useful to treat precancerous lesions, in the specific case of dysplasias associated with the human papillomavirus (HPV), a treatment should be able to additionally and/or concomitantly eliminate or control the causative agent, eliminate or control the existing or new precancerous cellular lesions, including revert or control the associated inflammatory process and finally assist in cellular regeneration, which involves therapeutic abilities for the intended treatment that go far beyond the mere control or elimination of the causative agent.

In the present invention, and specifically in the treatment of precancerous lesions (cervical dysplasia) associated to the presence of chronic HPV infection, the effectiveness is obtained with the use of the invention in its entirety, that is, the association or combination of a biological response modifier (proteic aggregate of ammonium and magnesium phospholinoleate-palmitoleate anhydride) with at least one other non-drug and/or drug treatment that will produce new and remarkable therapeutic effects related to epithelial regeneration and/or protection, also in precancerous lesions, which have not been previously described in the state of the art.

In the example provided in this report, the practical use of the invention (Table P-1 and Table P-2), that is, its use in the treatment of cervical dysplasia associated to chronic and recurrent HPV infection, comprised the association of the biological response modifier (proteic aggregate of ammonium and magnesium phospholinoleate-palmitoleate anhydride) to a non-drug treatment, that is, a surgical procedure called electrocauterization, in order to ensure the successful elimination or control of cervical dysplasia.

Hypothetical Mechanisms of Action for the Biological Response Modifier in Precancerous Lesions It is possible that the effect of the biological response modifier (proteic aggregate of ammonium and magnesium phospholinoleate-palmitoleate anhydride), one of the components of the invention, is associated e.g. to the activation of dendritic cells via toll-like cell receptors (TLRs) in the plasma membrane of these antigen presenting cells, considered in the state of the art essential components of the innate immune system. The TLRs recognize molecular components of invading microorganisms and also of compounds able to bind to the referred receptors.

Afterwards, the dendritic cells that express TLR would activate the cells that control the immune response (CD-4 lymphocytes or T-4 lymphocytes) that would trigger the whole immune cascade, particularly the TH-1 type immune response, involving cytokine release, including IFN-gamma and IL-2, as well as other macrophage-activating substances, and would finally block or eliminate agents that induce or promote malignant cell transformations, such as HPV, in the case of cervical dysplasia, for example.

Although until very recently in the state of the art it was believed that the TLR2 and TLR4 were associated only to the recognition of molecular patterns expressed by bacteria and other nonviral intracellular parasites, very recent advances in the state of the art demonstrate that the RLR2 are also associated to the recognition of several types of viruses, being present in receptors of specialized cells called monocytes. Stimulated by ligands or molecules that activate TLR2 (agonists), these monocytes would secrete cytokines that produce a TH-1 immune response.

For a more recent example of the state of the art, we cite: Gregory M Barton et al., Toll-like receptor 2 on inflammatory monocytes induces type I interferon in response to viral but not bacterial ligands. Nature Immunology, published online 4 Oct. 2009; doi:10.1038/ni.1792.

According to other studies, the TLR-4 receptor is also able to recognize viral structural proteins. For examples of the state of the art, we cite: Kurt-Jones, E. A. et al. Pattern recognition receptors TLR4 and CD14 mediate response to respiratory syncytial virus. Nature Immunol. 1,398-401 (2000) and (Georgel, P. et al. Vesicular stomatitis virus glycoprotein G activates a specific antiviral Toll-like receptor 4-dependent pathway. Virology 362,304-313 (2007).

Hypothetically, the antiviral action of the invention against the HPV could start through the TLR2 and TLR4. However, the antitumor action of the biological response modifier (proteic aggregate of ammonium and magnesium phospholinoleate-palmitoleate anhydride) could be also linked to other immunotherapeutic mechanisms not directly related to TLR cell receptors.

The remarkable therapeutic properties of the biological response modifier (proteic aggregate of ammonium and magnesium phospholinoleate-palmitoleate anhydride), a component of this invention, in the treatment of precancerous conditions involving the change of epithelial cells by chemical inducers (carcinogens) and also on cervical dysplasia, a condition associated to a viral inducer (HPV), demonstrated in the present report, indicate that the action of the referred biological response modifier is possibly associated to other therapeutic mechanisms that include fight against cancer cells in the beginning of the process, cell repair and regeneration, or else the occurrence or combination of these or other mechanisms.

An interesting possible application of antitumor action in the treatment of precancerous lesions, demonstrated in the present report by practical examples of elimination of chemically-induced precancerous lesions (DMBA) by the invention and/or one of its components, the biological response modifier (proteic aggregate of ammonium and magnesium phospholinoleate-palmitoleate anhydride) is described in the state of the art involving the discovery of the mechanism of action of the taxanes (taxol and derivatives), which are molecules with powerful antitumor action widely used in cancer therapy in humans.

Taxanes (taxol) were found to act against cancer cells using different mechanisms, which can also concomitantly mimic the action of TLR-4 ligands, of the LPS type or similar, inducing immune responses that are typical of these ligands, such as induction of interferon-gamma (IFN-gamma) and nitric oxide (NO) release by macrophages.

In these experiments, all immune responses induced by taxanes (taxol) occurred in macrophages of mice with positive response to LPS (an usual TLR-4 ligand) and blocked in LPS-unresponsive macrophages of the animals, indicating the presence of common and/or shared biochemical signaling pathways for both the TLR-4 ligands (LPS) and taxanes (taxol and derivatives).

Reinforcing this finding, additional experiments showed that the LPS (TLR-4 ligand), in turn, is capable of binding to beta-tubulin and also to proteins associated to microtubules, which are sites or cellular targets for the action of taxanes (taxol and derivatives) in cancer cells, mainly those that form solid tumors.

For examples of the state of the art, we cite: Manthey, C. L. Brandes, M. E., Perera, P. Y., and Vogel, S. Taxol increases steady-state levels of lipopolysaccharide-inducible genes and protein-tyrosine phosphorylation in murine macrophages. J. ImmunoL, 149: 2459-465, 1992; Ding, A. H., Porteu, F., Sanchez, E., and Nathan, C. F. Shared actions of endotoxin and taxol on TNF receptors and TNF release. Science (Washington D.C.), 248:370-372, 1990; and also Ding, A., Sanchez, E., Tancinco, M., and Nathan, C. Interactions of bacterial lipopolysaccharide with microtubule proteins. J. Immunol., 148: 2853-2858, 1992.

These experiments allow us to suggest a hypothetical dual mechanism of action for the biological response modifier (proteic aggregate of ammonium and magnesium phospholinoleate-palmitoleate anhydride), one of the components of the present invention, that is, of a common pathway that would make this compound able to act as a ligand for toll-like receptors and simultaneously act on essential metabolic processes of tumor cells.

Such hypothetical dual mechanism of action would make it possible to understand, based on the current state of the art of immunology, the remarkable therapeutic effects of this invention both for the treatment of HPV-related precancerous lesions as well as precancerous lesions induced and promoted in experimental animals by chemical carcinogens such as the dimethylbenzanthracene (DMBA), contained in the present report.

That is, the compound would have a dual mechanism of action: action against viruses, including HPV, through immune reactions initiated by and/or mediated by TLR-2 and TRL-4 type cell receptors, for which the compound act as a ligand (Table T-1 and Table T-2), which is suggested by experiments in humans (Table P-1 and Table P-2) and also an action on cervical dysplasia based on anticancer mechanisms, similarly to what occurs with taxanes (taxol and derivatives).

This mechanism makes it possible to formulate theoretical hypotheses to explain the therapeutic action of the compound in precancerous processes demonstrated in practical experiments in the present report, that is, blocking the development of fully developed precancerous lesions or else fighting cancer cells in malignant transformation in early stages, or finally, through mechanisms of cell repair and regeneration. All these hypotheses are possible in the light of the results of the experiments in hamsters treated with DMBA and also based on the reduction and elimination of HPV-related cervical dysplasia in patients (Table P-1 and Table P-2), even in cases where evidence of latent infection by HPV (Table-P1 and Table P-2) persisted.

Immunological mechanisms of cell repair and regeneration associated with chronic inflammation involving toll-like cell receptors are reported in the current state of the art and allow to associate the presence and action of toll-like cell receptors, particularly TLR-4, in cell repair and regeneration processes, and, thus, provide further justification for the use of ligand compounds (agonists) in the prevention of tumor processes, since they could also stimulate mechanisms associated to cell repair and/or control of inflammatory responses.

Experiments and scientific advances in the state of the art on the role of these cell receptors, and other studies mentioned several times in the present report (Seth Rakoff—Nahoum and Ruslan Medzhitov—Toll-like receptors and cancer-Cancer Nature Reviews—Vol. 9—January—2009.) combined to new experimental data in the present report have made it possible to hypothesize some possible mechanisms associated with and complementary to the action of the biological response modifier for the preventive treatment of cancer, once the key component of the invention, that is, the biological response modifier (proteic aggregate of ammonium and magnesium phospholinoleate-palmitoleate anhydride), is also demonstrably a TLR-2 and TLR-4 agonist, that is, a ligand/stimulant for these receptors (Table T-1 and Table T-2), and has also recognized antitumor activity.

The compound could act in cell repair and regeneration, that is, in mechanisms related to chronic inflammation both in tissues damaged by viruses, e.g. in the case of treatment of cervical dysplasia (cytopathogenic effect associated to HPV) and for internal or external epithelial precancerous lesions caused by solar radiations, chemical compounds, among other carcinogenic agents. Finally, the compound would also have another antitumor action based on mechanisms other than toll-like cell receptors, similar to the action of taxanes (taxol and derivatives).

But regardless of the hypothetical mechanisms of action of the biological response modifier and the invention that incorporates the referred compound, the action of this compound in the preventive, curative or palliative treatment of chronic systemic diseases such as cancer, as well as in precancerous lesions, can be witnessed in clinical practice, as demonstrated in experiments in the present report, and thus, this invention is fully applicable in combination with drug and non-drug treatments, and finally as a component for the manufacture of new drugs (drug associations or combinations) in situations of great interest to the state of the art of medicine described in the present report. This new practical application incorporated or provided by the present invention can by no means be considered a simple or obvious consequence of the state of the art.

Final Conclusions

In view of the practical reasons and examples cited in this report, the present invention was found to provide a new and effective preventive, curative or palliative treatment for chronic systemic diseases such as cancer.

In view of the practical reasons and examples cited in this report, the present invention was found to provide a new and effective treatment for chronic systemic diseases, which additionally allows the preventive, curative or palliative treatment of other clinical problems such as cancer, in particular, primary and secondary cachexia.

In view of the practical reasons and examples cited in this report, the present invention was found to provide a new and effective treatment for chronic systemic diseases, such as cancer, which additionally allows the preventive, curative or palliative treatment of severe side effects associated to other treatments, such as immunosuppression and neutropenia.

Any animal species can benefit from the present invention. Although the main purpose or intended field of application of the present invention is the treatment of human beings, the invention and its practical use cannot be limited to this species.

Modes of Use of the Invention

To facilitate the understanding of this report and the reproduction and use of the present invention by any person skilled in the art, it is important to stress that this invention can be used in practice in various useful and different ways, including Mode-1 and Mode-2, as follows.

(MODE 1) Use of the invention, that is, the biological response modifier (proteic aggregate of ammonium and magnesium phospholinoleate-palmitoleate anhydride) in association or combination with regimens or protocols consisting in the combination of this specific immunomodulator with other drugs and/or non-drug treatments, and all these being empirically selected by medical professionals at the beginning and/or during the course of the therapy, among those available in the state of the art and that are deemed more appropriate to be used with the biological response modifier (proteic aggregate of ammonium and magnesium phospholinoleate-palmitoleate anhydride), depending on patient and disease state.

MODE 2) Use of the biological response modifier (proteic aggregate of ammonium and magnesium phospholinoleate-palmitoleate anhydride) as a fixed component or part in the manufacture of new drugs, when combined or associated with other drugs of the most different types and categories, and also to other non-drug treatments.

Some Compounds Used in the State of the Art for Cancer Treatment and/or as Adjuvant Therapy that can be Used for the Purpose of the Present Invention The list below contains some classes of compounds used in the state of the art, cited as exemplification and by no means an exhaustive list of some classes and types of pharmacologically active substances and their most usual representatives that can be used for the purposes of the present invention, always combined or associated to the specific biological response modifier (proteic aggregate of ammonium and magnesium phospholinoleate-palmitoleate anhydride).

Main classes and types of pharmacologically active substances used in cancer treatment and and comorbidities in the current state of the art:

Alkylating agents (Altretamine, mitobronitol), Nitrogen mustards (mechlorethamine, cyclophosphamide, ifosfamide, melphalan, chlorambucil) Ethyleneimines and methylmelamines (Thiotepa and hexamethylmelamine) Alkyl sulphonates (Busulfan) Nitrosureas (carmustine (BCNU), streptozocin, hydroxyurea), Triazenes (Dacarbazine and Temozolomide) Platinum complexes (cisplatin, carboplatin, oxaliplatin, nedaplatin, Triplatin tetranitrate, satraplatin) Folic acid antagonists (aminopterin, methotrexate, pemetrexed) Purine analogues (azathioprine, mercaptopurine, thioguanine, fludarabine, pentostatin, cladribine) Pyrimidine analogues (fluorouracil, gemcitabine, floxuridin, cytarabine) Vinca alkaloids (vinblastine, vincristine, vindesine, vinorelbine, vinflunine), Terpenoids (paclitaxel, docetaxel, tesetaxel, larotaxel, ortataxel) Epothilones: (Ixabepilone) Podophyllotoxin derivatives (etoposide, teniposide) Anthracyclines (daunorubicin, doxorubicin, epirubicin, idarubicin, mitoxantrone, pixantrone, valrubicin, amrubicin, aclarubicin, pirarubicin, zorubicin) Streptomycins: (actinomycin D, bleomycin, mitomycin, plicamycin) Type I topoisomerase inhibitors (camptothecin, irinotecan, topotecan, rubitecan, belotecan) Type II topoisomerase inhibitors (amsacrine, etoposide, etoposide phosphate, teniposide) Angiogenesis inhibitors (bevasuzimab) Tyrosine Kinase blockers (erlotinib, imatinib, sunitinib, sorafenib) Hormones (tamoxifen, fulvestrant, anastrozole, letrozole, exemestane, megestrol, goserelin, leuprolide, diethylstilbestrol) Enzymes (L-Asparaginase) monoclonal antibodies (alemtuzumab, bevacizumab, cetuximab, ocrelizumab, ofatumumab, panitumumab, rituximab, trastuzumab) Monoclonal antibodies conjugated with radioactive particles (ibritumomab tiuxetan, tositumomab), Angiogenesis inhibitors (bevacizumab) Stimulation factors of the myeloid lineage (filgrastim, pegfilgrastim, lenograstim, molgramostim, sargramostim) Cytokines (interleukin-2 (IL-2), interleukin 12(IL-12), interferon alpha, interferon alpha-2a, peginterferon alfa-2a, interferon alpha-2b, peginterferon alpha-2b, interferon alpha-n1, interferon alfacon-1, interferon beta, interferon beta-1a, interferon beta-1b, tumor necrosis factor (TNF), immunotherapeutic drugs (BCG vaccine and derivatives, levamisole, isoprinosine) Biological response modifiers (imiquimod and resiquimod), therapeutic vaccines for cancer (autoimmune vaccines, dendritic cell vaccines).

Forms of Association and/or Combination for the Various Treatments—Administration of Compounds and/or Pharmacologically Active Formulations The active substances, that is, the biological response modifier (proteic aggregate of ammonium and magnesium phospholinoleate-palmitoleate anhydride), and the other pharmacologically active substances, for the purposes of the present invention, can be supplied for use alone or as separate parts for admixing, whenever possible, as well as in solid form solutions, in microencapsulated pharmaceuticals, in liposomes or in separate systems for administration, and finally in injectable and oral forms.

The preparation of the simple form of administration of one of the substances of the present invention, e.g. the biological response modifier (proteic aggregate of ammonium and magnesium phospholinoleate-palmitoleate anhydride) can be made with any of the aqueous solutions known in the state of the art and additionally with excipients, suspensions, transporters and/or stabilizers known in the state of the art.

The other active substances that can be used for the purposes of the present invention, in association and/or combination with the biological response modifier (proteic aggregate of ammonium and magnesium phospholinoleate-palmitoleate anhydride) can also be applied and/or used in any way reported for each class or type, particularly those recommended by their manufacturers, or else in other ways known or reported in the state of the art.

More than one pharmacologically active substance can be used for the purposes of this invention, as long as the biological response modifier (proteic aggregate of ammonium and magnesium phospholinoleate-palmitoleate anhydride) is a fixed component of the association or combination. To ensure the fully effectiveness of the present invention, at least one other pharmacologically substance can be used in association or combination with the biological response modifier proteic aggregate of ammonium and magnesium phospholinoleate-palmitoleate anhydride), and, thus, more than one of these substances can be administered alone, sequentially or in combination.

More than one non-drug treatment can be used for the purposes of the present invention, as long as the biological response modifier (proteic aggregate of ammonium and magnesium phospholinoleate-palmitoleate anhydride) is a fixed component of the association or combination. To ensure the full effectiveness of the invention, at least one non-drug treatment can be used in association or combination with the biological response modifier (proteic aggregate of ammonium and magnesium phospholinoleate-palmitoleate anhydride), and more than one of these non-drug treatments can be used alone, sequentially or in combination.

More than one drug and non-drug treatment can be used for the purposes of the present invention, as long as the biological response modifier (proteic aggregate of ammonium and magnesium phospholinoleate-palmitoleate anhydride) is a fixed component of the therapeutic association or combination. To ensure the full effectiveness of the invention, at least one non-drug treatment and one drug treatment can be used in association or combination with the biological response modifier (proteic aggregate of ammonium and magnesium phospholinoleate-palmitoleate anhydride) biological response modifier (proteic aggregate of ammonium and magnesium phospholinoleate-palmitoleate anhydride), and, thus, more than one of these non-drug and drug treatments can be used alone, sequentially or in combination.

The biological response modifier (proteic aggregate of ammonium and magnesium phospholinoleate-palmitoleate anhydride) is obtained through biological action exerted by the mycelium of the *Aspergillus oryzae* (*A. oryzae*) fungus, in appropriate culture medium, as described in the state of the art in PI—0305373-3, U.S. Ser. No. 10/978,683 and EPA 0426250.3.2405.

The other active substances that can be used for the purposes of the present invention, in association and/or combination with the biological response modifier (proteic aggregate of ammonium and magnesium phospholinoleate-palmitoleate anhydride) can be obtained from any production sources and methods known for every class or type described in the state of the art. The other non-drug treatments that can be used for the purposes of the present invention, in association and/or combination with the biological response modifier (proteic aggregate of ammonium and magnesium phospholinoleate-palmitoleate anhydride) can be selected from various types and forms known in the state of the art, as long as they are related to the preventive, curative or palliative treatment of cancer and its complications or comorbities. Other substances or compounds with pharmacological action against cancer and its clinical complications not cited in the present report as known in the state of the art, or to be discovered and made available for usage according to the purposes of the present invention, can be used, as long as the biological response modifier (proteic aggregate of ammonium and magnesium phospholinoleate-palmitoleate anhydride) is a fixed component for the purposes of the present invention.

Other non-drug treatments against cancer and its complications not cited in the present report as known in the state of the art, or to be discovered and made available for usage according to the purposes of the present invention, can be used, as long as the biological response modifier (proteic aggregate of ammonium and magnesium phospholinoleate-palmitoleate anhydride) is a fixed component for the purposes of the present invention.

Biological Response Modifier Specifically Selected as Part of the Invention

The biological response modifier (proteic aggregate of ammonium and magnesium phospholinoleate-palmitoleate anhydride) that shall be used as a fixed component in any combination of compounds and/or treatments for the purposes of the present invention, is contained and reported in the state of the art in PI—0305373-3, U.S. Ser. No. 10/978,683 and EPA 0426250.3.2405 and WO/2009/097670, being chemically characterized as a proteic aggregate of ammonium and magnesium phospholinoleate-palmitoleate anhydride, with molecular weight 320.000 Dalton (320 KDa) that in chemical analysis using the methodology available in the state of the art has shown the presence of 11.6±4.0% of total lipids, 22.7±5.0% of palmitoleic acid, 42.9±2.0% of linoleic acid and 32.0±3.0% of oxidated linoleic acid, 20.1±0.9% of magnesium ions, 10.0±3.3% of ammonium ions, 45.2±2.7% of phosphate and 0.49±0.01% of proteins; the aminoacid distribution in the protein is: Asp 7.19%; Thr 3.56%; Ser 7.56%; Glu 8.53%; Pro 0.5%; Gly 9.69%; Ala 7.46%; Val 1.0%; Met 4.38%, Isoleu 2.54%, Leu 3.03%, Tyr 0.5%, Phe 1.0%, His 2.83%; Lys 3.56%; Trp 1.3% and Arg 35.2%.

The production method of the biological response modifier (proteic aggregate of ammonium and magnesium phospholinoleate-palmitoleate anhydride) used for the purposes of the present invention is equally contained and reported in the state of the art in PI—0305373-3 U.S. Ser. No. 10/978,683 and EPA 0426250.3.2405, and basically consists of the use of the *Aspergillus oryzae* fungus (*A. oryzae*) in culture medium and in suitable conditions for the production of the cited biological response modifier, specifically selected to be used for the purposes of the present invention.

Any animal species can benefit from the present invention. Although the main purpose or intended field of application of the present invention is the treatment of human beings, the invention and its practical use cannot be limited to this species. Without further elaboration, it is believed that one skilled in the art can, using the report, utilize the present invention to its fullest extent.

Some Practical Examples on the Use of the Invention

In order to facilitate the viewing of some practical possibilities of the invention, some possible examples of its practical use are reported In order to facilitate understanding, some previous relevant references and comments from this report shall be mentioned again. These examples are merely illustrative and cannot be used to limit the practical applications or the scope of the present invention.

Examples of Use

A) Application of the invention for the preventive, curative or palliative treatment of cancer by acting in internal epithelial precancerous lesions, that is, located in the gastrointestinal and cervical regions and also in precancerous lesions in the external epithelium, that is, in the epidermis or skin. There is a claim on this application or usefulness based on the general properties of the invention, and notably of one of its components, the biological response modifier (proteic aggregate of ammonium and magnesium phospholinoleate-palmitoleate anhydride) described in the present report, and also based on practical experiments with animal models (hamsters) that were given chemical carcinogenic compounds (DMBA), practical experiments in cell cultures (Table T-1 and Table T-2), practical experiments in humans with cervical dysplasia caused by HPV (Table P-1 and Table P-2).

Therefore, the invention is indicated for use in the treatment of dysplasias or precancerous epithelial internal and external lesions known in the state of the art to be associated, induced or promoted by aggressive or carcinogenic external agents such as solar radiation, chemical compounds, viruses and others.

Among these situations or pathological conditions for which the present invention offers usefulness, innovation and practical benefits, as well as possible modes of use, some applications for the invention based on scientific data, experiments and explanations contained in this report are cited for illustrative purposes, by no means constituting an exhaustive list of the practical applications of the invention:

(A-1) Preventive, curative or palliative treatment of epithelial lesions (dysplasias, metaplasias), that is, precancerous skin lesions of any degree such as actinic keratosis and others, associated to the action of aggressive external and/or carcinogenic agents, such as solar radiations, with the use of non-drug therapies.

(A-2) Preventive, curative or palliative treatment of epithelial lesions (dysplasias, metaplasias), that is, precancerous skin lesions of any degree, such as actinic keratosis and others, associated to the action of aggressive external and/or carcinogenic agents, such as solar radiation, with the use of drug therapies.

(A-3) Preventive, curative or palliative treatment of epithelial lesions (dysplasias, metaplasias), that is, precancerous skin lesions of any degree, such as actinic keratosis and others, associated to the action of aggressive external and/or carcinogenic agents, such as solar radiation, using non-drug and drug therapies.

(A-4) Use of the biological response modifier (proteic aggregate of ammonium and magnesium phospholinoleate-palmitoleate anhydride) as a component in the manufacture of new drugs in combinations or associations with drugs known in the current state of the art, for use in the preventive, curative or palliative treatment of epithelial lesions (dysplasias, metaplasias), that is, precancerous skin lesions of any degree, such as actinic keratosis and others, associated to the action of aggressive external and/or carcinogenic agents such as solar radiation.

(A-5) Preventive, curative or palliative treatment of cervical lesions (dysplasias), that is, precancerous lesions of any degree associated to the action of several types of the human papilloma virus (HPV), with the use of non-drug therapies.

(A-6) Preventive, curative or palliative treatment of cervical lesions (dysplasias), that is, precancerous lesions of any degree associated to the action of several types of the human papilloma virus (HPV), with the use of drug therapies.

(A-7) Preventive, curative or palliative treatment of cervical lesions (dysplasias), that is, precancerous lesions of any degree associated to the action of several types of the human papilloma virus (HPV), with the use of non-drug and drug therapies.

(A-8) Use of the biological response modifier (proteic aggregate of ammonium and magnesium phospholinoleate-palmitoleate anhydride) as a component in the manufacture of new drugs in combinations or associations with drugs known in the current state of the art, for use in the preventive, curative or palliative treatment of cervical lesions (dysplasias), that is, precancerous lesions of any degree associated to the various types of the human papilloma virus (HPV), such as other biological response modifiers, e.g. imiquimod and resiquimod, anti-HPV preventive vaccines, therapeutic vaccines against dysplasia and HPV, photoactive compounds and other compounds not specified.

(A-9) Use of the biological response modifier (proteic aggregate of ammonium and magnesium phospholinoleate-palmitoleate anhydride) as a component in the manufacture of new drugs in combinations or associations with drugs known in the current state of the art, for use in the preventive, curative or palliative treatment of cervical lesions (dysplasias), that is, precancerous lesions of any degree associated to the various types of human papilloma virus (HPV).

(A-10) Preventive, curative or palliative treatment of lesions (dysplasias, metaplasias), that is, precancerous epithelial internal (gastroesophageal region) lesions of any degree (dysplasias or metaplasias) associated to the action of aggressive or carcinogenic agents such as chemical compounds and others, e.g. lesions associated to gastroesophageal reflux disease or GERD, epithelial lesions called Barrett's esophagus or Barrett's syndrome, with the use of non-drug therapies.

(A-11) Preventive, curative or palliative treatment of lesions (dysplasias, metaplasias), that is, precancerous epithelial internal (gastroesophageal region) lesions of any degree (dysplasias or metaplasias), or else, potentially precancerous lesions of any degree associated to aggressive or carcinogenic agents such as chemical compounds, e.g.

lesions associated to gastroesophageal reflux disease or GERD, epithelial lesions called Barrett's esophagus or Barrett's syndrome, with the use of drug therapies.

(A-12) Preventive, curative or palliative treatment of lesions (dysplasias, metaplasias), that is, precancerous epithelial internal (gastroesophageal), or else, potentially precancerous lesions of any degree associated to the action of aggressive or carcinogenic agents such as chemical compounds and others e.g. lesions associated to gastroesophageal reflux disease or GERD, epithelial lesions called Barrett's esophagus or Barrett's syndrome, with the use of combined therapies, that is, using surgery and drugs, such as the photodynamic or photoactive therapy using laser, endoscopic radiofrequency ablation using balloon catheter and other compounds not specified.

(A-13) Use of the biological response modifier (proteic aggregate of ammonium and magnesium phospholinoleate-palmitoleate anhydride) as a component in the manufacture of new drugs in combinations or associations with drugs known in the current state of the art, for use in the preventive, curative or palliative treatment of lesions (dysplasias, metaplasias), or else, precancerous epithelial internal (gastroesophageal) lesions of any degree associated to the action of aggressive or carcinogenic agents like chemical compounds and others, e.g. lesions associated to gastroesophageal reflux disease or GERD, epithelial lesions called Barrett's esophagus or Barrett's syndrome.

B) Application of the invention for the preventive, curative or palliative treatment of cancer manifest in any part of the body or at any stage of development, consisting of solid or non-solid, metastatic or non-metastatic tumors.

There is a claim on such application or usefulness based on the general properties of the invention described in this report, notably of one of its components, the biological response modifier (proteic aggregate of ammonium and magnesium phospholinoleate-palmitoleate anhydride) and of components of the invention contained in the present report, and also based on practical experiments with animals, e.g. the experiment using hamsters that were given DMBA, other animal experiments (Table A, Table B, Table C, Table L), practical experiments in cell cultures (Table T-1 and Table T-2), practical experiments in humans (Table H, Table M, Table P-1 and Table P-2).

(B-1) Preventive, curative or palliative treatment of cancer manifest in any part of the body or at any stage of development, consisting of solid or non-solid, metastatic or non-metastatic tumors, with the use of non-drug therapies.

(B-2) Preventive, curative or palliative treatment of cancer manifest in any part of the body or at any stage of development consisting of solid or non-solid, metastatic or non-metastatic tumors, with the use of drug therapies.

As described in this report, and based on practical examples of the use of the invention, that is, the association or combination of the biological response modifier (proteic aggregate of ammonium and magnesium phospholinoleate-palmitoleate anhydride) with other compounds or drugs, can be enabled or used through the most varied combinations involving all classes or categories of drugs or compounds existing in the current state of the art, that is, the combination or association of the biological response modifier (proteic aggregate of ammonium and magnesium phospholinoleate-palmitoleate anhydride) with other compounds has a more effective action that is distinct from and wider than the biological properties of the isolated compounds.

The main classes, categories or families of compounds and/or drugs in the current state of the art in the treatment of cancer are: alkylating agents, antimetabolites, mitotic inhibitors, antitumor antibiotics, topoisomerase inhibitors, tyrosine kinase blockers, hormones, monoclonal antibodies, angiogenesis inhibitors, monoclonal antibodies conjugated with cytotoxics, stimulation factors of the myeloid lineage, therapeutic vaccines, cytokines, immunotherapy drugs, biological response modifiers, enzymes and other compounds not specified.

The invention, that is, the association or combination of a biological response modifier (proteic aggregate of ammonium and magnesium phospholinoleate-palmitoleate anhydride) can be used in association or combination with other classes or categories and compounds not yet available for practical use or not cited in the present report, since the principle of the invention remains unchanged, once the invention is essentially based on the association or combination of a biological response modifier (proteic aggregate of ammonium and magnesium phospholinoleate-palmitoleate anhydride) with other compounds in the amounts, forms, etc. necessary to produce the desired effects described in the present report, and the referred compound is the only fixed component of the invention, since the nature of the disease (cancer) will not be modified, and the immune system will continue to play a vital role in the treatment of cancer in any stage.

Thus, the invention may incorporate at any time new compounds to be used in the association or combination that characterizes the invention, as long as the key component, that is, the biological response modifier (proteic aggregate of ammonium and magnesium phospholinoleate-palmitoleate anhydride) is a fixed component for use in association or combination with the referred compounds, or else to be used as a component in the manufacture of new drugs associated to at least one of these compounds.

(B-3) Preventive, curative or palliative treatment of cancer manifested in any part of the body and at any stage of development, consisting of solid or non-solid, metastatic or non-metastatic tumors, with the use of non-drug and drug therapies.

The invention, that is, the association or combination of the biological response modifier (proteic aggregate of ammonium and magnesium phospholinoleate-palmitoleate anhydride) with other treatments, according to the purposes of the present invention, can be used in clinical practice with prior, concomitant or subsequent treatment with other current state of the art non-drug treatments and also with the other current state of the art drug treatments, for the preventive, curative or palliative treatment of cancer.

(B-4) Use of the biological response modifier (proteic aggregate of ammonium and magnesium phospholinoleate-palmitoleate anhydride) as a component in the manufacture of new drugs in association or combination with these other current state of the art drugs, for use in the preventive, curative or palliative treatment of cancer, or else, cancer manifest in any part of the body or at any stage of development consisting of solid or non-solid, metastatic or non-metastatic tumors, with the use of drug therapies.

(C) Application of the invention for the preventive, curative or palliative treatment of cancer already manifest in any part of the body and manifestations or pathological states associated to the primary disease, such as anorexia-cachexia syndrome (cachexia) and/or aggravated by other treatments (secondary cachexia). There is a claim on such application or usefulness based on the properties and the remarkable effects of the invention, notably of one of its components, the biological response modifier (proteic aggregate of ammonium and magnesium phospholinoleate-palmitoleate anhydride) described in the present report and also based on practical experiments with hamsters given DMBA, practical experiments with cell cultures (Table T-1 and Table T-2), practical experiments with humans with cancer (Table M) receiving radiotherapy and/or chemotherapy (Table H).

As described in the present report, cachexia associated with chronic systemic diseases such as cancer is a serious illness of multifactorial origin, which is impacted by tumor-host interactions and may be aggravated by the non-drug (e.g. radiotherapy) and drug treatments used.

Besides the properties of the biological response modifier, such as its molecular composition, especially the aminoacid (arginine) and the polyunsaturated fatty acid (linoleic acid) routinely used in food supplementation therapy in catabolic states (including cachexia), the compound has other properties that are useful in the state of the art, that is, immunomodulatory abilities and the ability to bind to toll-like cell receptors, which interfere in the maintenance of homeostasis, as well as the protection against aggressive agents provided by the internal and external epithelium are the reasons for the deliberate selection of the biological response modifier (proteic aggregate of ammonium and magnesium phospholinoleate-palmitoleate anhydride) as an essential component of the present invention, so that it can also used in the specific treatment of primary and secondary cachexia.

These therapeutic indications were confirmed in clinical practice through the use of the invention in the form of a combination of drug and non-drug treatments, including in humans (Table M) with remarkable and outstanding practical results both regarding the average body weight (Table M) and the control of opportunist infections (Table H) resulting in significant improvement in the clinical status of patients, as shown in the present report.

Therefore, due to the remarkable and innovative practical effect of the use of the biological response modifier (proteic aggregate of ammonium and magnesium phospholinoleate-palmitoleate anhydride), the referred compound can be effectively used in the treatment of primary cachexia, as well as of secondary cachexia, which is associated with cytotoxic treatments e.g. radiotherapy, and/or drugs, such as anti-neoplastic compounds.

Thus, the use of the present invention, that is, the biological response modifier (proteic aggregate of ammonium and magnesium phospholinoleate-palmitoleate anhydride) associated or combined to non-drug or drug treatments in the current state of the art for the treatment of the primary disease, that is, cancer (Table M) shall provide also a remarkable preventive, curative or palliative effect on the morbid condition known as cachexia, both the condition associated to the disease itself (primary cachexia) and the one that results from the use of cytotoxic drugs and treatments (secondary cachexia).

It can be seen that some practical applications of the invention, that is, the biological response modifier (proteic aggregate of ammonium and magnesium phospholinoleate-palmitoleate anhydride) associated or combined to non-drug or drug therapies allows the correction or minimization of malnutrition and secondary cachexia, and, thus, it will be possible to use higher doses or more aggressive therapeutic regimens or protocols against the primary disease (cancer), either with higher doses or shorter intervals, that would otherwise not be possible due to the occurrence of secondary cachexia associated to the toxicity of these other drugs and/or treatments.

Additionally, the invention, that is, the biological response modifier (proteic aggregate of ammonium and magnesium phospholinoleate-palmitoleate anhydride) can be used not only in association or combination with other non-drug and drug therapies for the treatment of chronic systemic diseases such as cancer, but also associated to the various treatments described in the state of the art against malnutrition and cachexia e.g. nutritional products and dietary supplements and other drugs available in the state of the art described in the present report.

The biological response modifier (proteic aggregate of ammonium and magnesium phospholinoleate-palmitoleate anhydride) can be used as a component in the manufacture of new drugs, that is, associations of drugs specifically aimed at cancer treatment, and also in the manufacture drug associations when associated or combine to various compounds and drugs specifically used in the treatment of malnutrition and cachexia.

(C-1) Application of the invention for the preventive, curative or palliative treatment of cancer already manifest and specifically of manifestations or pathological states associated to the primary disease, such as the anorexia-cachexia syndrome (cachexia) and/or aggravated by other non-drug treatments (secondary cachexia).

(C-2) Application of the invention for the preventive, curative or palliative treatment of cancer already manifest and specifically of manifestations or pathological states associated to the primary disease, such as the anorexia-cachexia syndrome (cachexia) and/or aggravated by other drug treatments (secondary cachexia).

The invention, that is, the association or combination of the biological response modifier (proteic aggregate of ammonium and magnesium phospholinoleate-palmitoleate anhydride) with other treatments, according to the purposes of the invention, and specifically in the treatment of primary and secondary cachexia can be use in clinical practice with prior, concomitant or subsequent current state of the art drug treatments for the primary disease (cancer).

(C-4) Use of the biological response modifier (proteic aggregate of ammonium and magnesium phospholinoleate-palmitoleate anhydride) as a component in the manufacture of new cancer drugs in the form of drug associations or combinations known in the current state of the art, for the preventive, curative or palliative treatment of cancer, that is, cancer manifest in any part of the body or at any stage of development, consisting of solid or non-solid, metastatic or non-metastatic tumors, with the use of drug therapies, and specially with the incorporation of the biological response modifier (proteic aggregate of ammonium and magnesium phospholinoleate-palmitoleate anhydride) to the association or formulation, as an adjuvant therapy in the preventive, curative or palliative treatment of cachexia.

The invention, that is, the association or combination of the biological response modifier (proteic aggregate of ammonium and magnesium phospholinoleate-palmitoleate anhydride) with other treatments, according to the purposes of the invention, and specifically in the treatment of primary and secondary cachexia, can be used in clinical practice as a component in the manufacture of new drugs, in the form of drug associations with other compounds or drugs currently known in the state of the art as anticancer agents.

(C-4) Application of the invention for the preventive, curative or palliative treatment of cancer, and specifically of manifestations or pathological states associated to the primary disease (cancer), such as primary cachexia and/or aggravated by other drug treatments (secondary cachexia).

The invention, that is, the association or combination of the biological response modifier (proteic aggregate of ammonium and magnesium phospholinoleate-palmitoleate anhydride) with other treatments and compounds, according to the purposes of the invention, and specifically in the treatment of primary and secondary cachexia can be used in clinical practice with prior, concomitant or subsequent current state of the art treatments and compounds for the treatment of malnutrition and cachexia.

(C-5) Use of the biological response modifier (proteic aggregate of ammonium and magnesium phospholinoleate-palmitoleate anhydride) as a component in the manufacture of new drugs to treat malnutrition, primary and secondary cachexia, in the form of associations or combinations with other drugs known in the current state of the art in the preventive, curative or palliative treatment of primary and secondary cachexia associated to cancer and/or drugs and/or treatments.

The invention, that is, the association or combination of the biological response modifier (proteic aggregate of ammonium and magnesium phospholinoleate-palmitoleate anhydride) with other treatments, according to the purposes of the invention, and specifically in the treatment of primary and secondary cachexia, can be used in clinical practice as a component in the manufacture of new drugs, in the form of drug associations with other current state of the art compounds or drugs, for the preventive, curative or palliative treatment of malnutrition and cachexia associated to chronic systemic diseases such as cancer.

(D) Application of the invention for the preventive, curative or palliative treatment of cancer and specifically the manifestations or pathological states associated to the primary disease and to non-drug and drug treatments, such as immunosuppression and neutropenia.

There is a claim on such application or usefulness based on the general properties of the invention, and notably one of its components, the biological response modifier ((proteic aggregate of ammonium and magnesium phospholinoleate-palmitoleate anhydride) described in the present report, and also based on practical experiments in monkeys (Table D), mice (Table C, Table L) and finally practical experiments in humans with cancer treated with radiotherapy and/or chemotherapy (Table-H)

It is known in the state of the art that immunosuppression is one of the events associated to chronic systemic diseases such as cancer, and, thus, immunotherapy is widely used in the treatment of these diseases.

Additionally, it is widely known in the state if the art that most drugs used in the treatment of chronic systemic diseases such as cancer, particularly cytotoxic drugs and other treatments, either alone or in combination in the form of protocols of drugs or treatments, have adverse effects, and one of the main adverse effects associated to their use is neutropenia, which represents a major complication in the treatment of patients, as extensively described in the present report, with support of strong scientific evidence and examples in the state of the art.

These adverse consequences of drugs and/or treatments in clinical practice often lead to reduction of the dose or treatment discontinuation, and impose the use of other drugs for the prevention of infections, hospitalization of patients for the treatment of complications related to neutropenia and several other problems, as extensively described in the present report, with support of strong scientific evidence and examples in the state of the art.

The invention, that is, the use of the biological response modifier (proteic aggregate of ammonium and magnesium phospholinoleate-palmitoleate anhydride) for this specific application or usefulness, that is, to fight immunosuppression and neutropenia associated to cancer and aggravated by other drugs and treatments, can be used in clinical practice in 5 (five) ways:

1) Use of the biological response modifier (proteic aggregate of ammonium and magnesium phospholinoleate-palmitoleate anhydride) with prior, concomitant or subsequent non-drug treatments, for the preventive, curative or palliative treatment of immunosuppression and neutropenia.

2) Use of the biological response modifier (proteic aggregate of ammonium and magnesium phospholinoleate-palmitoleate anhydride) with prior, concomitant or subsequent drug treatments for cancer specifically targeted at the preventive, curative or palliative treatment of immunosuppression and neutropenia. The referred drugs or compounds, alone or in combination, to be used in the primary disease (cancer) can be selected by medical professionals prior to their use, among the various available options in the state of the art.

3) Use of the biological response modifier (proteic aggregate of ammonium and magnesium phospholinoleate-palmitoleate anhydride) in the manufacture of new drugs for the treatment of chronic systemic diseases such as cancer, in the form of drug associations or combinations with compounds aimed for the treatment of the primary disease (cancer). These formulations or associations shall include the biological response modifier (proteic aggregate of ammonium and magnesium phospholinoleate-palmitoleate anhydride) as a component aimed to counterbalance the immunosuppressive effects and/or the effects caused by neutropenia usually caused or aggravated by these other compounds.

4) Use of the biological response modifier (proteic aggregate of ammonium and magnesium phospholinoleate-palmitoleate anhydride) with prior, concomitant or subsequent anticancer drug treatments, aimed at preventive, curative and palliative treatment of immunosuppression and neutropenia. The referred compounds or drugs, alone or in combination to be used in the treatment of the primary disease (cancer) can be selected by the medical professionals among the various options available in the state of the art, and also associated to classes or groups of compounds in the current state of the art, for the specific purpose of treating immunosuppression and neutropenia related to cancer and the treatments.

5) Use of the biological response modifier (proteic aggregate of ammonium and magnesium phospholinoleate-palmitoleate anhydride) in the manufacture of new drugs for the treatment of chronic systemic diseases such as cancer, in the form of drug associations or combinations with compounds specifically targeted for the preventive, curative or palliative treatment of immunosuppression and neutropenia.

(D-1) The invention, that is, the association or combination of the biological response modifier (proteic aggregate of ammonium and magnesium phospholinoleate-palmitoleate anhydride) with other treatments, according to the purposes of the invention, and specifically in the treatment of immunosuppression and neutropenia, can be used in clinical practice with prior, concomitant or subsequent anticancer non-drug treatments in the current state of the art, such as surgery and radiotherapy.

(D-2) The invention, that is, the association or combination of the biological response modifier (proteic aggregate of ammonium and magnesium phospholinoleate-palmitoleate anhydride) with other treatments, according to the purposes of the invention, and specifically in the treatment of immunosuppression and neutropenia, can be used in clinical practice with prior, concomitant or subsequent anticancer drug treatments in the current state of the art.

(D-3) The invention, that is, the association or combination of the biological response modifier (proteic aggregate of ammonium and magnesium phospholinoleate-palmitoleate anhydride) with other treatments, according to the purposes of the invention, and specifically in the treatment of immunosuppression and neutropenia, can be used in clinical practice with prior, concomitant or subsequent anticancer drug treatments in the current state of the art, and also combined or associated to other compounds used in the state of the art in the specific treatment of immunosuppression and neutropenia.

(D-4) The invention, that is, the association or combination of the biological response modifier (proteic aggregate of ammonium and magnesium phospholinoleate-palmitoleate anhydride) with other treatments, according to the purposes of the invention, and specifically in the treatment of immunosuppression and neutropenia, can be used in clinical practice as a component in the manufacture of new drugs, in the form of drug associations with other compounds or drugs in the current state of the art, specifically targeted for the preventive, curative or palliative treatment of immunosuppression and neutropenia associated to chronic systemic diseases such as cancer.

(D-5) The invention, that is, the association or combination of the biological response modifier (proteic aggregate of ammonium and magnesium phospholinoleate-palmitoleate anhydride) with other treatments, according to the purposes of the invention, and specifically in the treatment of immunosuppression and neutropenia, can be used in clinical practice with other prior, concomitant or subsequent anticancer drug treatments known in the state of the art and also in combination or association with other compounds used in the state of the art for the specific treatment of immunosuppression and neutropenia, and these compounds can be selected among the following classes and categories, with examples of compounds used in the treatment of immunosuppression and neutropenia.

The invention claimed is:

1. A compound for use in a method of treatment of lung cancer, including precancerous lesions, and adverse events caused by said cancer or anti-cancer agents and treatments, including cancer cachexia, lymphopenia, neutropenia and febrile neutropenia of said cancer, the compound comprising in combination:
   (a) an immunomodulator, wherein the immunomodulator is a proteic aggregate of ammonium and magnesium phospholinoleate-palmitoleate anhydride, with molecular weight of 320.000 Dalton, having of 11.6±4.0% of total lipids (22.7±5.0% of palmitoleic acid, 42.9±2.0% of linoleic acid, 32.0±3.0% of oxidated linoleic acid), 20.1±0.9% of magnesium ions, 10.0±3.3% of ammonium ions, 45.2+2.7% of phosphate, and 0.49±0.01% of proteins, and
   (b) at least one anti-cancer agent suitable for treating said cancer, said agent providing synergistic effects without additional toxicity when used with the immunomodulator, wherein the anti-cancer agent is cytokines (interleukin-2 (IL-2), interleukin 12(IL-12), interferon alpha, interferon alpha-2a, peginterferon alpha-2a, interferon alpha-2b, peginterferon alpha-2b, interferon alpha-n1, interferon alphacon-1, interferon beta, interferon beta-1a, interferon beta-1 b, tumor necrosis factor (TNF)), wherein the anti-cancer treatment is selected from the group consisting of: surgical procedures (surgery, cryosurgery, electrocauterization, surgery associated to polarized light or laser with the use of photosensitizing substances, removal of lesions by chemical abrasion, removal of lesions by electrocauterization, endoscopic ablation, endoscopic radiofrequency ablation with the use of balloon catheter) transplantation of bone marrow cells, systemic and localized radiotherapy, and combinations thereof.

2. The compound according to claim 1, wherein the at least one anti-cancer agent is cytokines.

3. The compound according to claim 1, wherein the amino acid content in the proteic aggregate is: Asp 7.19%, Thr 3.56%, Ser 7.56%, Glu 8.53%, Pro 0.5%, Gly 9.69%, Ala 7.46%, Val 1.0%, Met 4.38%, Isoleu 2.54%, Leu 3.03%, Tyr 0.5%, Phe L0%, His 2.83%, Lys 3.56%, Trp 1.3%, and Arg 35.2%.

4. The compound for use according to claim 1, wherein the cancer cachexia is selected from the group consisting of: primary cancer cachexia and secondary cancer cachexia.

5. A method of treating a subject with lung cancer, the method comprising administering a therapeutically effective amount of the compound of claim 1 to a said subject; wherein the anti-cancer agent or treatment is suitable for treating said cancer.

6. The method according to claim 5, wherein the immunomodulator and the anti-cancer agents or treatments to be associated to the immunomodulator, is performed jointly, simultaneously, consecutively or sequentially, in a procedure judged effective against said cancer.

7. The method according to claim 5 or 6, wherein the anti-cancer agent or treatment is suitable for treating the cancer lesion.

8. A method of treating cancer cachexia in a subject with lung cancer, the method comprising administering to the subject an effective amount of the compound according to claim 1.

9. The compound according to claim 1 wherein said synergistic effects are selected from the group consisting of potentiating therapeutic effects, increasing the time period of therapeutic effects, using smaller doses of anti-cancer agents, using higher doses of anti-cancer agents, recovering the effectiveness of the immune system, recovering of primary and secondary cachexia, recovering of neutropenia, febrile neutropenia and lymphopenia and a shorter period of treatment.

10. A pharmaceutical composition comprising the compound of claim 1 and a pharmaceutically acceptable carrier.

11. The pharmaceutical composition according to claim 1, further comprising a component selected from the group consisting of: an excipient, a suspension, a transporter, a stabilizers and combinations thereof.

12. The pharmaceutical composition according to claim 11, wherein the composition is a preparation selected from the group consisting of: an aqueous solution, a solid form solution, a microencapsulation, and liposomes.

13. The pharmaceutical composition according to claim 12, wherein the composition is present in an injectable form, or is present in an oral form.

14. Use of proteic aggregate of ammonium and magnesium phospholinoleate-palmitoleate anhydride, as a fixed component for the manufacture of new drugs with at least one other pharmacologically active compound or substance select among the compounds of claim 2.

* * * * *